(12) United States Patent
Li et al.

(10) Patent No.: US 11,247,998 B2
(45) Date of Patent: Feb. 15, 2022

(54) PIPERAZINE HETEROARYL DERIVATIVE, PREPARATION METHOD THEREFOR AND USE OF SAME IN MEDICINE

(71) Applicants: JIANGSU HENGRUI MEDICINE CO., LTD., Lianyungang (CN); SHANGHAI HENGRUI PHARMACEUTICAL CO., LTD., Shanghai (CN)

(72) Inventors: Xin Li, Shanghai (CN); Wei He, Shanghai (CN); Yang Chen, Shanghai (CN); Feng He, Shanghai (CN); Weikang Tao, Shanghai (CN)

(73) Assignees: JIANGSU HENGRUI MEDICINE CO., LTD., Lianyungang (CN); SHANGHAI HENGRUI PHARMACEUTICAL CO., LTD., Shanghai (CN)

( * ) Notice: Subject to any disclaimer, the term of this patent is extended or adjusted under 35 U.S.C. 154(b) by 24 days.

(21) Appl. No.: 16/632,973

(22) PCT Filed: Jul. 26, 2018

(86) PCT No.: PCT/CN2018/097170
§ 371 (c)(1),
(2) Date: Jan. 22, 2020

(87) PCT Pub. No.: WO2019/020070
PCT Pub. Date: Jan. 31, 2019

(65) Prior Publication Data
US 2020/0157111 A1   May 21, 2020

(30) Foreign Application Priority Data

Jul. 27, 2017 (CN) .......................... 201710621744.9
Nov. 1, 2017 (CN) .......................... 201711058986.8

(51) Int. Cl.
| | |
|---|---|
| C07D 241/36 | (2006.01) |
| C07D 487/00 | (2006.01) |
| A61K 31/495 | (2006.01) |
| C07D 487/04 | (2006.01) |
| A61P 31/12 | (2006.01) |
| A61K 31/4985 | (2006.01) |

(52) U.S. Cl.
CPC ........ *C07D 487/04* (2013.01); *A61K 31/4985* (2013.01); *A61P 31/12* (2018.01)

(58) Field of Classification Search
CPC .......................... C07D 241/36; C07D 487/04; A61K 31/4985; A61P 31/20
USPC .................. 514/249; 544/349, 350
See application file for complete search history.

(56) References Cited

U.S. PATENT DOCUMENTS

| | | | |
|---|---|---|---|
| 2005/0009831 A1* | 1/2005 | Ratcliffe | ............... C07D 487/04 |
| | | | 514/249 |
| 2008/0318935 A1 | 12/2008 | Beckett et al. | |
| 2011/0034443 A1 | 2/2011 | Beckett et al. | |
| 2015/0051189 A1 | 2/2015 | Le Diguarher et al. | |
| 2015/0133428 A1 | 5/2015 | Velaparthi et al. | |
| 2016/0311824 A1* | 10/2016 | Velaparthi | ............... A61P 43/00 |

FOREIGN PATENT DOCUMENTS

| | | | |
|---|---|---|---|
| CN | 101686989 A | 3/2010 | |
| CN | 102464661 A | 5/2012 | |
| CN | 102875270 A | 1/2013 | |
| CN | 105916855 A | 8/2016 | |
| RU | 2470937 C2 | 12/2012 | |
| WO | 2001068642 A1 | 9/2001 | |
| WO | 2011161437 A1 | 12/2011 | |
| WO | 2014029193 A1 | 2/2014 | |
| WO | 2015011281 A1 | 1/2015 | |
| WO | 2015118057 A1 | 8/2015 | |
| WO | 2016016196 A1 | 2/2016 | |

(Continued)

OTHER PUBLICATIONS

PubChem CID 90793128. (Year: 2015).*
Harry La Janssen et al., Pegylated Interferon Alfa-2b Alone or in Combination With Lamivudine for HBeAg-Positive Chronic Hepatitis B: A Randomised Trial, Lancet. Jan. 8-14, 2005; vol. 365(9454): pp. 123-129.
George K.K. Lau, M.D. et al., Peginterferon Alfa-2a, Lamivudine, and the Combination for HBeAg-Positive Chronic Hepatitis B, The New England Journal of Med. Jun. 30, 2005; 352(26): pp. 2682-2695.

(Continued)

*Primary Examiner* — Shengjun Wang
(74) *Attorney, Agent, or Firm* — Morgan, Lewis & Bockius LLP; Christopher J. Betti; Estella M. Gustilo

(57) ABSTRACT

The present invention relates to a piperazine heteroaryl derivative, a preparation method therefor and the use of same in medicine. In particular, the present invention relates to the piperazine heteroaryl derivative as shown in the general formula (I), a preparation method therefor, a pharmaceutical composition comprising the derivative, and the use of same as a capsid protein inhibitor, in particular in the prevention and/or treatment of diseases such as hepatitis B, influenza, herpes, AIDS, etc. The definitions of each group in the general formula (I) are the same as those defined in the description.

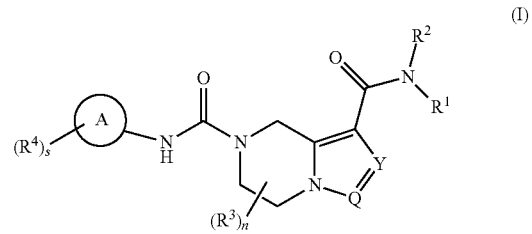

(I)

19 Claims, No Drawings

(56) References Cited

FOREIGN PATENT DOCUMENTS

| WO | 2016113273 A1 | 7/2016 |
|---|---|---|
| WO | 2017076791 A1 | 5/2017 |
| WO | 2017198744 A1 | 11/2017 |

OTHER PUBLICATIONS

Robert Perillo, Benefits and Risks of Interferon Therapy for Hepatitis B, Hepatology. May 2009; vol. 49, No. 5 Suppl, 2009; pp. S103-S11.
Jules L. Dienstag, Benefits and Risks of Nucleoside Analog Therapy for Hepatitis B, Hepatology, vol. 49, No. 5, Suppl., 2009; pp. S112-S121.
Sergey A. Prikhod'ko et al., The Ionic Liquid [bmim]Br as an Alternative Medium for the Catalytic Cleavage of Aromatic C—F and C—Cl Bonds, Tetrahedron Letters, 51(17), 2010, pp. 2265-2268.
Paul A. Barsanti et al., Structure-Based Drug Design of Novel Potent and Selective Tetrahydropyrazolo[1,5-a] pyrazines as ATR Inhibitors, ACS Medicinal Chemistry Letters 2015, 6(1), pp. 37-41.
Yun-Long Li et al., Preparation of 1-(3-aminobenzo[d]isoxazol-5-yl)-1Hpyrazolo[4,3-d]pyrimidin-7(6H)-Ones as Potent, Selective, and Efficacious Inhibitors of Coagulation Factor Xa, Bioorganic & Medicinal Chemistry Letters 16 (2006), pp. 5176-5182.
Kenji Fukunaga et al., Discovery of Novel 2-(alkylmorpholin-4-yl)-6-(3-fluoropyridin-4-yl)-pyrimidin-4(3H)-ones as Orally-Active GSK-3b Inhibitors for Alzheimer's Disease, Bioorganic & Medicinal Chemistry Letters 25 (2015) pp. 1086-1091.
Mingze Qin, Discovery of Novel Diaryl Urea Derivatives Bearing a Triazole Moiety as Potential Antitumor Agents, European Journal of Medicinal Chemistry 115, (2016), 115, pp. 1-13.
Xufeng Cao et al., Design, Synthesis, and Structure-Activity Relationship Studies of Novel Fused Heterocycles-Linked Triazoles with Good Activity and Water Solubility, Journal of Medicinal Chemistry, 2014, 57, pp. 3687-3706.
Thomas James et al., A Modular Lead-Oriented Synthesis of Diverse Piperazine, 1,4-Diazepane and 1,5-Diazocane Scaffolds, Organic and Biomolecular Chemistry, The Royal Society of Chemisty 2014, pp. 2584-2591.
Office Action issued in the related Russian Patent Application No. 2020105275/04 dated Oct. 13, 2020.
International Search Report in the related Russian Patent Application No. 2020105275/04 dated Sep. 24, 2020.
Supplementary European Search Report in the related European Patent Application No. 18837963.0 dated Mar. 19, 2021.

\* cited by examiner

PIPERAZINE HETEROARYL DERIVATIVE, PREPARATION METHOD THEREFOR AND USE OF SAME IN MEDICINE

CROSS-REFERENCE TO RELATED APPLICATIONS

This application is the national stage of International Patent Application No. PCT/CN2018/097170, filed Jul. 26, 2018, which claims the benefit of and priority to Chinese Patent Application No. 201710621744.9, filed Jul. 27, 2017, and Chinese Patent Application No. 201711058986.8, filed Nov. 1, 2017, each of which are incorporated herein by reference in their entirety.

FIELD OF THE INVENTION

The present invention belongs to the field of medicine, and relates to a piperazinoheteroaryl derivative, a method for preparing the same, and a use thereof in medicine. In particular, the present invention relates to a piperazinoheteroaryl derivative of formula (I), a method for preparing the same, a pharmaceutical composition comprising the same, and a use thereof as a capsid protein inhibitor, particularly in preventing and/or treating diseases such as hepatitis B, influenza, herpes and AIDS.

BACKGROUND OF THE INVENTION

Chronic hepatitis B virus (HBV) infection is already a global health issue. According to the World Health Organization, about 2 billion people worldwide had been infected with HBV, of which 240 million are chronic HBV-infected people. About 650,000 people die each year from liver failure, liver cirrhosis and hepatocellular carcinoma (HCC) caused by HBV infection. 30% of liver cirrhosis patients and 45% of HCC patients are caused by HBV infection worldwide. Although prophylactic HBV vaccines can be used, chronic HBV infection has become a worldwide medical issue due to the lack of effective drugs.

At present, there are mainly two classes of drugs for treating chronic HBV infection: alpha-interferon formulations (such as pegylated alpha-interferon) and nucleoside analogues that inhibit HBV DNA polymerase (such as lamivudine, adefovir and the like). However, the interferon formulations have severe side effects and poor tolerance, and only a small percentage of patients can have a sustained clinical response to interferon therapy (*Lancet.* 2005 Jan. 8-14; 365(9454): 123-9.; *N Engl J Med.* 2005 Jun. 30; 352(26):2682-95.; *Hepatology.* 2009 May; 49(5 Suppl): S103-11). As a competitive inhibitor of reverse transcriptase, nucleoside analog drugs exert an antiviral effect by blocking the synthesis of HBV DNA strands. However, existing nucleoside analog drugs also have issues such as inducing the reverse transcriptase to produce drug-resistant mutations and a poor efficacy against drug-resistant strains. Moreover, these drugs are often difficult to completely eliminate HBV infection, even if they are administrated for a long time; once the drug is withdrawn, there might be a serious rebound phenomenon, thus lifelong medication is needed (*Hepatology.* 2009 May; 49(5 Suppl):S112-21). Therefore, there is an urgent need to develop a novel, safe and effective drug for chronic hepatitis B.

The low cure rate of chronic HBV infection is closely related to the characteristics of hepatitis B virus (HBV). HBV is an enveloped, partially double-stranded DNA (dsDNA) virus of Hepadnaviridae family. The outermost layer of mature HBV viral particles is an envelope protein, encapsulated by the HBV nucleocapsid. The nucleocapsid is also called core particle, and is composed of capsid protein, HBV relaxed circular DNA (rcDNA) and HBV reverse transcriptase bound to the 5' end of the negative strand of rcDNA. Upon infection, rcDNA is converted to covalently closed circle DNA (cccDNA) in the host cell nucleus as a replication template of HBV. An important step during HBV replication is the encapsidation. Pregenomic RNA (pgRNA) transcribed from cccDNA needs to be encapsulated in the capsid protein together with HBV reverse transcriptase to complete the assembly step, thereby triggering subsequent reverse transcription. The HBV reverse transcriptase and pgRNA need to be properly encapsulated by the capsid protein before reverse transcription. Therefore, blocking capsid protein assembly or accelerating capsid protein degradation can block the capsid assembly process, thereby affecting viral replication. Moreover, the N-terminal 149 amino acid residues (Cp149), which constitute the core protein dimerization motif and assembly domain, have no human protein homologous sequences. Therefore, the capsid protein assembly inhibitor is considered as a new target for anti-hepatitis B drug development. Due to the different mechanism with conventional antiviral drugs, the capsid protein inhibitor can be combined with a DNA polymerase inhibitor to synergistically inhibit HBV replication and prevent drug resistance, providing a safer and more effective treatment for chronic hepatitis B infection.

At present, there are mainly two classes of capsid protein inhibitors: heteroaryl dihydropyrimidines (HAPs) and phenylacrylamides, such as GLS-4, NVR-3778 and the like. Related patent applications include WO2001068642, WO2014029193, WO2015011281, WO2016016196, WO2017076791, WO2016113273 and the like. However, most of the compounds directed to this target are in clinical research, and there are no marketed drugs. Therefore, there is still a need to continuously develop capsid protein inhibitors to improve the safety and effectiveness of the drugs, and to overcome the problem of chronic HBV infection at an early date.

The capsid protein inhibitor interferes with the normal assembly of capsid protein by binding to the assembly domain of the core protein dimerization motif, thereby affecting HBV replication. Therefore, a good pharmacokinetic absorption and a high bioavailability (which can result in higher concentration of the compound in the body) can more effectively block HBV replication.

The present invention provides a novel structure of a capsid protein inhibitor of formula (I), wherein the substituent on the heteroaryl is an acylamino group, and the amino group in the acylamino group is preferably a secondary amino group. The present invention designs a comparative example (Example 59) that corresponds to the compound of formula (I), in the $NR^1R^2$ moiety, $R^1$ and $R^2$ together with the nitrogen atom forms a ring having a tertiary amino group. The comparative example demonstrates that when the amino group in the acylamino group on the heteroaryl is a secondary amino group, the compound exhibits a significantly improved biological activity, and has an obvious inhibition effect on the normal assembly of HBV capsid protein, a good pharmacokinetic absorption and a high bioavailability. Meanwhile, the novel structure of the compound of formula (I) has no or little effect on the in vitro proliferation inhibition of HepG2 cells, and shows a good safety.

SUMMARY OF THE INVENTION

The object of the present invention is to provide a compound of formula (I):

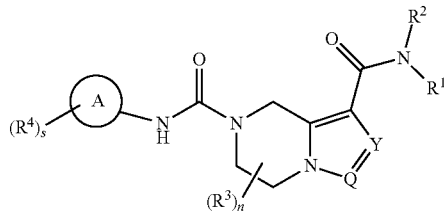

or a tautomer, mesomer, racemate, enantiomer, diastereomer thereof, or mixture thereof,
or a pharmaceutically acceptable salt thereof,
wherein:
ring A is aryl or heteroaryl;
Y is N or $CR^5$;
Q is N or CH;
$R^1$ is selected from the group consisting of alkyl, haloalkyl, hydroxyalkyl, cycloalkyl, heterocyclyl, aryl and heteroaryl, wherein the alkyl, haloalkyl, cycloalkyl, heterocyclyl, aryl and heteroaryl are each independently optionally further substituted by one or more substituents selected from the group consisting of halogen, alkyl, haloalkyl, alkoxy, haloalkoxy, cyano, amino, nitro, hydroxy, hydroxyalkyl, cycloalkyl, heterocyclyl, aryl, heteroaryl, $-OR^6$, $-C(O)R^6$, $-C(O)OR^6$ and $-S(O)_mR^6$;
$R^2$ is selected from the group consisting of hydrogen, alkyl, haloalkyl, hydroxyalkyl, cycloalkyl, heterocyclyl, aryl and heteroaryl, wherein the alkyl, haloalkyl, cycloalkyl, heterocyclyl, aryl and heteroaryl are each independently optionally further substituted by one or more substituents selected from the group consisting of halogen, alkyl, haloalkyl, alkoxy, haloalkoxy, cyano, amino, nitro, hydroxy, hydroxyalkyl, cycloalkyl, heterocyclyl, aryl, heteroaryl, $-OR^6$, $-C(O)R^6$, $-C(O)OR^6$ and $-S(O)_mR^6$;
each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, $-OR^6$, $-C(O)R^6$, $-C(O)OR^6$ and $-S(O)_mR^6$;
each $R^4$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, $-OR^6$, $-C(O)R^6$, $-C(O)OR^6$ and $-S(O)_mR^6$;
$R^5$ is selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl and heteroaryl;
$R^6$ is selected from the group consisting of hydrogen, alkyl, haloalkyl, amino, hydroxy, hydroxyalkyl, cycloalkyl, heterocyclyl, aryl and heteroaryl;
n is 0, 1, 2 or 3;
m is 0, 1 or 2; and
s is 0, 1, 2, 3 or 4.

In a preferred embodiment of the present invention, compound of formula (I) according to the present invention is a compound of formula (II):

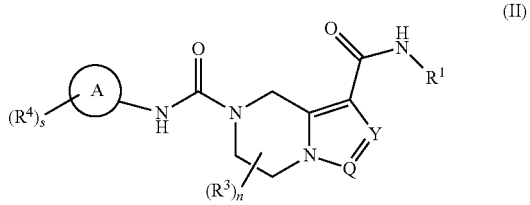

wherein:
ring A, Y, Q, $R^1$, $R^3$, $R^4$, s and n are as defined in formula (I).

In another preferred embodiment of the present invention, the compound of formula (I) according to the present invention is a compound of formula (III), formula (IV), formula (V) or formula (VI):

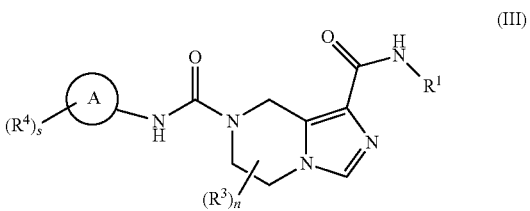

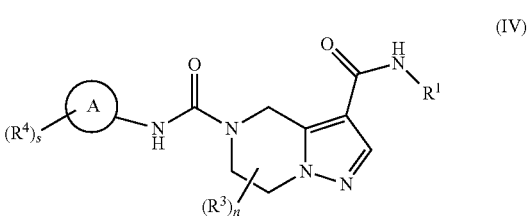

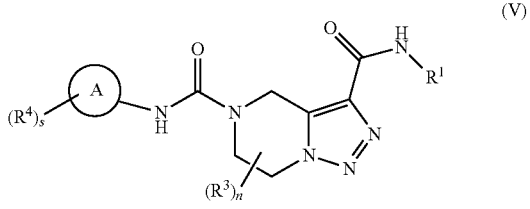

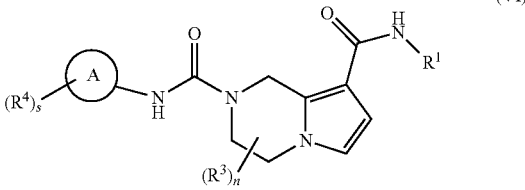

wherein:
ring A, $R^1$, $R^3$, $R^4$, s and n are as defined in formula (I).

In another preferred embodiment of the present invention, in the compound of formula (I) according to the present invention, ring A is phenyl or pyridyl.

In another preferred embodiment of the present invention, the compound of formula (I) according to the present invention is a compound of formula (VII), formula (VIII), formula (IX) or formula (X):

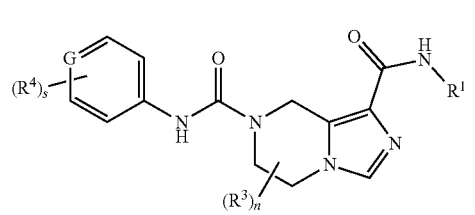
(VII)

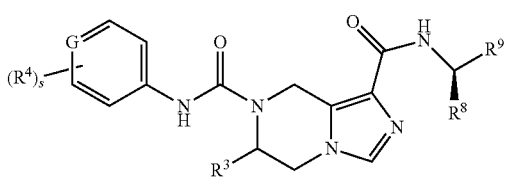
(VII-A)

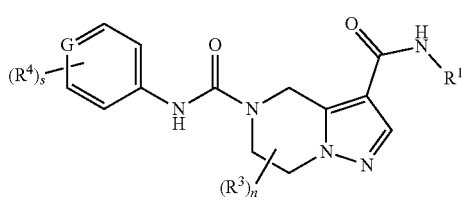
(VIII)

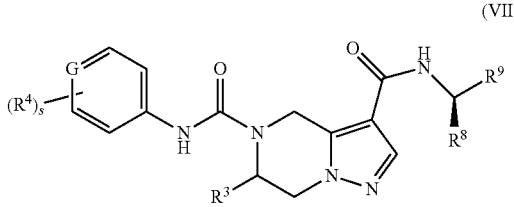
(VIII-A)

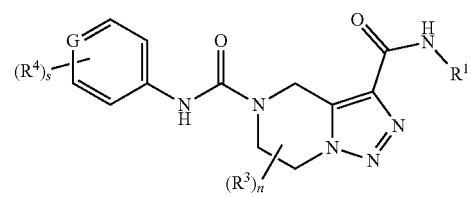
(IX)

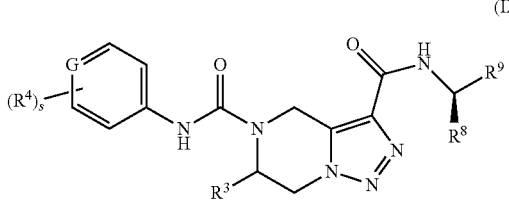
(IX-A)

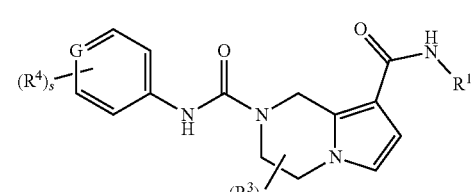
(X)

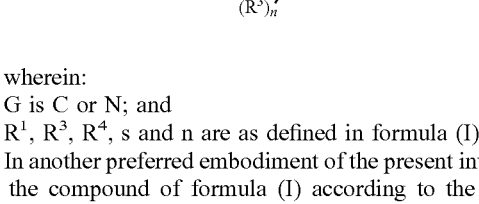
(X-A)

wherein:
G is C or N; and
$R^1$, $R^3$, $R^4$, s and n are as defined in formula (I).

In another preferred embodiment of the present invention, in the compound of formula (I) according to the present invention, $R^1$ is selected from the group consisting of alkyl, haloalkyl, cycloalkyl, heterocyclyl and aryl, wherein the alkyl, cycloalkyl, heterocyclyl and aryl are optionally further substituted by one or more substituents selected from the group consisting of halogen, alkyl, alkoxy and hydroxy.

In another preferred embodiment of the present invention, the compound of formula (I) according to the present invention is a compound of formula (VII-A), formula (VIII-A), formula (IX-A) or formula (X-A):

wherein:
G is C or N;
$R^8$ is alkyl, preferably methyl;
$R^9$ is alkyl, wherein the alkyl is optionally further substituted by one or more halogen; and
$R^3$, $R^4$, s and n are as defined in formula (I).

In another preferred embodiment of the present invention, in the compound of formula (I) according to the present invention, $R^3$ is hydrogen or alkyl.

In another preferred embodiment of the present invention, in the compound of formula (I) according to the present invention, $R^4$ is selected from the group consisting of hydrogen, halogen, haloalkyl and cyano.

Typical compounds of formula (I) include, but are not limited to:

| Example No. | Structure and name of the compound |
|---|---|
| 1 | 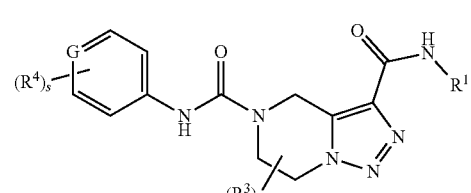<br>1<br>(R)-N$^7$-(3,4,5-Trifluorophenyl)-N$^1$-(1,1,1-trifluoropropan-2-yl)-5,6-dihydroimidazo[1,5-a]pyrazine-1,7(8H)-dicarboxamide |

-continued

| Example No. | Structure and name of the compound |
|---|---|
| 2 | 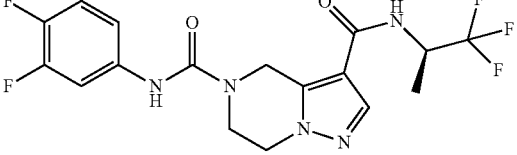<br>2<br>(R)-N⁵-(3,4-Difluorophenyl)-N³-(1,1,1-trifluoropropan-2-yl)-6,7-dihydropyrazolo[1,5-a]pyrazine-3,5(4H)-dicarboxamide |
| 3 | 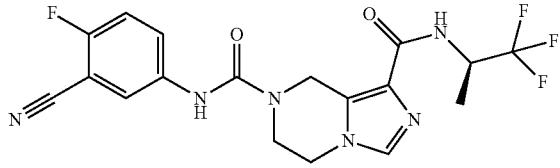<br>3<br>(R)-N⁷-(3-Cyano-4-fluorophenyl)-N¹-(1,1,1-trifluoropropan-2-yl)-5,6-dihydroimidazo[1,5-a]pyrazine-1,7(8H)-dicarboxamide |
| 4 | 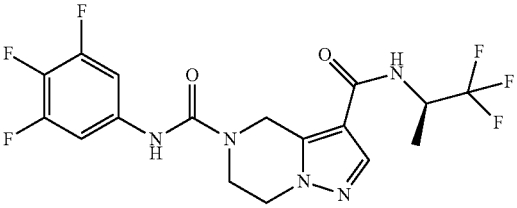<br>4<br>(R)-N⁵-(3,4,5-Trifluorophenyl)-N³-(1,1,1-trifluoropropan-2-yl)-6,7-dihydropyrazolo[1,5-a]pyrazine-3,5(4H)-dicarboxamide |
| 5 | 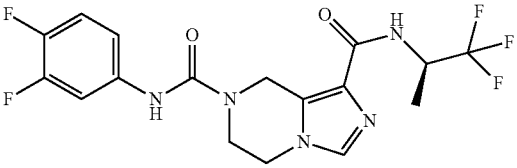<br>5<br>(R)-N⁷-(3,4-Difluorophenyl)-N¹-(1,1,1-trifluoropropan-2-yl)-5,6-dihydroimidazo[1,5-a]pyrazine-1,7(8H)-dicarboxamide |
| 6 | 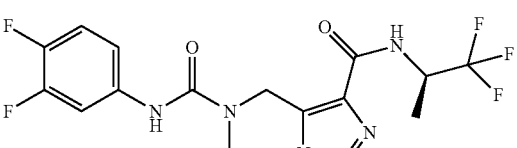<br>6<br>(S)-N⁷-(3,4-Difluorophenyl)-6-methyl-N¹-((R)-1,1,1-trifluoropropan-2-yl)-5,6-dihydroimidazo[1,5-a]pyrazine-1,7(8H)-dicarboxamide |
| 7 | 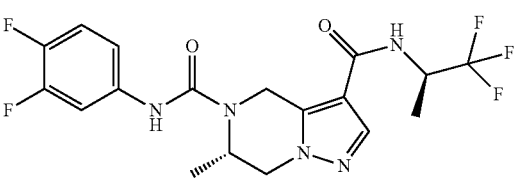<br>7 |

| Example No. | Structure and name of the compound |
|---|---|
| | (S)-N⁵-(3,4-Difluorophenyl)-6-methyl-N³-((R)-1,1,1-trifluoropropan-2-yl)-6,7-dihydropyrazolo[1,5-a]pyrazine-3,5(4H)-dicarboxamide |
| 8 | 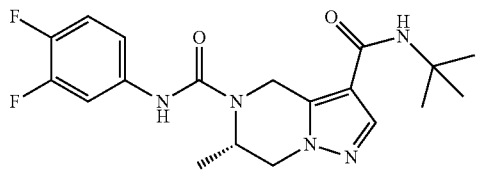<br>8<br>(S)-N³-(Tert-butyl)-N⁵-(3,4-difluorophenyl)-6-methyl-6,7-dihydropyrazolo[1,5-a]pyrazine-3,5(4H)-dicarboxamide 8 |
| 9 | 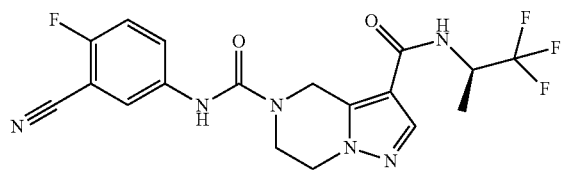<br>9<br>(R)-N⁵-(3-Cyano-4-fluorophenyl)-N³-(1,1,1-trifluoropropan-2-yl)-6,7-dihydropyrazolo[1,5-a]pyrazine-3,5(4H)-dicarboxamide 9 |
| 10 | 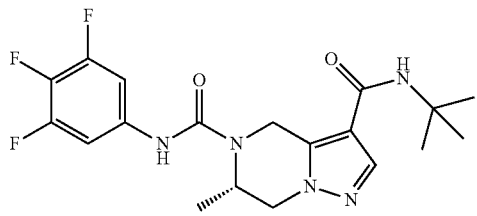<br>10<br>(S)-N³-(Tert-butyl)-6-methyl-N⁵-(3,4,5-trifluorophenyl)-6,7-dihydropyrazolo[1,5-a]pyrazine-3,5(4H)-dicarboxamide 10 |
| 11 | 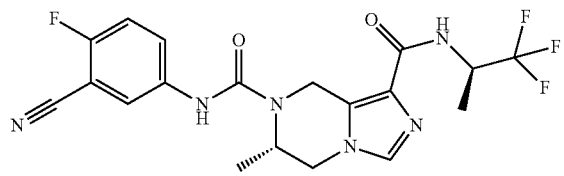<br>11<br>(S)-N⁷-(3-Cyano-4-fluorophenyl)-6-methyl-N¹-((R)-1,1,1-trifluoropropan-2-yl)-5,6-dihydroimidazo[1,5-a]pyrazine-1,7(8H)-dicarboxamide 11 |
| 12 | 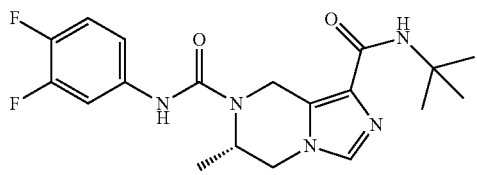<br>12<br>(S)-N¹-(Tert-butyl)-N⁷-(3,4-difluorophenyl)-6-methyl-5,6-dihydroimidazo[1,5-a]pyrazine-1,7(8H)-dicarboxamide 12 |

-continued

| Example No. | Structure and name of the compound |
|---|---|
| 13 | 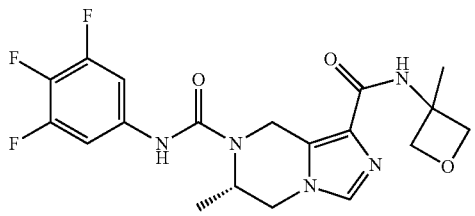

13

(S)-6-Methyl-$N^1$-(3-methyloxetan-3-yl)-$N^7$-(3,4,5-trifluorophenyl)-5,6-dihydroimidazo[1,5-a]pyrazine-1,7(8H)-dicarboxamide 13 |
| 14 | 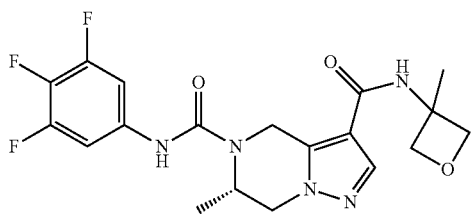

14

(S)-6-Methyl-$N^3$-(3-methyloxetan-3-yl)-$N^5$-(3,4,5-trifluorophenyl)-6,7-dihydropyrazolo[1,5-a]pyrazine-3,5(4H)-dicarboxamide 14 |
| 15 | 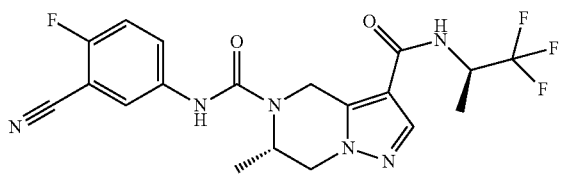

15

(S)-$N^5$-(3-Cyano-4-fluorophenyl)-6-methyl-$N^3$-((R)-1,1,1-trifluoropropan-2-yl)-6,7-dihydropyrazolo[1,5-a]pyrazine-3,5(4H)-dicarboxamide 15 |
| 16 | 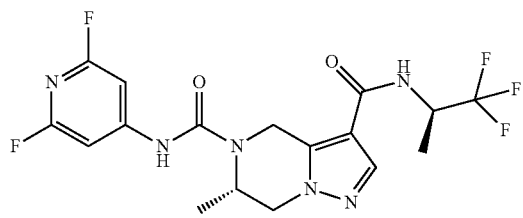

16

(S)-$N^5$-(2,6-Difluoropyridin-4-yl)-6-methyl-$N^3$-((R)-1,1,1-trifluoropropan-2-yl)-6,7-dihydropyrazolo[1,5-a]pyrazine-3,5(4H)-dicarboxamide 16 |
| 17 | 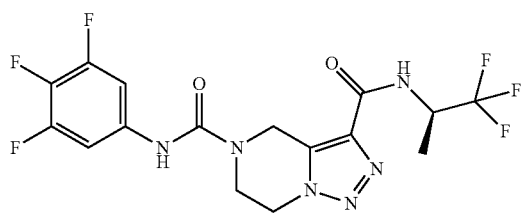

17

(R)-$N^5$-(3,4,5-Trifluorophenyl)-$N^3$-(1,1,1-trifluoropropan-2-yl)-6,7-dihydro-[1,2,3]triazolo[1,5-a]pyrazine-3,5(4H)-dicarboxamide 17 |

| Example No. | Structure and name of the compound |
|---|---|
| 18 | 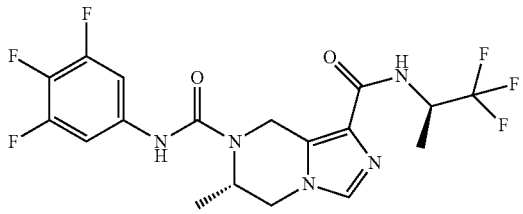<br>(S)-6-Methyl-N[7]-(3,4,5-trifluorophenyl)-N[1]-((R)-1,1,1-trifluoropropan-2-yl)-5,6-dihydroimidazo[1,5-a]pyrazine-1,7(8H)-dicarboxamide 18 |
| 19 | 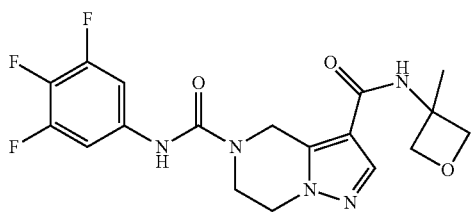<br>N[3]-(3-Methyloxetan-3-yl)-N[5]-(3,4,5-trifluorophenyl)-6,7-dihydropyrazolo[1,5-a]pyrazine-3,5(4H)-dicarboxamide 19 |
| 20 | 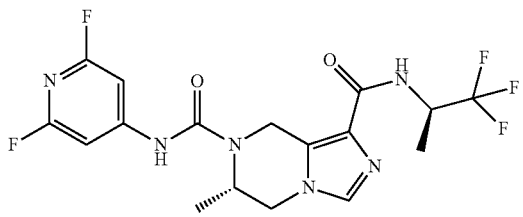<br>(S)-N[7]-(2,6-Difluoropyridin-4-yl)-6-methyl-N[1]-((R)-1,1,1-trifluoropropan-2-yl)-5,6-dihydroimidazo[1,5-a]pyrazine-1,7(8H)-dicarboxamide 20 |
| 21 | 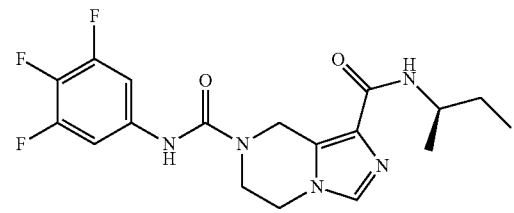<br>(R)-N[3]-(Sec-butyl)-N[5]-(3,4,5-trifluorophenyl)-6,7-dihydropyrazolo[1,5-a]pyrazine-3,5(4H)-dicarboxamide 21 |
| 22 | 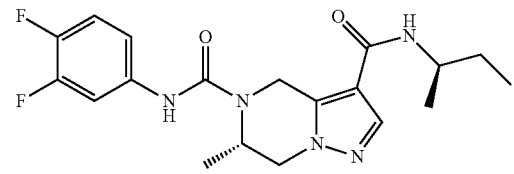<br>(S)-N[3]-((R)-Sec-butyl)-N[5]-(3,4-difluorophenyl)-6-methyl-6,7-dihydropyrazolo[1,5-a]pyrazine-3,5(4H)-dicarboxamide 22 |

-continued

| Example No. | Structure and name of the compound |
|---|---|
| 23 | 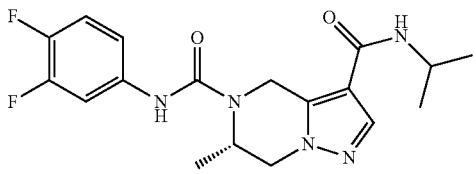

23

(S)-N⁵-(3,4-Difluorophenyl)-N³-isopropyl-6-methy-6,7-dihydropyrazolo[1,5-a]pyrazine-3,5(4H)-dicarboxamide 23 |
| 24 | 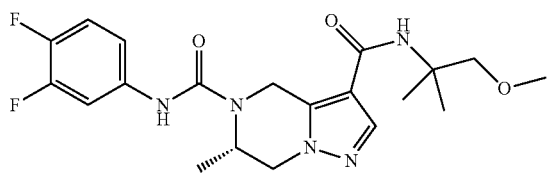

24

(S)-N⁵-(3,4-Difluorophenyl)-N³-(1-methoxy-2-methylpropan-2-yl)-6-methyl-6,7-dihydropyraxolo[1,5-a]pyrazine-3,5(4H)-dicarboxamide 24 |
| 25 | 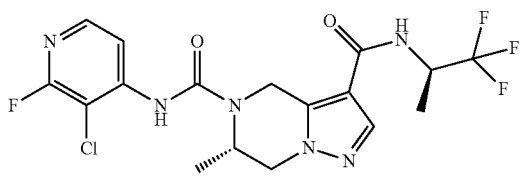

25

(S)-N⁵-(3-Chloro-2-fluoropyridin-4-yl)-6-methyl-N³-((R)-1,1,1-trifluoropropan-2-yl)-6,7-dihydropyrazolo[1,5-a]pyrazine-3,5(4H)-dicarboxamide 25 |
| 26 | 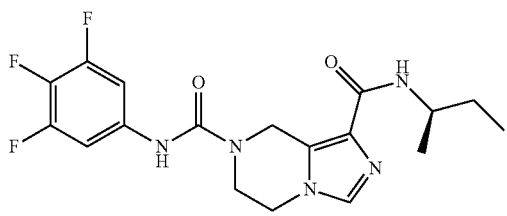

26

(R)-N¹-(Sec-butyl)-N⁷-(3,4,5-trifluorophenyl)-5,6-dihydroimidazo[1,5-a]pyrazine-1,7(8H)-dicarboxamide 26 |
| 27 | 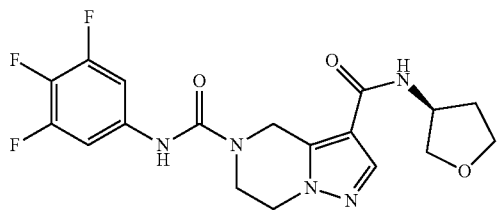

27

(S)-N³-(Tetrahydrofuran-3-yl)-N⁵-(3,4,5-trifluorophenyl)-6,7-dihydropyrazolo[1,5-a]pyrazine-3,5(4H)-dicarboxamide 27 |

| Example No. | Structure and name of the compound |
|---|---|
| 28 | 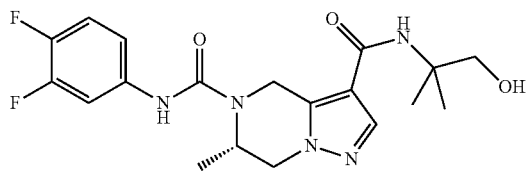<br>28<br>(S)-N⁵-(3,4-Difluorophenyl)-N³-(1-hydroxy-2-methylpropan-yl)-6-methyl-6,7-dihydropyrazolo[1,5-a]pyrazine-3,5(4H)-dicarboxamide 28 |
| 29 | 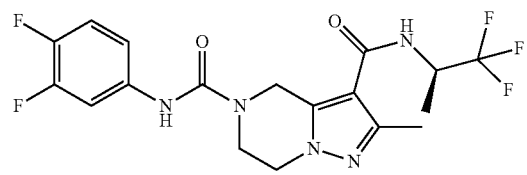<br>29<br>(R)-N⁵-(3,4-Difluorophenyl)-2-methyl-N³-(1,1,1-trifluoropropan-2-yl)-6,7-dihydropyrazolo[1,5-a]pyrazine-3,5(4H)-dicarboxamide 29 |
| 30 | 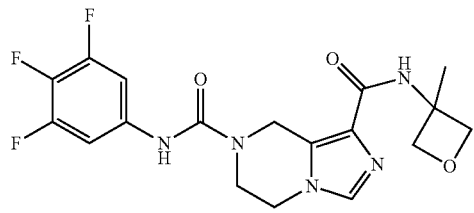<br>30<br>N¹-(3-Methyloxetan-3-yl)-N⁷-trifluorophenyl)5,6-dihydroimidazo[1,5-a]pyrazine-1,7(8H)-dicarboxamide 30 |
| 31 | 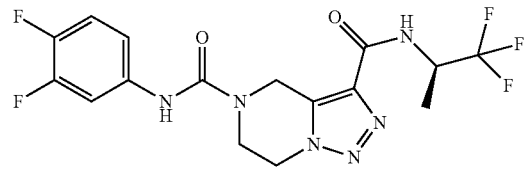<br>31<br>(R)-N⁵-(3,4-Difluorophenyl)-N³-(1,1,1-trifluoropropan-2-yl)-6,7-dihydro-[1,2,3]triazolo[1,5-a]pyrazine-3,5(4H)-dicarboxamide 31 |
| 32 | 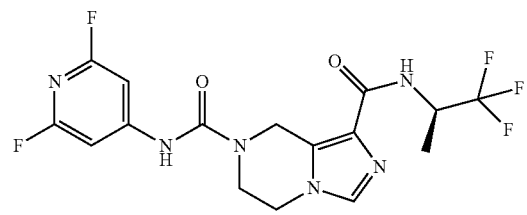<br>32<br>(R)-N⁷-(2,6-Difluoropyridin-4-yl)-N¹-(1,1,1-trifluoropropan-2-yl)-5,6-dihydroimidazo[1,5-a]pyrazine-1,7(8H)-dicarboxamide 32 |

| Example No. | Structure and name of the compound |
|---|---|
| 33 | 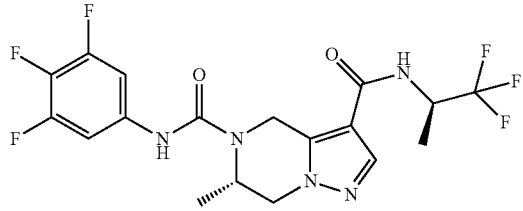
33
(S)-6-Methyl-$N^5$-(3,4,5-trifluorophenyl)-$N^3$-((R)-1,1,1-trifluoropropan-2-yl)-6,7-dihydropyrazolo[1,5-a]pyrazine-3,5(4H)-dicarboxamide 33 |
| 34 | 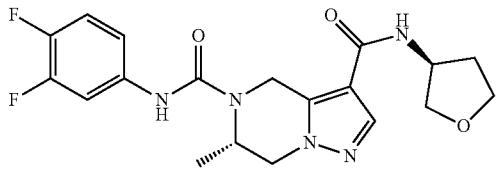
34
(S)-$N^5$-(3,4-Difluorophenyl)-6-methyl-$N^3$-((S)-tetrahydrofuran-3-yl)-6,7-dihydropyrazolo[1,5-a]pyrazine-3,5(4H)-dicarboxamide 34 |
| 35 | 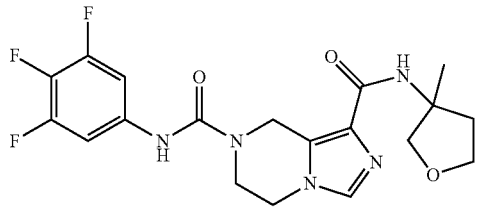
35
$N^1$-(3-Methyltetrahydrofuran-3-yl)-$N^7$-(3,4,5-trifluorophenyl)-5,6-dihydroimidazo[1,5-a]pyrazine-1,7(8H)-dicarboxamide 35 |
| 36 | 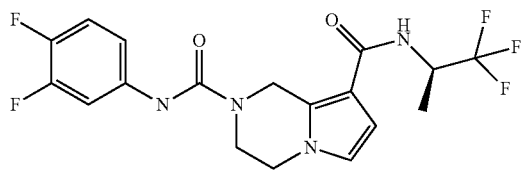
36
(R)-$N^2$-(3,4-Difluorophenyl)-$N^8$-(1,1,1-trifluoropropan-2-yl)-3,4-dihydropyrrolo[1,2-a]pyrazine-2,8(1H)-dicarboxamide 36 |
| 37 | 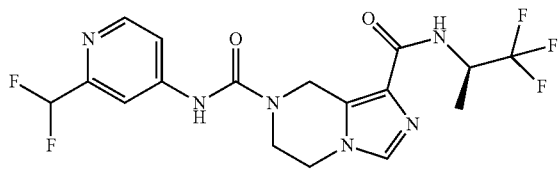
37
(R)-$N^7$-(2-(Difluoromethyl)pyridin-4-yl)-$N^1$-(1,1,1-trifluoropropan-2-yl)-5,6-dihydroimidazo[1,5-a]pyrazine-1,7(8H)-dicarboxamide 37 |

-continued

| Example No. | Structure and name of the compound |
|---|---|
| 38 | 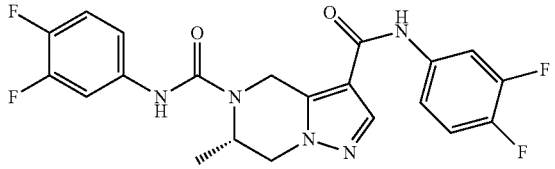<br>38<br>(S)-N³,N⁵-Bis(3,4-difluorophenyl)-6-methyl-6,7-dihydropyrazolo[1,5-a]pyrazine-3,5(4H)-dicarboxamide 38 |
| 39 | 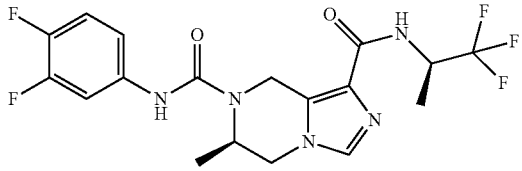<br>39<br>(R)-N⁷-(3,4-Difluorophenyl)-6-methyl-N¹-((R)-1,1,1-trifluoropropan-2-yl)-5,6-dihydroimidazo[1,5-a]pyrazine-1,7(8H)-dicarboxamide 39 |
| 40 | 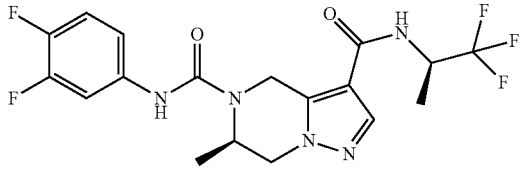<br>40<br>(R)-N⁵-(3,4-Difluorophenyl)-6-methyl-N³-((R)-1,1,1-trifluoropropan-2-yl)-6,7-dihydropyrazolo[1,5-a]pyrazine-3,5(4H)-dicarboxamide 40 |
| 41 | 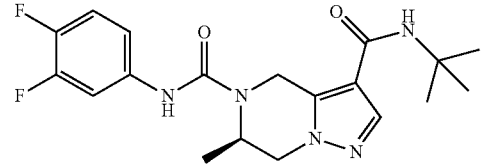<br>41<br>(R)-N³-(Tert-butyl)-N⁵-(3,4-difluorophenyl)-6-methyl-6,7-dihydropyrazolo[1,5-a)pyrazine-3,5(4H)-dicarboxamide 41 |
| 42 | 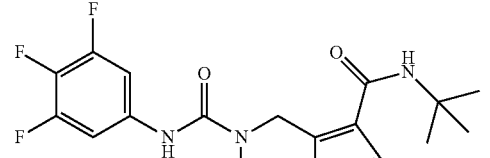<br>42<br>(R)-N³-(Tert-butyl)-6-methyl-N⁵-(3,4,5-trifluorophenyl)-6,7-dihydropyrazolo[1,5-a]pyrazine-3,5(4H)-dicarboxamide 42 |
| 43 | 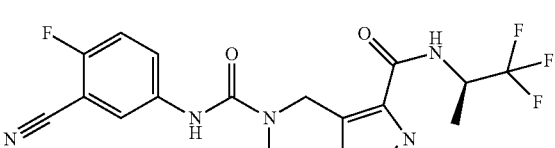<br>43 |

| Example No. | Structure and name of the compound |
|---|---|
| | (R)-N⁷-(3-Cyano-4-fluorophenyl)-6-methyl-N¹-((R)-1,1,1-trifluoropropan-2-yl)-5,6-dihydroimidazo[1,5-a]pyrazine-1,7(8H)-dicarboxamide 43 |
| 44 | 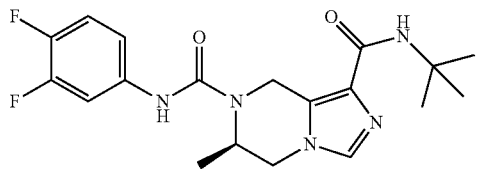

44

(R)-N¹-(Tert-butyl)-N⁷-(3,4-difluorophenyl)-6-methyl-5,6-dihydroimidazo[1,5-a]pyrazine-1,7(8H)-dicarboxamide 44 |
| 45 | 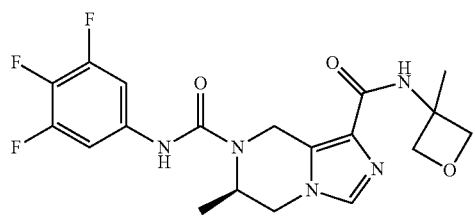

45

(R)-6-Methyl-N¹-(3-methyloxetan-3-yl)-N⁷-(3,4,5-trifluorophenyl)-5,6-dihydroimidazo[1,5-a]pyrazine-1,7(8H)-dicarboxamide 45 |
| 46 | 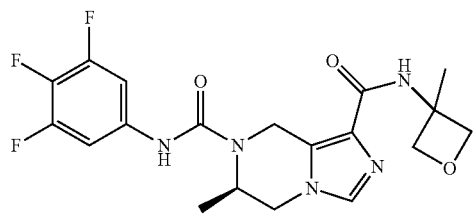

46

(R)-6-Methyl-N³-(3-methyloxetan-3-yl)-N⁵-(3,4,5-trifluorophenyl)-6,7-dihydropyrazolo[1,5-a]pyrazine-3,5(4H)-dicarboxamide 46 |
| 47 | 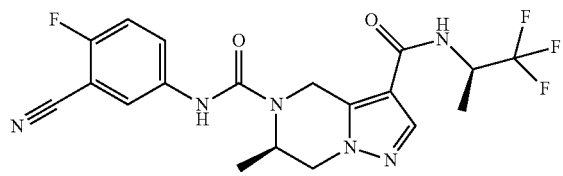

47

(R)-N⁵-(3-Cyano-4-fluorophenyl)-6-methyl-N³-((R)-1,1,1-trifluoropropan-2-yl)-6,7-dihydropyrazolo[1,5-a]pyrazine-3,5(4H)-dicarboxamide 47 |
| 48 | 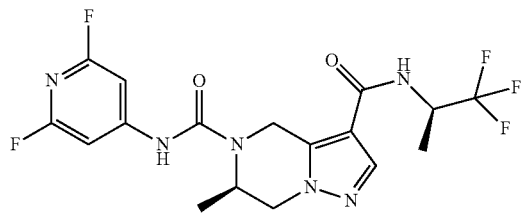

48

(R)-N⁵-(2,6-Difluoropyridin-4-yl)-6-methyl-N3-((R)-1,1,1-trifluoropropan-2-yl)-6,7-dihydropyrazolo[1,5-a]pyrazine-3,5(4H)-dicarboxamide 48 |

-continued

| Example No. | Structure and name of the compound |
|---|---|
| 49 | 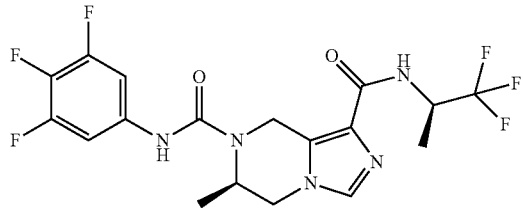

49

(R)-6-Methyl-N[7]-(3,4,5-trifluorophenyl)-N[1]-((R)-1,1,1-trifluoropropan-2-yl)-5,6-dihydroimidazo[1,5-a]pyrazine-1,7(8H)-dicarboxamide 49 |
| 50 | 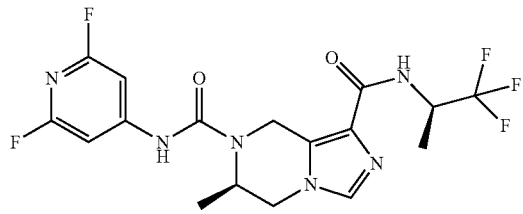

50

(R)-N[7]-(2,6-Difluoropyridin-4-yl)-6-methyl-N[1]-((R)-1,1,1-trifluoropropan-2-yl)-5,6-dihydroimidazo[1,5-a]pyrazine-1,7(8H)-dicarboxamide 50 |
| 51 | 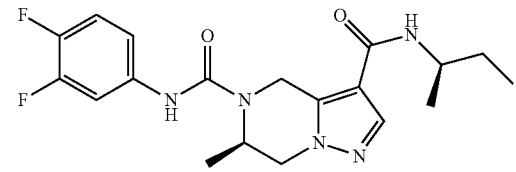

51

(R)-N[3]-((R)-Sec-butyl)-N[5]-(3,4-difluorophenyl)-6-methyl-6,7-dihydropyrazolo[1,5-a]pyrazine-3,5(4H)-dicarboxamide 51 |
| 52 | 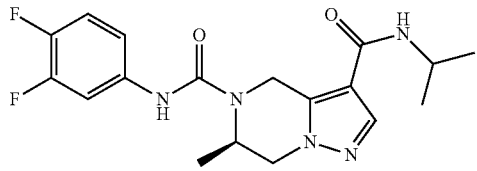

52

(R)-N[5]-(3,4-Difluorophenyl)-N[3]-isopropyl-6-methyl-6,7-dihydropyrazolo[1,5-a]pyrazine-3,5(4H)-dicarboxamide 52 |
| 53 | 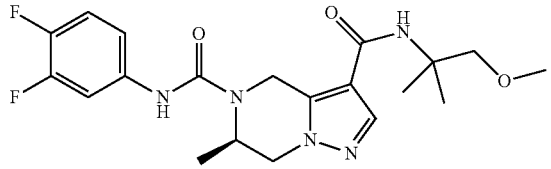

53

(R)-N[5]-(3,4-Difluorophenyl)-N[3]-(1-methoxy-2-methylpropan-2-yl)-6-methyl-6,7-dihydropyrazolo[1,5-a]pyrazine-3,5(4H)-dicarboxamide 53 |

| Example No. | Structure and name of the compound |
|---|---|
| 54 | 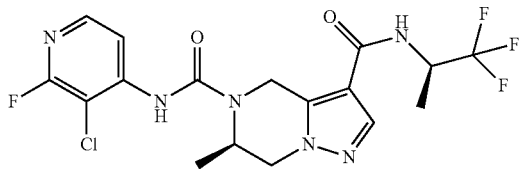

54

(R)-$N^5$-(3-Chloro-2-fluoropyridin-4-yl)-6-methyl-$N^3$-((R)-1,1,1-trifluoropropan-2-yl)-6,7-dihydropyrazolo[1,5-a]pyrazine-3,5(4H)-dicarboxamide 54 |
| 55 | 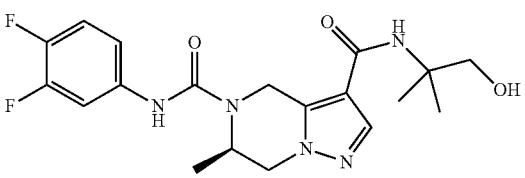

55

(R)-$N^5$-(3,4-Difluorophenyl)-$N^3$-(1-hydroxy-2-methylpropan-2-yl)-6-methyl-6,7-dihydropyrazolo[1,5-a]pyrazine-3,5(47H)-dicarboxamide 55 |
| 56 | 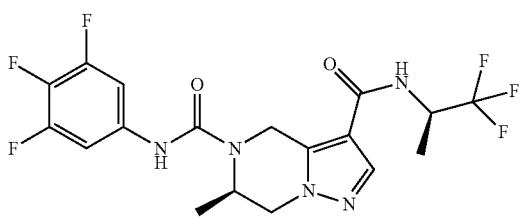

56

(R)-6-Methyl-$N^5$-(3,4,5-trifluorophenyl)-$N^3$-((R)-1,1,1-trifluoropropan-2-yl)-6,7-dihydropyrazolo[1,5-a]pyrazine-3,5(4H)-dicarboxamide 56 |
| 57 | 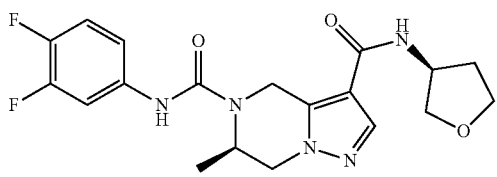

57

(R)-$N^5$-(3,4-Difluorophenyl)-6-methyl-$N^3$-((S)-tetrahydrofuran-3-yl)-6,7-dihydropyrazolo[1,5-a]pyrazine-3,5(4H)-dicarboxamide 57 |
| 58 | 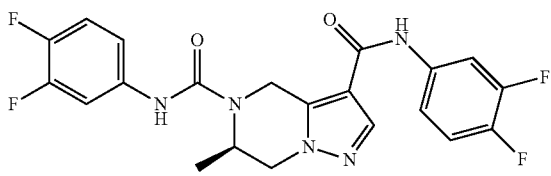

58

(R)-$N^3$,$N^5$-Bis(3,4-difluorophenyl)-6-methyl-6,7-dihydropyrazolo[1,5-a]pyrazine-3,5(4H)-dicarboxamide 58 | or a tautomer, mesomer, racemate, enantiomer, diastereomer thereof, or mixture thereof,
or a pharmaceutically acceptable salt thereof.

In another aspect, the present invention provides a compound of formula (IA):

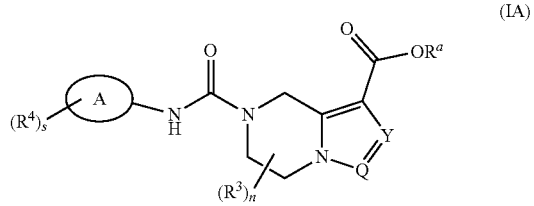

(IA)

or a tautomer, mesomer, racemate, enantiomer, diastereomer thereof, or mixture thereof,
or a pharmaceutically acceptable salt thereof,
wherein:
$R^a$ is hydrogen or alkyl;
ring A is aryl or heteroaryl;
Y is N or $CR^5$;
Q is N or CH;
each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl;
each $R^4$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$;
$R^5$ is selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl and heteroaryl;
$R^6$ is selected from the group consisting of hydrogen, alkyl, haloalkyl, amino, hydroxy, hydroxyalkyl, cycloalkyl, heterocyclyl, aryl and heteroaryl;
n is 0, 1, 2 or 3;
m is 0, 1 or 2; and
s is 0, 1, 2, 3 or 4.

In another aspect, the present invention provides a compound of formula (IC):

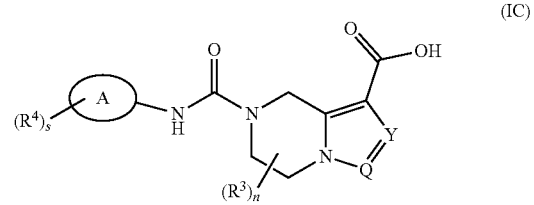

(IC)

or a tautomer, mesomer, racemate, enantiomer, diastereomer thereof, or mixture thereof,
or a pharmaceutically acceptable salt thereof,
wherein:
ring A is aryl or heteroaryl;
Y is N or $CR^5$;
Q is N or CH;
each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl;
each $R^4$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$;
$R^5$ is selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl and heteroaryl;
$R^6$ is selected from the group consisting of hydrogen, alkyl, haloalkyl, amino, hydroxy, hydroxyalkyl, cycloalkyl, heterocyclyl, aryl and heteroaryl;
n is 0, 1, 2 or 3;
m is 0, 1 or 2; and
s is 0, 1, 2, 3 or 4.

They are intermediates for preparing the compound of formula (I) or a tautomer, mesomer, racemate, enantiomer, diastereomer thereof, or mixture thereof, or a pharmaceutically acceptable salt thereof.

Typical compounds of formula (IA) include, but are not limited to:

| Example No. | Structure and name of the compound |
|---|---|
| 1d | ![structure 1d]<br>1d<br>Methyl 7-((3,4,5-trifluorophenyl)carbamoyl)-5,6,7,8-tetrahydroimidazo[1,5-α]pyrazine-1-carboxylate |
| 2e | ![structure 2e]<br>2e<br>Methyl 5-((3,4-difluorophenyl)carbamoyl)-4,5,6,7-tetrahydropyrazolo[1,5-α]pyrazine-3-carboxylate |
| 4a | ![structure 4a]<br>4a<br>Methyl 5-((3,4,5-trifluorophenyl)carbamoyl)-4,5,6,7-tetrahydropyrazolo[1,5-α]pyrazine-3-carboxylate |

| Example No. | Structure and name of the compound |
|---|---|
| 5b | 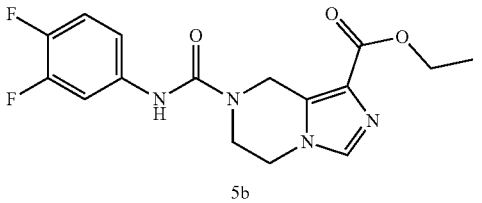 [SMILES: CCOC(=O)c1ncn2c1CN(C(=O)Nc1ccc(F)c(F)c1)CC2]
5b
Ethyl 7-((3,4-difluorophenyl)carbamoyl)-5,6,7,8-tetrahydroimidazo[1,5-α]pyrazine-1-carboxylate |
| 6f | 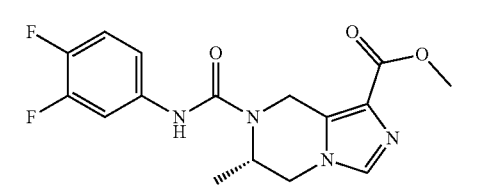
6f
Methyl (S)-7-((3,4-difluorophenyl)carbamoyl)-6-methyl-5,6,7,8-tetrahydroimidazo[1,5-α]pyrazine-1-carboxylate 6f |
| 7e | 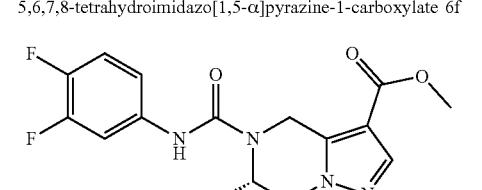
7e
Methyl (S)-5-((3,4-difluorophenyl)carbamoyl)-6-methyl-4,5,6,7-tetrahydropyrazolo[1,5-α]pyrazine-3-carboxylate 7e |
| 7f | 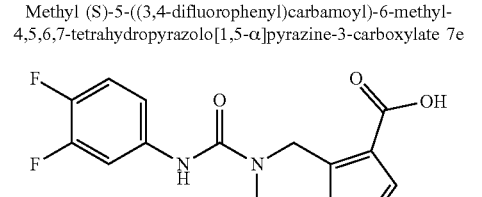
7f
(S)-5-((3,4-Difluorophenyl)carbamoyl)-6-methyl-4,5,6,7-tetrahydropyrazolo[1,5-α]pyrazine-3-carboxylic acid 7f |
| 9a | 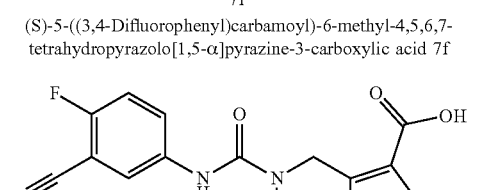
9a
Methyl 5-((3-cyano-4-fluorophenyl)carbamoyl)-4,5,6,7-tetrahydropyrazolo[1,5-α]pyrazine-3-carboxylate 9a |
| 9b | 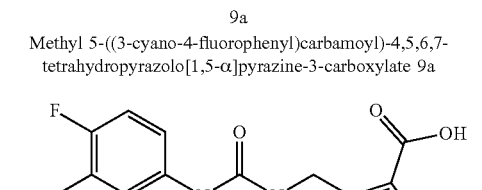
9b
5-((3-Cyano-4-fluorophenyl)carbamoyl)-4,5,6,7-tetrahydropyrazolo[1,5-α]pyrazine-3-carboxylic acid 9b |
| 10a | 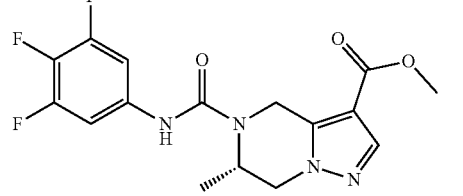
10a
Methyl (S)-6-methyl-5-((3,4,5-trifluorophenyl)carbamoyl)-4,5,6,7-tetrahydropyrazolo[1,5-α]pyrazine-3-carboxylate 10a |
| 10b | 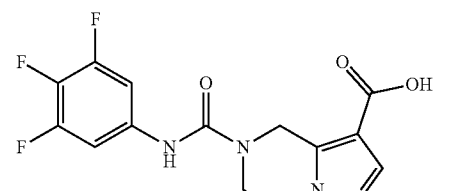
10b
(S)-6-Methyl-5-((3,4,5-trifluorophenyl)carbamoyl)-4,5,6,7-tetrahydropyrazolo[1,5-α]pyrazine-3-carboxylic acid 10b |
| 11a | 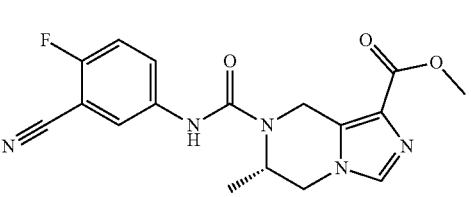
11a
Methyl (S)-7-((3-cyano-4-fluorophenyl)carbamoyl)-6-methyl-5,6,7,8-tetrahydroimidazo[1,5-α]pyrazine-1-carboxylate 11a |
| 11b | 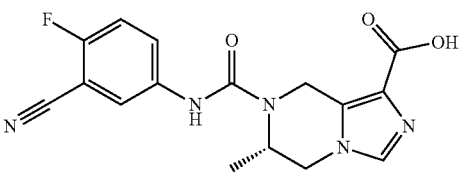
11b
(S)-7-((3-Cyano-4-fluorophenyl)carbamoyl)-6-methyl-5,6,7,8-tetrahydroimidazo[1,5-α]pyrazine-1-carboxylic acid 11b |
| 13a | 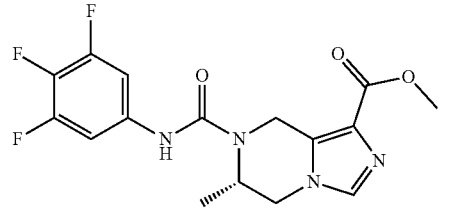
13a
Methyl (S)-6-methyl-7-((3,4,5-trifluorophenyl)carbamoyl)-5,6,7,8-tetrahydroimidazo[1,5-α]pyrazine-1-carboxylate 13a |

| Example No. | Structure and name of the compound |
|---|---|
| 13b | 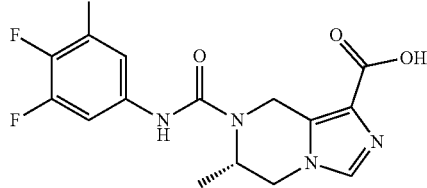<br>13b<br>(S)-6-Methyl-7-((3,4,5-trifluorophenyl)carbamoyl)-5,6,7,8-tetrahydroimidazo[1,5-α]pyrazine-1-carboxylic acid 13b |
| 17e | 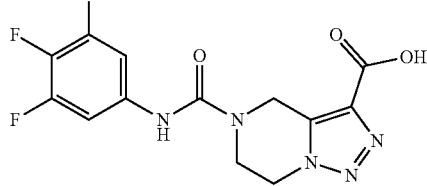<br>17e<br>5-((3,4,5-Trifluorophenyl)carbamoyl)-4,5,6,7-tetrahydro-[1,2,3]triazolo[1,5-α]pyrazine-3-carboxylic acid 17e |
| 19a | 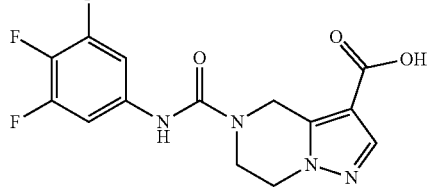<br>19a<br>5-((3,4,5-Trifluorophenyl)carbamoyl)-4,5,6,7-tetrahydro-pyrazolo[1,5-α]pyrazine-3-carboxylic acid 19a |
| 37c | 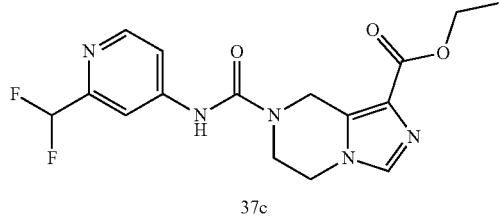 [SMILES: CCOC(=O)c1ncn2c1CN(C(=O)Nc1ccnc(C(F)F)c1)CC2]<br>37c<br>Ethyl 7-((2-(difluoromethyl)pyridin-4-yl)carbamoyl)-5,6,7,8-tetrahydroimidazo[1,5-α]pyrazine-1-carboxylate 37c |
| 45d | 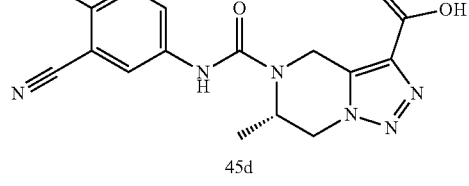<br>45d<br>(S)-5-((3-Cyano-4-fluorophenyl)carbamoyl)-6-methyl-4,5,6,7-tetrahydro-[1,2,3]triazolo[1,5-α]pyrazine-3-carboxylic acid 45d |

In another aspect, the present invention provides a compound of formula (IIIA):

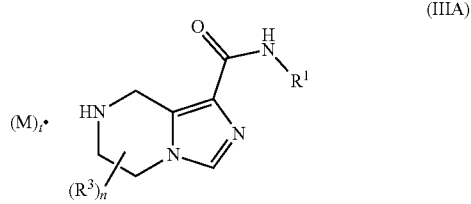

or a tautomer, mesomer, racemate, enantiomer, diastereomer thereof, or mixture thereof,
or a pharmaceutically acceptable salt thereof,
wherein:
M is trifluoroacetic acid or hydrochloric acid;
$R^1$ is selected from the group consisting of alkyl, haloalkyl, hydroxyalkyl, cycloalkyl, heterocyclyl, aryl and heteroaryl, wherein the alkyl, haloalkyl, cycloalkyl, heterocyclyl, aryl and heteroaryl are each independently optionally further substituted by one or more substituents selected from the group consisting of halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl;

t is 0 or 1; and n is 0, 1, 2 or 3.

It is an intermediate for preparing the compound of formula (III) or a tautomer, mesomer, racemate, enantiomer, diastereomer thereof, or mixture thereof, or a pharmaceutically acceptable salt thereof.

Typical intermediate compounds include, but are not limited to:

| Example No. | Structure and name of the compound |
|---|---|
| 3c | 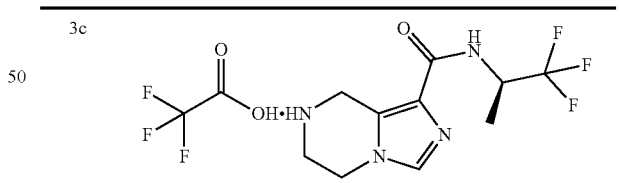<br>3c<br>(R)-N-(1,1,1-Trifluoropropan-2-yl)-5,6,7,8-tetrahydroimidazo[1,5-α]pyrazine-1-carboxamide trifluoroacetate |
| | 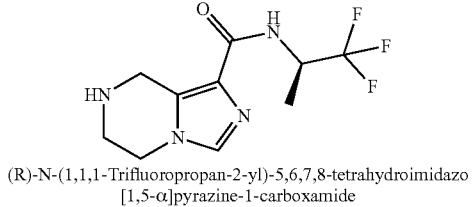<br>(R)-N-(1,1,1-Trifluoropropan-2-yl)-5,6,7,8-tetrahydroimidazo[1,5-α]pyrazine-1-carboxamide |

| Example No. | Structure and name of the compound |
|---|---|
| 15c | 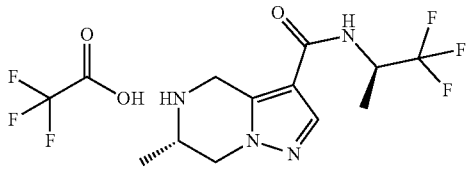<br>15c<br>(S)-6-Methyl-N-((R)-1,1,1-trifluoropropan-2-yl)-4,5,6,7-tetra-hydropyrazolo[1,5-α]pyrazine-3-carboxamide trifluoroacetate 15c |
| | 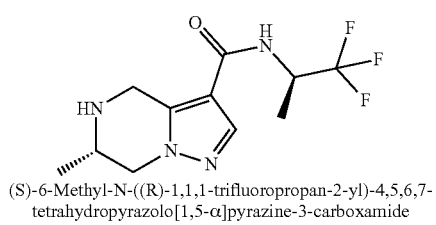<br>(S)-6-Methyl-N-((R)-1,1,1-trifluoropropan-2-yl)-4,5,6,7-tetrahydropyrazolo[1,5-α]pyrazine-3-carboxamide |

In another aspect, the present invention provides a method for preparing the compound of formula (I) according to the present invention, comprising a step of:

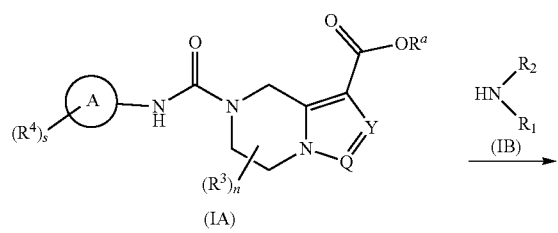

(IA)

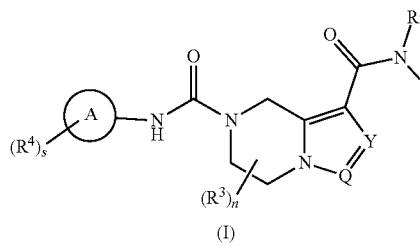

(I)

reacting a compound of formula (IA) with a compound of formula (IB) or a salt thereof to obtain the compound of formula (I), wherein:

$R^a$ is hydrogen or alkyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Y, Q, $R^1$, $R^2$, $R^4$, s and n are as defined in formula (I).

In another aspect, the present invention provides a method for preparing the compound of formula (I) according to the present invention, comprising a step of:

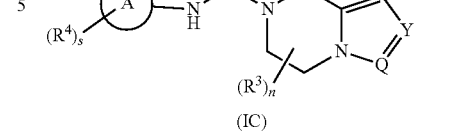

(IC)

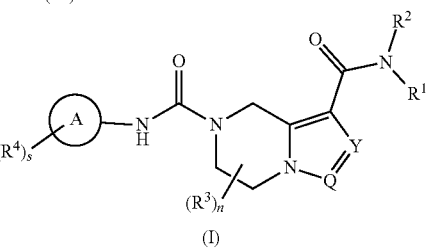

(I)

reacting a compound of formula (IC) with a compound of formula (IB) or a salt thereof to obtain the compound of formula (I), wherein:

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Y, Q, $R^1$, $R^2$, $R^4$, s and n are as defined in formula (I).

In another aspect, the present invention provides a method for preparing the compound of formula (II) according to the present invention, comprising a step of:

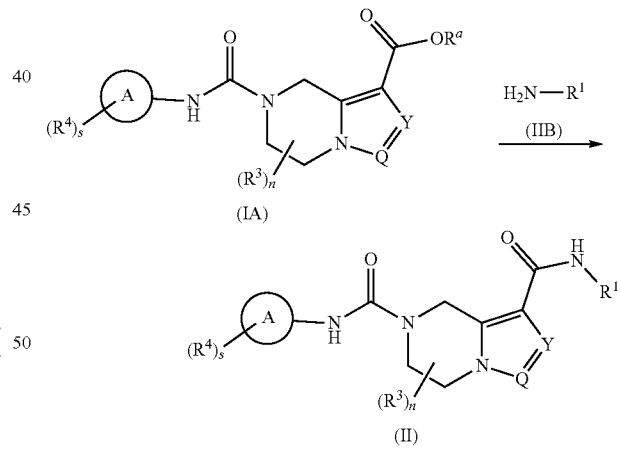

(II)

reacting a compound of formula (IA) with a compound of formula (IIB) or a salt thereof to obtain the compound of formula (II), wherein:

$R^a$ is hydrogen or alkyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Y, Q, $R^1$, $R^4$, s and n are as defined in formula (II).

In another aspect, the present invention provides a method for preparing the compound of formula (II) according to the present invention, comprising a step of:

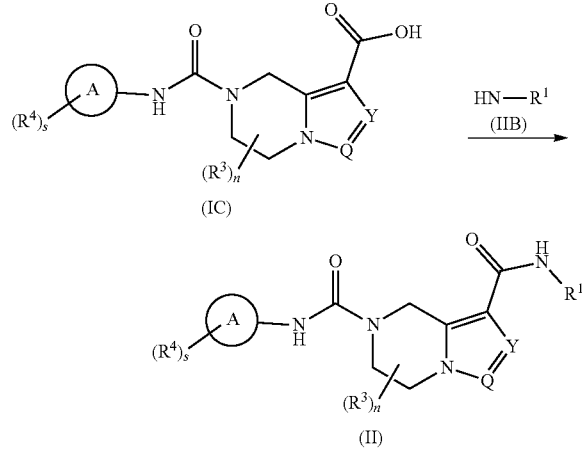

reacting a compound of formula (IC) with a compound of formula (IIB) or a salt thereof to obtain the compound of formula (II), wherein:

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Y, Q, $R^1$, $R^4$, s and n are as defined in formula (II).

In another aspect, the present invention provides a method for preparing the compound of formula (III), formula (IV), formula (V) or formula (VI) according to the present invention, comprising a step of:

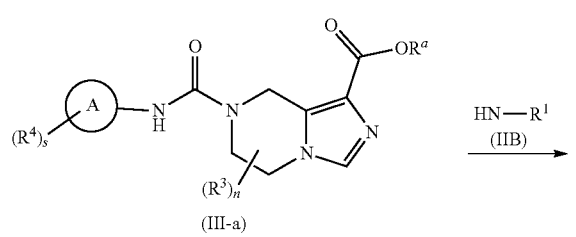

reacting a compound of formula (III-a) with a compound of formula (IIB) or a salt thereof to obtain the compound of formula (III), or

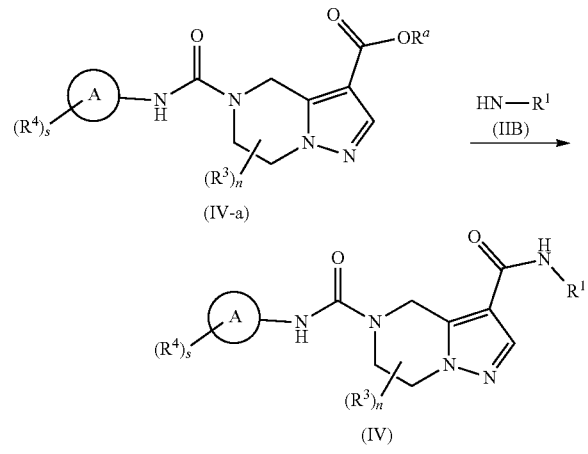

reacting a compound of formula (IV-a) with a compound of formula (IIB) or a salt thereof to obtain the compound of formula (IV),

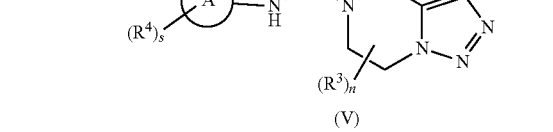

reacting a compound of formula (V-a) with a compound of formula (IIB) or a salt thereof to obtain the compound of formula (V), or

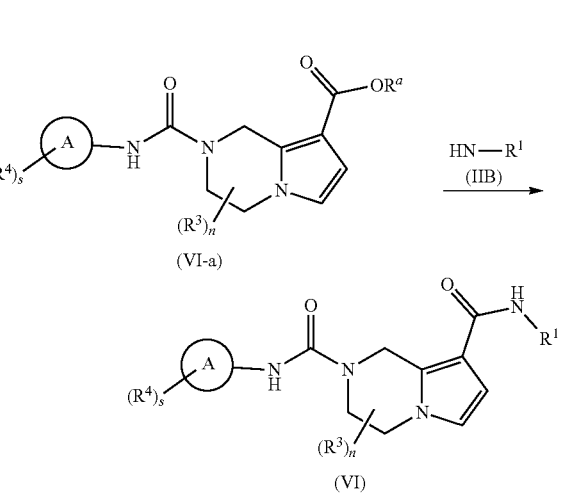

reacting a compound of formula (VI-a) with a compound of formula (IIB) or a salt thereof to obtain the compound of formula (VI), wherein:

$R^a$ is hydrogen or alkyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, $R^1$, $R^4$, s and n are as defined in formula (I).

In another aspect, the present invention provides a method for preparing the compound of formula (III), comprising a step of:

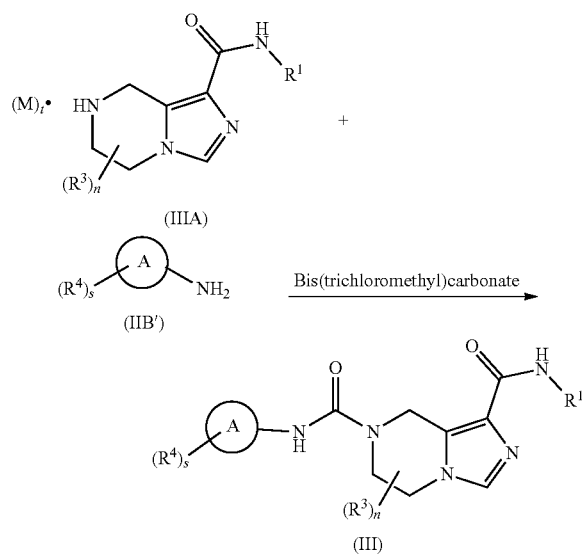

reacting a compound of formula (IIIA) or a salt thereof with a compound of formula (IIB') or a salt thereof and bis(trichloromethyl)carbonate to obtain the compound of formula (III), wherein:

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and M is trifluoroacetic acid or hydrochloric acid;

t is 0 or 1;

ring A, $R^1$, $R^4$, s and n are as defined in formula (III).

In another aspect, the present invention relates to a pharmaceutical composition comprising a therapeutically effective amount of the compound of formula (I), or a tautomer, mesomer, racemate, enantiomer, diastereomer thereof, or mixture thereof, or a pharmaceutically acceptable salt thereof, and one or more pharmaceutically acceptable carrier(s), diluent(s) or excipient(s). The present invention also relates to a method for preparing the above composition, comprising a step of mixing the compound of formula (I), or a tautomer, mesomer, racemate, enantiomer, diastereomer thereof, or mixture thereof, or a pharmaceutically acceptable salt thereof with the pharmaceutically acceptable carrier(s), diluent(s) or excipient(s).

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same in the preparation of a capsid protein inhibitor.

The present invention further relates to a use of the compound of formula (I), or a tautomer, mesomer, racemate, enantiomer, diastereomer thereof, or mixture thereof, or a pharmaceutically acceptable salt thereof, or the pharmaceutical composition comprising the same in the preparation of a medicament for preventing and/or treating a viral infection disease. The virus can be hepatitis B virus, influenza virus, herpes virus and AIDS virus, and the diseases can be hepatitis B, influenza, herpes and AIDS.

The present invention further relates to the compound of formula (I), or a tautomer, mesomer, racemate, enantiomer, diastereomer thereof, or mixture thereof, or a pharmaceutically acceptable salt thereof, for use as a medicament. The medicament is preferably a medicament for preventing and/or treating a viral infection disease. The virus can be hepatitis B virus, influenza virus, herpes virus and AIDS virus, and the diseases can be hepatitis B, influenza, herpes and AIDS.

The present invention also relates to the compound of formula (I), or a tautomer, mesomer, racemate, enantiomer, diastereomer thereof, or mixture thereof, or a pharmaceutically acceptable salt thereof, or the pharmaceutical composition comprising the same, for use as a capsid protein inhibitor.

The present invention also relates to a method for preventing and/or treating a viral infection disease, comprising a step of administrating to a patient in need thereof a therapeutically effective dose of the compound of formula (I), or a tautomer, mesomer, racemate, enantiomer, diastereomer thereof, or mixture thereof, or a pharmaceutically acceptable salt thereof, or the pharmaceutical composition comprising the same as a capsid protein inhibitor. The virus can be hepatitis B virus, influenza virus, herpes virus and AIDS virus, and the diseases can be hepatitis B, influenza, herpes and AIDS.

The pharmaceutical composition containing the active ingredient can be in a form suitable for oral administration, for example, a tablet, troche, lozenge, aqueous or oily suspension, dispersible powder or granule, emulsion, hard or soft capsule, syrup or elixir.

An oral composition can be prepared according to any known method in the art for the preparation of pharmaceutical composition. Such a composition can contain one or more ingredients selected from the group consisting of sweeteners, flavoring agents, colorants and preservatives, in order to provide a pleasing and palatable pharmaceutical formulation. The tablet contains the active ingredient in admixture with nontoxic, pharmaceutically acceptable excipients suitable for the manufacture of tablets. These excipients can be inert excipients, granulating agents, disintegrating agents, binders and lubricants. The tablet can be uncoated or coated by means of a known technique to mask drug taste or delay the disintegration and absorption of the active ingredient in the gastrointestinal tract, thereby providing sustained release over a long period of time.

An oral formulation can also be provided as soft gelatin capsules in which the active ingredient is mixed with an inert solid diluent, or the active ingredient is mixed with a water-soluble carrier or an oil medium.

An aqueous suspension contains the active ingredient in admixture with excipients suitable for the manufacture of an aqueous suspension. Such excipients are suspending agents, dispersants or wetting agents. The aqueous suspension can also contain one or more preservatives, one or more colorants, one or more flavoring agents, and one or more sweeteners.

An oil suspension can be formulated by suspending the active ingredient in a vegetable oil or mineral oil. The oil suspension can contain a thickener. The aforementioned sweeteners and flavoring agents can be added to provide a palatable formulation. These compositions can be preserved by adding an antioxidant.

The pharmaceutical composition of the present invention can also be in the form of an oil-in-water emulsion. The oil phase can be a vegetable oil, or a mineral oil, or a mixture thereof. Suitable emulsifying agents can be naturally occurring phospholipids. The emulsion can also contain a sweetening agent, flavoring agent, preservative and antioxidant. Such a formulation can also contain a demulcent, preservative, colorant and antioxidant.

The pharmaceutical composition of the present invention can be in the form of a sterile injectable aqueous solution. Acceptable vehicles or solvents that can be used are water, Ringer's solution or isotonic sodium chloride solution. The sterile injectable formulation can be a sterile injectable oil-in-water micro-emulsion in which the active ingredient is dissolved in the oil phase. The injectable solution or micro-emulsion can be introduced into a patient's bloodstream by local bolus injection. Alternatively, the solution and micro-emulsion are preferably administrated in a manner that maintains a constant circulating concentration of the compound of the present invention. In order to maintain this constant concentration, a continuous intravenous delivery device can be used. An example of such a device is Deltec CADD-PLUS™ 5400 intravenous injection pump.

The pharmaceutical composition of the present invention can be in the form of a sterile injectable aqueous or oily suspension for intramuscular and subcutaneous administration. Such a suspension can be formulated with suitable dispersants or wetting agents and suspending agents as described above according to known techniques. The sterile injectable formulation can also be a sterile injectable solution or suspension prepared in a nontoxic parenterally acceptable diluent or solvent. Moreover, sterile fixed oils can easily be used as a solvent or suspending medium. For this purpose, any blended fixed oil can be used. In addition, fatty acids can also be used to prepare injections.

The compound of the present invention can be administrated in the form of a suppository for rectal administration. These pharmaceutical compositions can be prepared by mixing the drug with a suitable non-irritating excipient that is solid at ordinary temperatures, but liquid in the rectum, thereby melting in the rectum to release the drug.

It is well known to those skilled in the art that the dosage of a drug depends on a variety of factors including but not limited to, the following factors: activity of a specific compound, age of the patient, weight of the patient, general health of the patient, behavior of the patient, diet of the patient, administration time, administration route, excretion rate, drug combination and the like. In addition, the optimal treatment, such as treatment mode, daily dose of the compound of the present invention or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

The term "alkyl" refers to a saturated aliphatic hydrocarbon group, which is a straight or branched chain group comprising 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various branched isomers thereof. More preferably, the alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy, alkoxycarbonyl, —OR$^6$, —C(O)R$^6$, —C(O)OR$^6$ and —S(O)$_m$R$^6$.

The term "alkoxy" refers to an —O-(alkyl) or an —O-(unsubstituted cycloalkyl) group, wherein the alkyl and cycloalkyl are as defined above. Non-limiting examples of alkoxy include methoxy, ethoxy, propoxy, butoxy, cyclopropyloxy, cyclobutyloxy, cyclopentyloxy, cyclohexyloxy. The alkoxy can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy, alkoxycarbonyl, —OR$^6$, —C(O)R$^6$, —C(O)OR$^6$ and —S(O)$_m$R$^6$.

The term "cycloalkyl" refers to a saturated or partially unsaturated monocyclic or polycyclic hydrocarbon substituent group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl and the like. Polycyclic cycloalkyl includes a cycloalkyl having a spiro ring, fused ring or bridged ring.

The term "spiro cycloalkyl" refers to a 5 to 20 membered polycyclic group with individual rings connected through one shared carbon atom (called a spiro atom), wherein the rings can contain one or more double bonds, but none of the rings has a completely conjugated π-electron system. The spiro cycloalkyl is preferably 6 to 14 membered spiro cycloalkyl, and more preferably 7 to 10 membered spiro cycloalkyl. According to the number of the spiro atoms shared between the rings, the spiro cycloalkyl can be divided into mono-spiro cycloalkyl, di-spiro cycloalkyl, or poly-spiro cycloalkyl, and the spiro cycloalkyl is preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyl include:

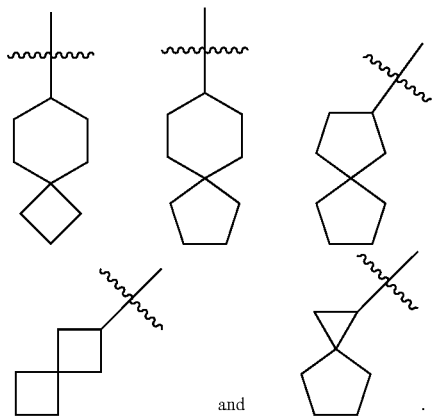

The term "fused cycloalkyl" refers to a 5 to 20 membered all-carbon polycyclic group, wherein each ring in the system shares an adjacent pair of carbon atoms with another ring, wherein one or more rings can contain one or more double bonds, but none of the rings has a completely conjugated π-electron system. The fused cycloalkyl is preferably 6 to 14 membered fused cycloalkyl, and more preferably 7 to 10 membered fused cycloalkyl. According to the number of membered rings, the fused cycloalkyl can be divided into bicyclic, tricyclic, tetracyclic or polycyclic fused cycloalkyl, and the fused cycloalkyl is preferably bicyclic or tricyclic fused cycloalkyl, and more preferably 5-membered/5-membered, or 5-membered/6-membered bicyclic fused cycloalkyl. Non-limiting examples of fused cycloalkyl include:

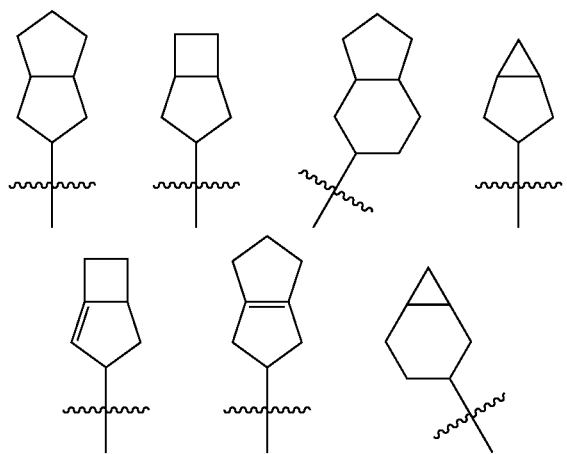

-continued

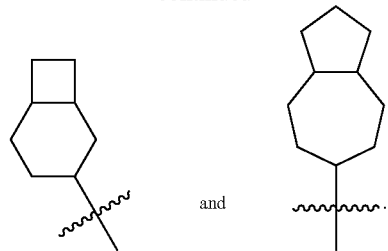

The term "bridged cycloalkyl" refers to a 5 to 20 membered all-carbon polycyclic group, wherein every two rings in the system share two disconnected carbon atoms, wherein the rings can have one or more double bonds, but none of the rings has a completely conjugated π-electron system. The bridged cycloalkyl is preferably 6 to 14 membered bridged cycloalkyl, and more preferably 7 to 10 membered bridged cycloalkyl. According to the number of membered rings, the bridged cycloalkyl can be divided into bicyclic, tricyclic, tetracyclic or polycyclic bridged cycloalkyl, and the bridged cycloalkyl is preferably bicyclic, tricyclic or tetracyclic bridged cycloalkyl, and more preferably bicyclic or tricyclic bridged cycloalkyl. Non-limiting examples of bridged cycloalkyl include:

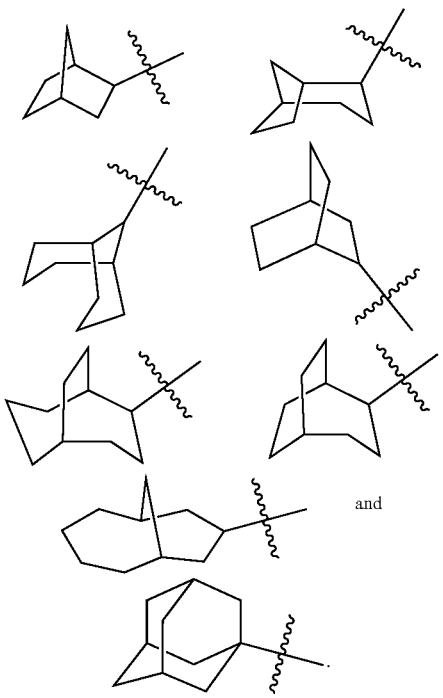

The cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy, alkoxycarbonyl, —OR$^6$, —C(O)R$^6$, —C(O)OR$^6$ and —S(O)$_m$R$^6$.

The term "heterocyclyl" refers to a 3 to 20 membered saturated or partially unsaturated monocyclic or polycyclic hydrocarbon group, wherein one or more ring atoms are heteroatoms selected from the group consisting of N, O and S(O)$_m$ (wherein m is an integer of 0 to 2), but excluding —O—O—, —O—S— or —S—S— in the ring, with the remaining ring atoms being carbon atoms. Preferably, the heterocyclyl has 3 to 12 ring atoms wherein 1 to 4 atoms are heteroatoms; more preferably, 3 to 8 ring atoms wherein 1 to 3 atoms are heteroatoms; and most preferably 3 to 6 ring atoms wherein 1 to 2 atoms are heteroatoms. Non-limiting examples of monocyclic heterocyclyl include pyrrolidinyl, imidazolidinyl, tetrahydrofuranyl, tetrahydrothienyl, dihydroimidazolyl, dihydrofuranyl, dihydropyrazolyl, dihydropyrrolyl, piperidinyl, piperazinyl, morpholinyl, thiomorpholinyl, homopiperazinyl, pyranyl and the like, and preferably piperidinyl, piperazinyl or morpholinyl. Polycyclic heterocyclyl includes aheterocyclyl having a spiro ring, fused ring or bridged ring.

The term "spiro heterocyclyl" refers to a 5 to 20 membered polycyclic heterocyclyl group with individual rings connected through one shared atom (called a spiro atom), wherein one or more ring atoms are heteroatoms selected from the group consisting of N, O and S(O)$_m$ (wherein m is an integer of 0 to 2), with the remaining ring atoms being carbon atoms, where the rings can contain one or more double bonds, but none of the rings has a completely conjugated π-electron system. The spiro heterocyclyl is preferably 6 to 14 membered spiro heterocyclyl, and more preferably 7 to 10 membered spiro heterocyclyl. According to the number of the spiro atoms shared between the rings, the spiro heterocyclyl can be divided into mono-spiro heterocyclyl, di-spiro heterocyclyl, or poly-spiro heterocyclyl, and the spiro heterocyclyl is preferably mono-spiro heterocyclyl or di-spiro heterocyclyl, and more preferably 3-membered/6-membered, 4-membered/4-membered, 4-membered/5-membered, 4-membered/6-membered, 5-membered/5-membered, or 5-membered/6-membered mono-spiro heterocyclyl. Non-limiting examples of spiro heterocyclyl include:

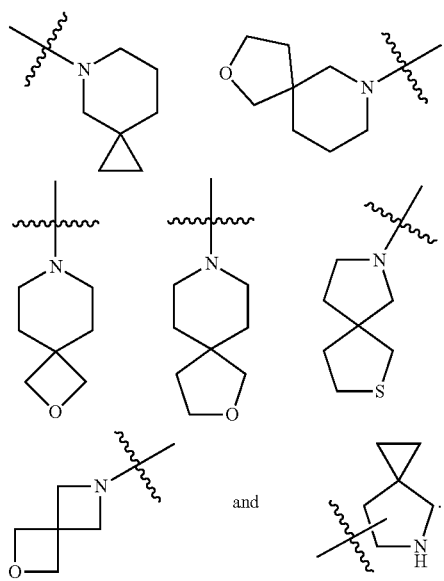

The term "fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated π-electron system, and wherein one or more ring atoms are heteroatoms selected from the group consisting of N, O and S(O)$_m$ (wherein m is an integer of 0 to 2), with the remaining ring atoms being carbon atoms. The fused heterocyclyl is preferably 6 to 14 membered fused heterocyclyl, and more preferably 7 to 10 membered fused heterocyclyl. According to the number of membered rings, the fused heterocyclyl can be divided into bicyclic, tricyclic, tetracyclic or polycyclic fused heterocyclyl, and the fused heterocyclyl is preferably bicyclic or tricyclic fused heterocyclyl, and more preferably 5-membered/5-membered or 5-membered/6-membered bicyclic fused heterocyclyl. Non-limiting examples of fused heterocyclyl include:

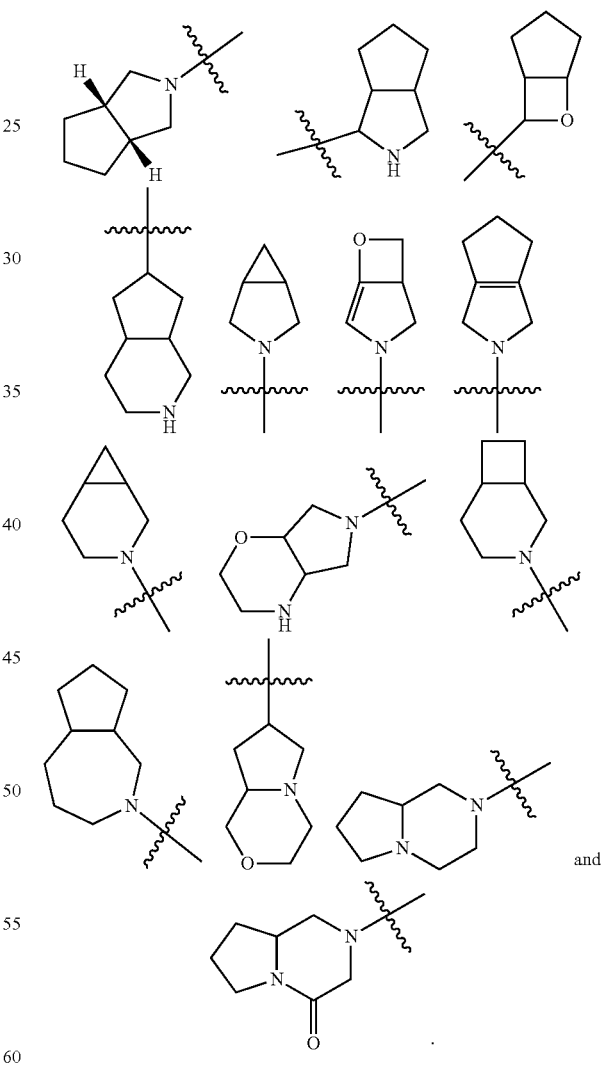

and

The term "bridged heterocyclyl" refers to a 5 to 14 membered polycyclic heterocyclyl group, wherein every two rings in the system share two disconnected atoms, wherein the rings can have one or more double bonds, but none of the rings has a completely conjugated π-electron system, and wherein one or more ring atoms are heteroatoms selected from the group consisting of N, O and S(O)$_m$ (wherein m is an integer of 0 to 2), with the remaining ring atoms being carbon atoms. The bridged heterocyclyl is preferably 6 to 14 membered bridged heterocyclyl, and more preferably 7 to 10 membered bridged heterocyclyl. According to the number of membered rings, the bridged heterocyclyl can be divided into bicyclic, tricyclic, tetracyclic or polycyclic bridged heterocyclyl, and the bridged heterocyclyl is preferably bicyclic, tricyclic or tetracyclic bridged heterocyclyl, and more preferably bicyclic or tricyclic bridged heterocyclyl. Non-limiting examples of bridged heterocyclyl include:

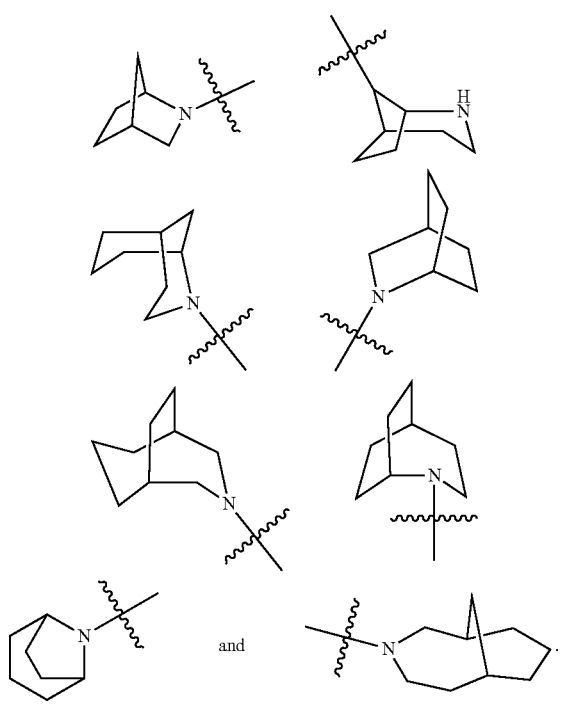

The heterocyclyl ring can be fused to the ring of aryl, heteroaryl or cycloalkyl, wherein the ring bound to the parent structure is heterocyclyl. Non-limiting examples thereof include:

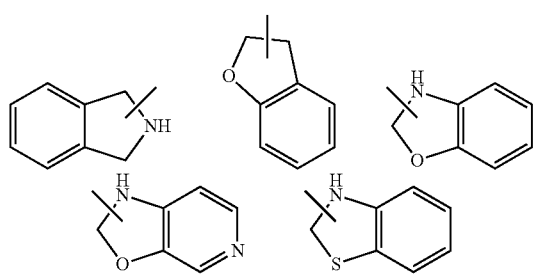

and the like.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, oxo, carboxy, alkoxycarbonyl, —OR$^6$, —C(O)R$^6$, —C(O)OR$^6$ and —S(O)$_m$R$^6$.

The term "aryl" refers to a 6 to 14 membered all-carbon monocyclic ring or polycyclic fused ring (i.e. each ring in the system shares an adjacent pair of carbon atoms with another ring in the system) having a conjugated π-electron system, preferably 6 to 10 membered aryl, for example, phenyl and naphthyl. The aryl is more preferably phenyl. The aryl ring can be fused to the ring of heteroaryl, heterocyclyl or cycloalkyl, wherein the ring bound to the parent structure is aryl ring. Non-limiting examples thereof include:

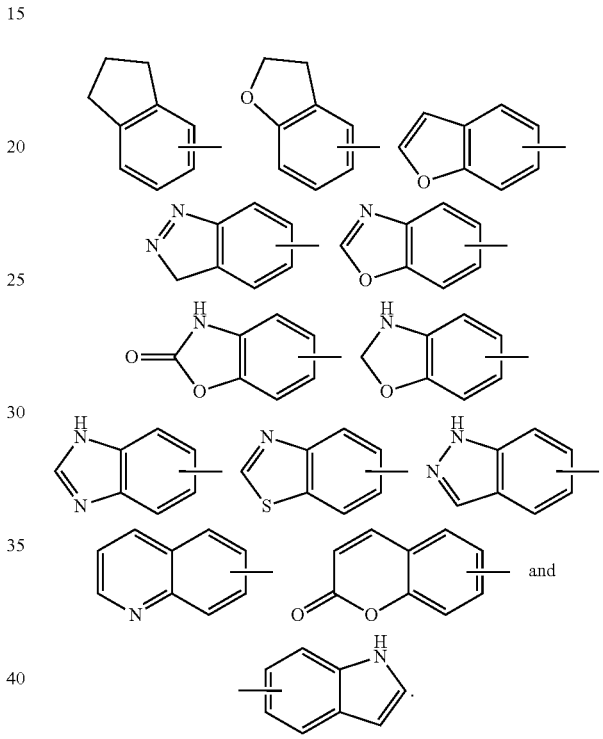

The aryl can be substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy and alkoxycarbonyl.

The term "heteroaryl" refers to a 5 to 14 membered heteroaromatic system having 1 to 4 heteroatoms selected from the group consisting of O, S and N. The heteroaryl is preferably 5 to 10 membered heteroaryl having 1 to 3 heteroatoms, more preferably 5 or 6 membered heteroaryl having 1 to 2 heteroatoms; preferably for example, imidazolyl, furyl, thienyl, thiazolyl, pyrazolyl, oxazolyl, pyrrolyl, tetrazolyl, pyridyl, pyrimidinyl, thiadiazolyl, pyrazinyl and the like, preferably imidazolyl, tetrazolyl, pyridyl, thienyl, pyrazolyl, pyrimidinyl, thiazolyl, and more preferably pyridyl. The heteroaryl ring can be fused to the ring of aryl, heterocyclyl or cycloalkyl, wherein the ring bound to the parent structure is heteroaryl ring. Non-limiting examples thereof include:

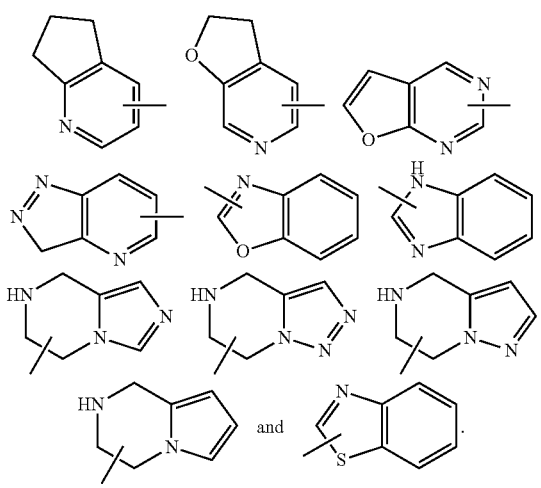

The heteroaryl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocycloalkoxy, cycloalkylthio, heterocyclylthio, carboxy, alkoxycarbonyl, —$OR^6$, —$C(O)R^6$, —$C(O)OR^6$ and —$S(O)_m R^6$.

The term "amino protecting group" refers to a group which prevents an amino group from reaction when other parts of the molecular are subject to a reaction, and can be easily removed. Non-limiting examples include tert-butoxycarbonyl, acetyl, benzyl, allyl, p-methoxybenzyl and the like. These groups can be optionally substituted by one to three substituents selected from the group consisting of halogen, alkoxy and nitro. The amino protecting group is preferably p-methoxybenzyl.

The term "haloalkyl" refers to an alkyl group substituted by one or more halogens, wherein the alkyl is as defined above.

The term "haloalkoxy" refers to an alkoxy group substituted by one or more halogens, wherein the alkoxy is as defined above.

The term "hydroxyalkyl" refers to an alkyl group substituted by hydroxy(s), wherein the alkyl is as defined above.

The term "hydroxy" refers to an —OH group.

The term "halogen" refers to fluorine, chlorine, bromine or iodine.

The term "amino" refers to a —$NH_2$ group.

The term "cyano" refers to a —CN group.

The term "nitro" refers to a —$NO_2$ group.

The term "oxo" refers to a =O group.

The term "carbonyl" refers to a C=O group.

The term "carboxy" refers to a —C(O)OH group.

The term "alkoxycarbonyl" refers to a —C(O)O(alkyl) or —C(O)O(cycloalkyl) group, wherein the alkyl and cycloalkyl are as defined above.

The term "acyl halide" refers to a compound containing a —C(O)-halogen group.

"Optional" or "optionally" means that the event or circumstance described subsequently can, but need not, occur, and such a description includes the situation in which the event or circumstance does or does not occur. For example, "the heterocyclyl optionally substituted by an alkyl" means that an alkyl group can be, but need not be, present, and such a description includes the situation of the heterocyclyl being substituted by an alkyl and the heterocyclyl being not substituted by an alkyl.

"Substituted" refers to one or more hydrogen atoms in a group, preferably up to 5, and more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) may be unstable.

A "pharmaceutical composition" refers to a mixture of one or more of the compounds described herein or physiologically/pharmaceutically acceptable salts or prodrugs thereof with other chemical components, and other components such as physiologically/pharmaceutically acceptable carriers and excipients. The purpose of the pharmaceutical composition is to facilitate administration of a compound to an organism, which is conducive to the absorption of the active ingredient so as to show biological activity.

A "pharmaceutically acceptable salt" refers to a salt of the compound of the present invention, which is safe and effective in mammals and has the desired biological activity.

$R^6$ and m are as defined in formula (I).

Synthesis Method of the Compound of the Present Invention

In order to achieve the object of the present invention, the present invention applies the following technical solutions:

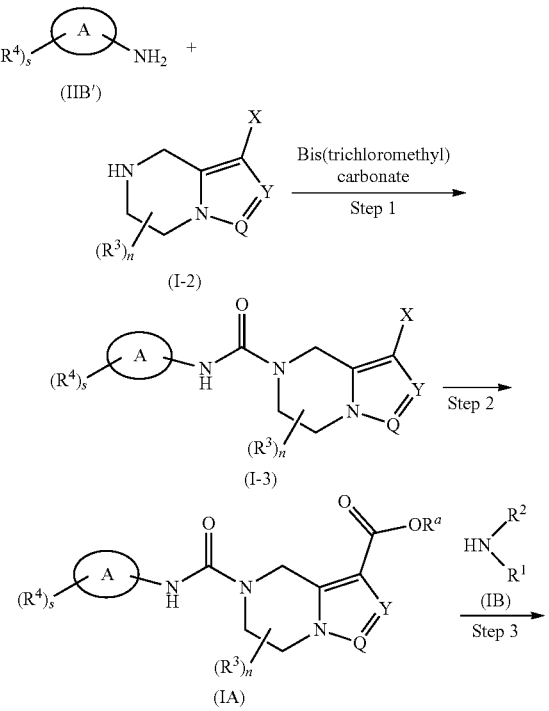

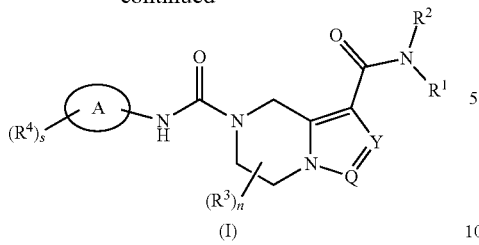

(I)

A method for preparing the compound of formula (I) of the present invention or a tautomer, mesomer, racemate, enantiomer, diastereomer thereof, or mixture thereof, or a pharmaceutically acceptable salt thereof, comprises the following steps of:

in Step 1, a compound of formula (IIB') is reacted with a compound of formula (I-2) and bis(trichloromethyl)carbonate under an alkaline condition to obtain a compound of formula (I-3);

in Step 2, the compound of formula (I-3) is reacted with carbon monoxide in the presence of a catalyst under an alkaline condition to obtain a compound of formula (IA);

in Step 3, the compound of formula (IA) is reacted with a compound of formula (IB) or a salt thereof to obtain the compound of formula (I).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The catalyst includes, but is not limited to, Pd/C, Raney Ni, platinum dioxide, tetra-triphenylphosphine palladium, palladium dichloride, palladium acetate, 2-dicyclohexylphosphino-2,4,6-triisopropylbiphenyl, [1,1'-bis(diphenylphosphino)ferrocene]dichloropalladium, 1,1'-bis(dibenzylphosphoryl)ferrocene palladium dichloride, tris(dibenzylideneacetone)dipalladium and 2-dicyclohexylphosphino-2',6'-dimethoxybiphenyl, and preferably [1,1'-bis(diphenylphosphino)ferrocene]dichloropalladium and 2-dicyclohexylphosphino-2',6'-dimethoxybiphenyl.

The condensing agent includes, but is not limited to, 1-(3-dimethylaminopropyl)-3-ethylcarbodiimide hydrochloride, N,N-dicyclohexylcarbodiimide, N,N-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is hydrogen or alkyl, and preferably hydrogen, methyl or ethyl;

X is halogen, and preferably bromine;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Y, Q, $R^1$, $R^2$, $R^4$, s and n are as defined in formula (I).

Scheme II

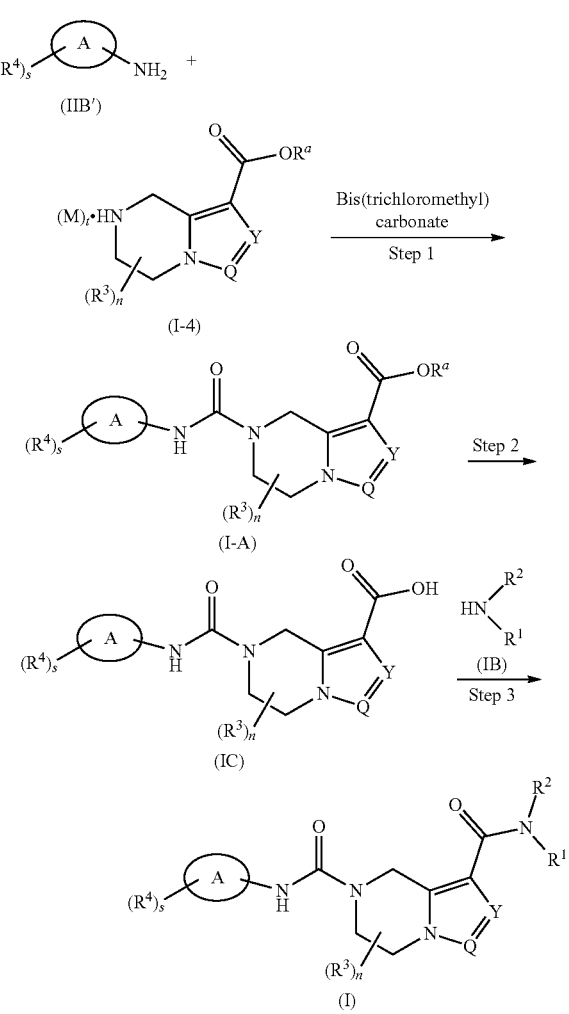

A method for preparing the compound of formula (I) of the present invention or a tautomer, mesomer, racemate, enantiomer, diastereomer thereof, or mixture thereof, or a pharmaceutically acceptable salt thereof, comprises the following steps of:

in Step 1, a compound of formula (IIB') is reacted with a compound of formula (I-4) and bis(trichloromethyl)carbonate under an alkaline condition to obtain a compound of formula (IA);

in Step 2, the compound of formula (IA) is subjected to a hydrolysis reaction under an alkaline condition to obtain a compound of formula (IC);

in Step 3, the compound of formula (IC) and a compound of formula (IB) or a salt thereof are subjected to a condensation reaction to obtain the compound of formula (I).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is alkyl, and preferably methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Y, Q, $R^1$, $R^2$, $R^4$, s and n are as defined in formula (I).

A method for preparing the compound of formula (II) of the present invention or a tautomer, mesomer, racemate, enantiomer, diastereomer thereof, or mixture thereof, or a pharmaceutically acceptable salt thereof, comprises the following step of:

Reacting a compound of formula (IA) with a compound of formula (IIB) or a salt thereof under an alkaline condition to obtain the compound of formula (II).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriaz-ole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is hydrogen or alkyl, and preferably hydrogen, methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Q, Y, $R^1$, $R^4$, s and n are as defined in formula (II).

Scheme III

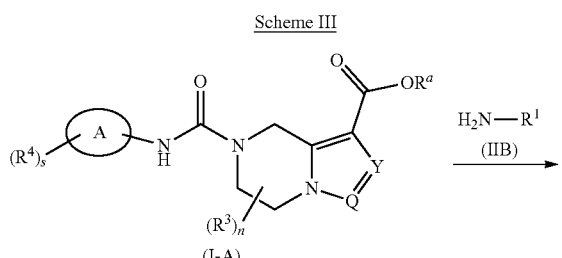

(I-A)

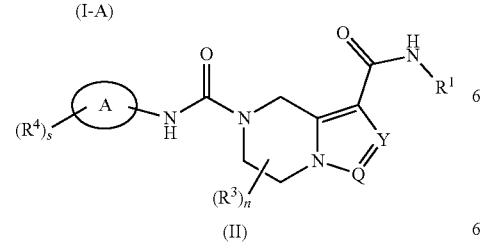

(II)

Scheme IV

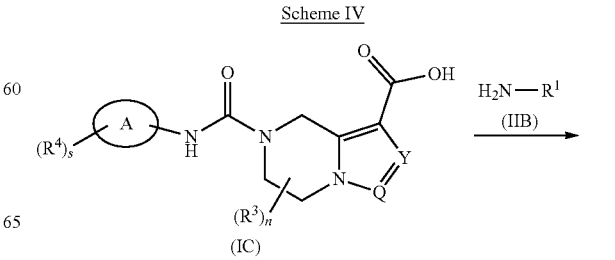

(IC)

-continued

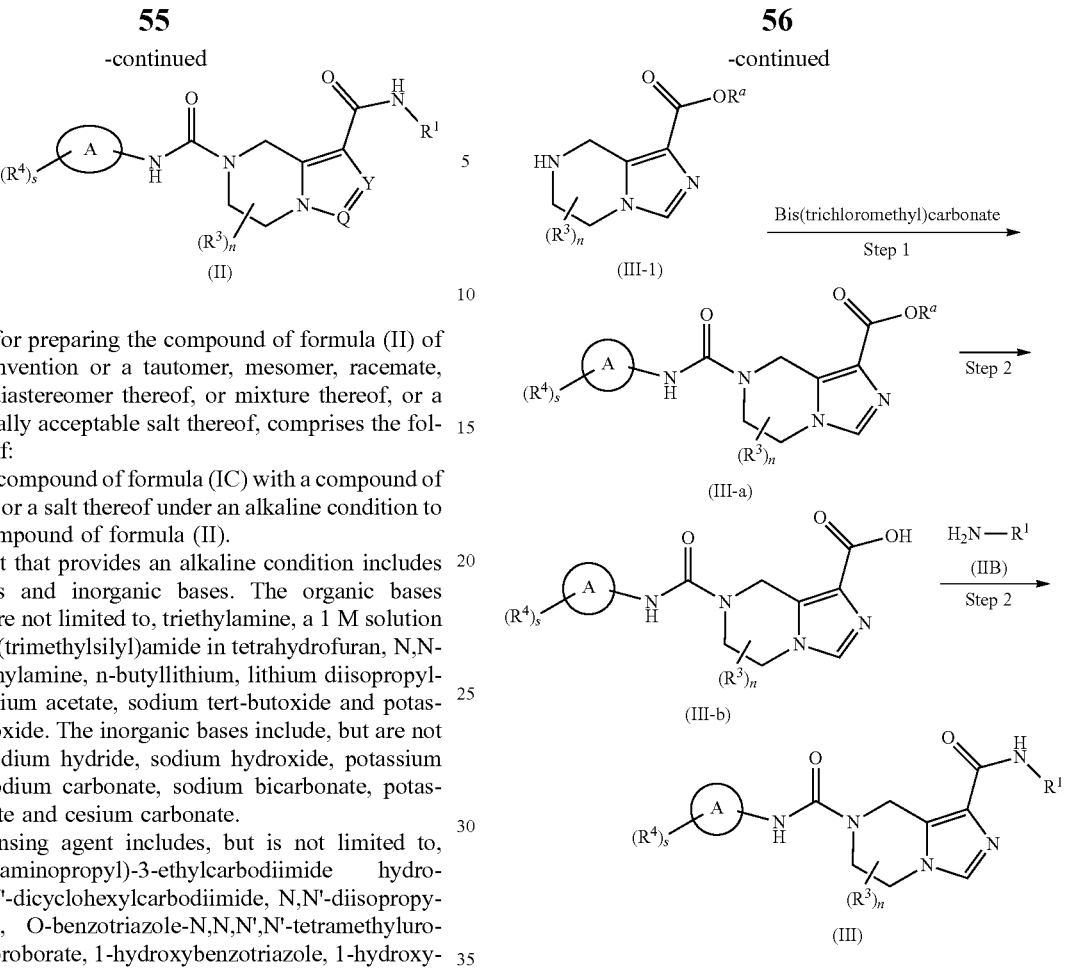

A method for preparing the compound of formula (II) of the present invention or a tautomer, mesomer, racemate, enantiomer, diastereomer thereof, or mixture thereof, or a pharmaceutically acceptable salt thereof, comprises the following step of:

Reacting a compound of formula (IC) with a compound of formula (IIB) or a salt thereof under an alkaline condition to obtain the compound of formula (II).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, Q, Y, $R^1$, $R^4$, s and n are as defined in formula (II).

Scheme V

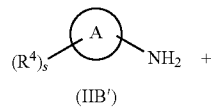

A method for preparing the compound of formula (III) of the present invention or a tautomer, mesomer, racemate, enantiomer, diastereomer thereof, or mixture thereof, or a pharmaceutically acceptable salt thereof, comprises the following steps of:

in Step 1, a compound of formula (IIB') is reacted with a compound of formula (III-1) and bis(trichloromethyl)carbonate under an alkaline condition to obtain a compound of formula (III-a);

in Step 2, the compound of formula (III-a) is subjected to a hydrolysis reaction under an alkaline condition to obtain a compound of formula (III-b);

in Step 3, the compound of formula (III-b) is reacted with a compound of formula (IIB) or a salt thereof to obtain the compound of formula (III).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N'-dicyclohexylcarbodiimide, N,N'-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'- tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is alkyl, and preferably methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, $R^1$, $R^4$, s and n are as defined in formula (III).

Scheme VI

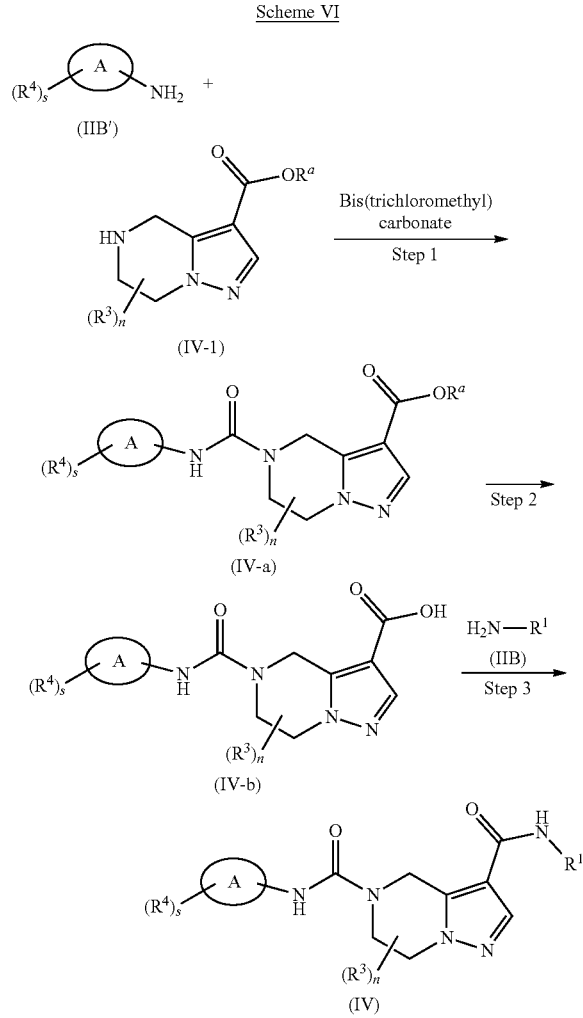

A method for preparing the compound of formula (IV) of the present invention or a tautomer, mesomer, racemate, enantiomer, diastereomer thereof, or mixture thereof, or a pharmaceutically acceptable salt thereof, comprises the following steps:

in Step 1, a compound of formula (IIB') is reacted with a compound of formula (IV-1) and bis(trichloromethyl)carbonate under an alkaline condition to obtain a compound of formula (IV-a);

in Step 2, the compound of formula (IV-a) is subjected to a hydrolysis reaction under an alkaline condition to obtain a compound of formula (IV-b);

in Step 3, the compound of formula (IV-b) is reacted with a compound of formula (IIB) or a salt thereof to obtain the compound of formula (IV).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The catalyst includes, but is not limited to, Pd/C, Raney Ni, platinum dioxide, tetra-triphenylphosphine palladium, palladium dichloride, palladium acetate, 2-dicyclohexylphosphino-2,4,6-triisopropylbiphenyl, [1,1'-bis(diphenylphosphino)ferrocene]dichloropalladium, 1,1'-bis(dibenzylphosphoryl)ferrocene palladium dichloride, tris(dibenzylideneacetone)dipalladium and 2-dicyclohexylphosphino-2',6'-dimethoxybiphenyl, and preferably [1,1'-bis(diphenylphosphino)ferrocene]dichloropalladium and 2-dicyclohexylphosphino-2',6'-dimethoxybiphenyl.

The condensing agent includes, but is not limited to, 1-(3-dimethylaminopropyl)-3-ethylcarbodiimide hydrochloride, N,N-dicyclohexylcarbodiimide, N,N-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is alkyl, and preferably methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, $R^1$, $R^4$, s and n are as defined in formula (I).

Scheme VII

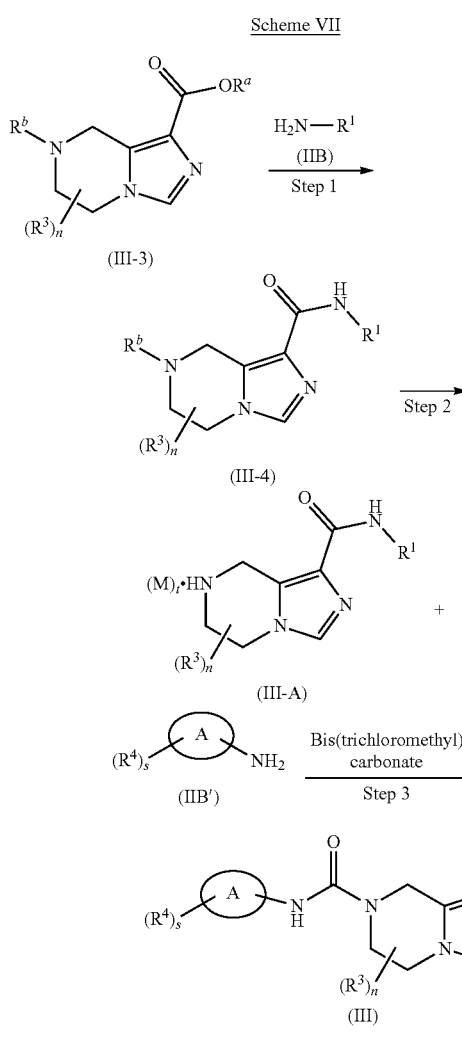

The reagent that provides an acidic condition includes, but is not limited to, hydrogen chloride, trifluoroacetic acid, formic acid, acetic acid, hydrochloric acid, sulfuric acid, methanesulfonic acid, nitric acid, phosphoric acid, p-toluenesulfonic acid, $Me_3SiCl$ and $TMSOT_f$.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

M is trifluoroacetic acid or hydrochloric acid; $R^a$ is hydrogen or alkyl, and preferably hydrogen, methyl or ethyl;

$R^b$ is an amino protecting group, and preferably tert-butoxycarbonyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and t is 0 or 1; ring A, $R^1$, $R^4$, s and n are as defined in formula (III).

Scheme VIII

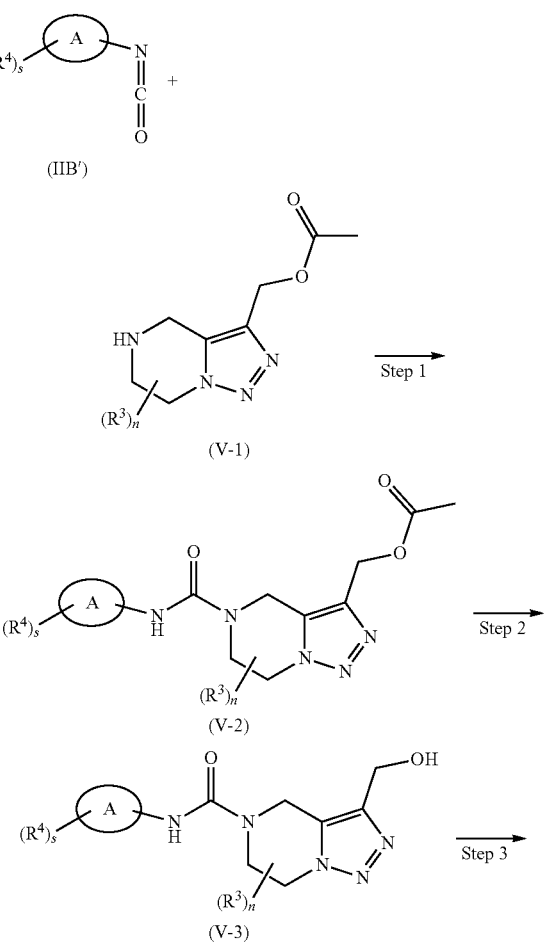

A method for preparing the compound of formula (III) of the present invention or a tautomer, mesomer, racemate, enantiomer, diastereomer thereof, or mixture thereof, or a pharmaceutically acceptable salt thereof, comprises the following steps of:

in Step 1, a compound of formula (III-3) is reacted with a compound of formula (IIB) or a salt thereof in the presence of a condensing agent under an alkaline condition to obtain a compound of formula (III-4);

in Step 2, the compound of formula (III-4) is subjected to a deprotection reaction under an acidic condition to obtain a compound of formula (IIIA) or a salt thereof;

in Step 3, the compound of formula (IIIA) or a salt thereof is reacted with a compound of formula (IIB') or a salt thereof and bis(trichloromethyl)carbonate to obtain the compound of formula (III).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

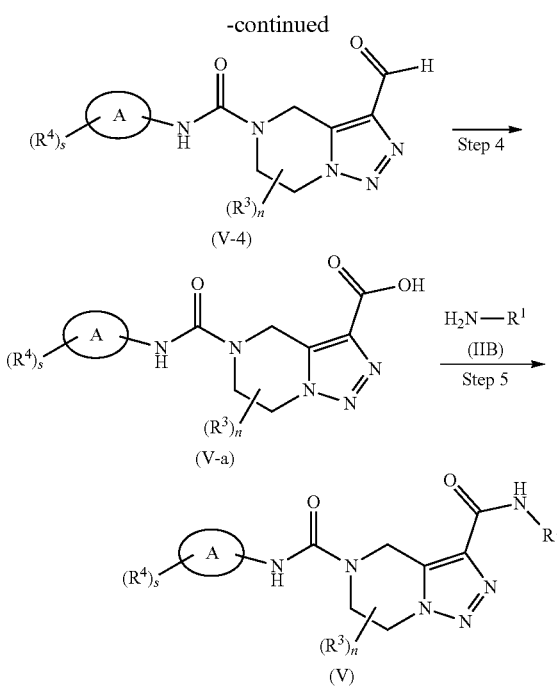

A method for preparing the compound of formula (V) of the present invention or a tautomer, mesomer, racemate, enantiomer, diastereomer thereof, or mixture thereof, or a pharmaceutically acceptable salt thereof, comprises the following steps of:

in Step 1, a compound of formula (IIB') is reacted with a compound of formula (V-1) under an alkaline condition to obtain a compound of formula (V-2);

in Step 2, the compound of formula (V-2) is subjected to a reduction reaction in the presence of a reducing agent to obtain a compound of formula (V-3);

in Step 3, the compound of formula (V-3) and an oxidizing agent are subjected to an oxidation reaction to obtain a compound of formula (V-4);

in Step 4, the compound of formula (V-4) is subjected to an oxidation reaction in the presence of an oxidizing agent to obtain a compound of formula (V-a);

in Step 5, the compound of formula (V-a) and a compound of formula (IIB) or a salt thereof are subjected to a condensation reaction to obtain the compound of formula (V).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The reducing agent includes, but is not limited to, lithium aluminum hydride, $NaBH_4$, $NaBH_4$—$ZnCl_2$ and diisobutylaluminum hydride (DIBAL-H).

The oxidizing agent includes, but is not limited to, pyridinium chlorochromate (PCC), Jones reagent, Collins reagent, pyridinium dichromate (PDC), oxalyl chloride (Swern oxidation), carbodiimide, sodium chlorite and potassium permanganate.

The condensing agent includes, but is not limited to, 1-(3-dimethylaminopropyl)-3-ethylcarbodiimide hydrochloride, N,N-dicyclohexylcarbodiimide, N,N-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, $R^1$, $R^4$, s and n are as defined in formula (V).

Scheme IX

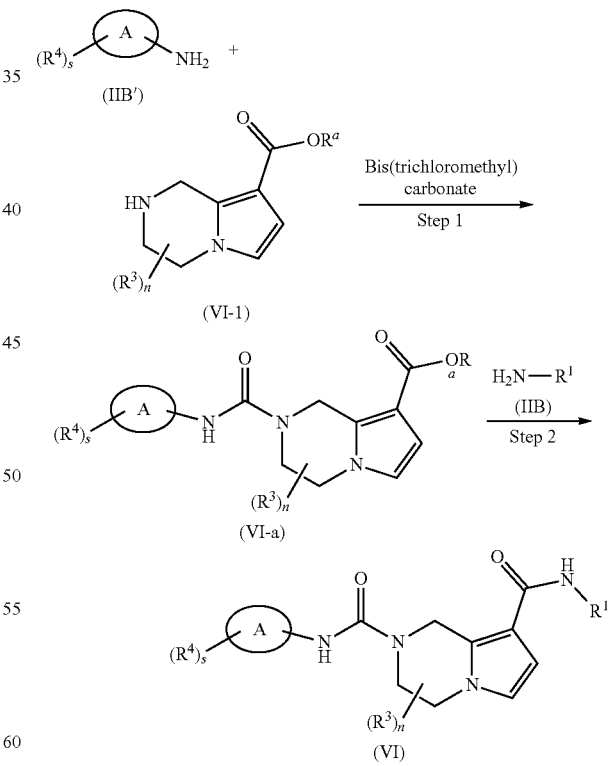

A method for preparing the compound of formula (VI) of the present invention or a tautomer, mesomer, racemate, enantiomer, diastereomer thereof, or mixture thereof, or a pharmaceutically acceptable salt thereof, comprises the following steps of:

in Step 1, a compound of formula (IIB') is reacted with a compound of formula (VI-1) and bis(trichloromethyl)carbonate under an alkaline condition to obtain a compound of formula (VI-2);

in Step 2, the compound of formula (VI-a) is reacted with a compound of formula (IIB) or a salt thereof to obtain the compound of formula (VI).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N-dicyclohexylcarbodiimide, N,N-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is hydrogen or alkyl, and preferably hydrogen, methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and ring A, $R^1$, $R^4$, s and n are as defined in formula (I).

Scheme X

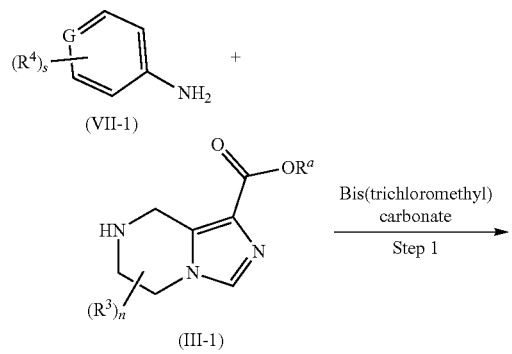

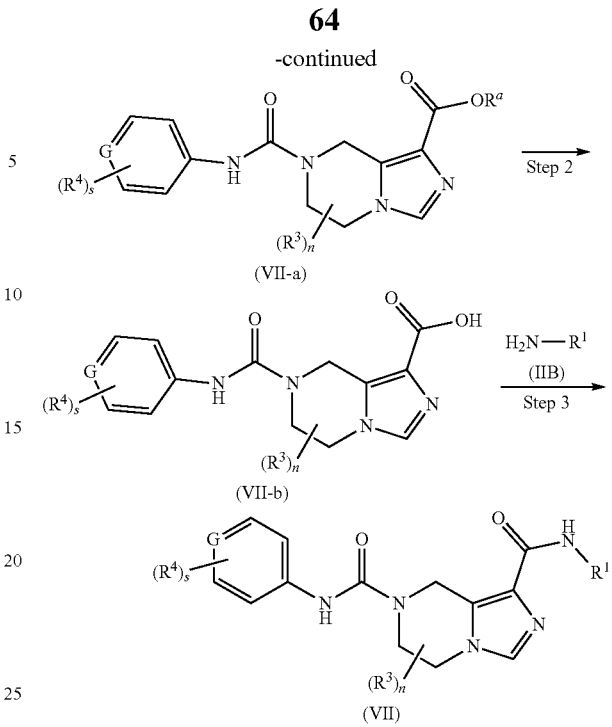

A method for preparing the compound of formula (VII) of the present invention or a tautomer, mesomer, racemate, enantiomer, diastereomer thereof, or mixture thereof, or a pharmaceutically acceptable salt thereof, comprises the following steps of:

in Step 1, a compound of formula (VII-1) is reacted with a compound of formula (III-1) and bis(trichloromethyl) carbonate under an alkaline condition to obtain a compound of formula (VII-a);

in Step 2, the compound of formula (IV-a) is subjected to a hydrolysis reaction under an alkaline condition to obtain a compound of formula (VII-b);

in Step 3, the compound of formula (VII-b) and a compound of formula (IIB) or a salt thereof are subjected to a condensation reaction to obtain the compound of formula (VII).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N-dicyclohexylcarbodiimide, N,N-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is alkyl, and preferably methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and $R^1$, $R^4$, s and n are as defined in formula (I).

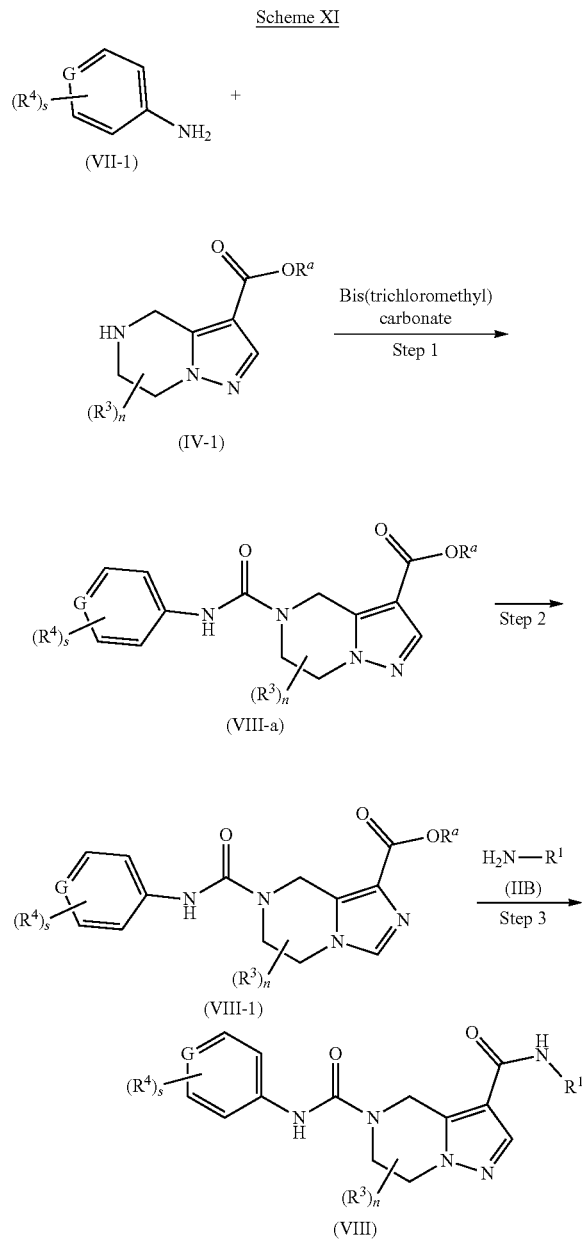

Scheme XI

A method for preparing the compound of formula (VIII) of the present invention or a tautomer, mesomer, racemate, enantiomer, diastereomer thereof, or mixture thereof, or a pharmaceutically acceptable salt thereof, comprises the following steps:

in Step 1, a compound of formula (VII-1) is reacted with a compound of formula (IV-1) and bis(trichloromethyl) carbonate under an alkaline condition to obtain a compound of formula (VIII-a);

in Step 2, the compound of formula (VIII-a) is subjected to a hydrolysis reaction under an alkaline condition to obtain a compound of formula (VIII-b);

in Step 3, the compound of formula (VIII-b) and a compound of formula (IIB) or a salt thereof are subjected to a condensation reaction to obtain the compound of formula (VIII).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N-dicyclohexylcarbodiimide, N,N-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

$R^a$ is alkyl, and preferably methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl; and $R^1$, $R^4$, s and n are as defined in formula (I).

Scheme XII

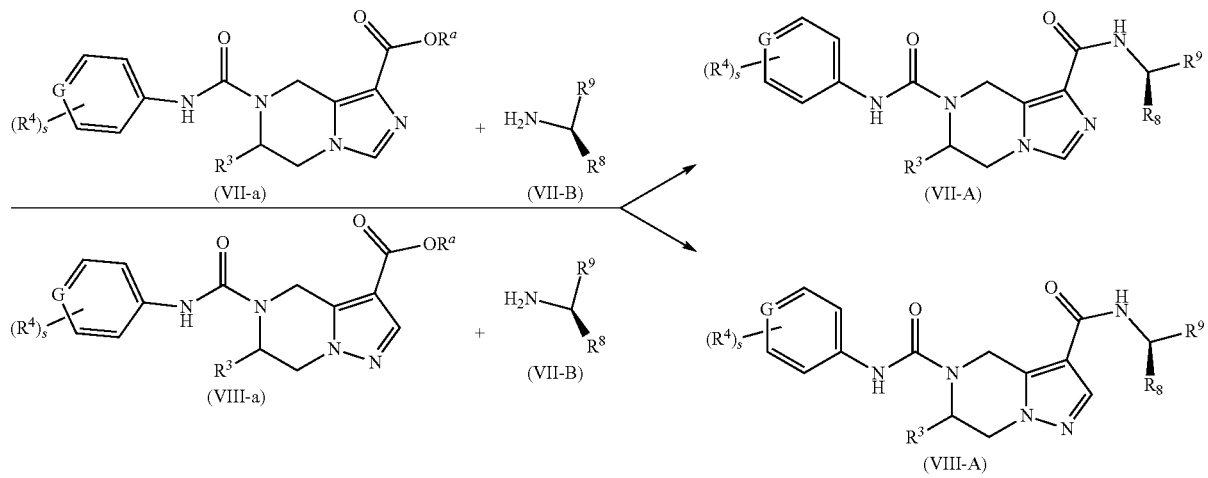

A method for preparing the compound of formula (VII-A) or formula (VIII-A) of the present invention or a tautomer, mesomer, racemate, enantiomer, diastereomer thereof, or mixture thereof, or a pharmaceutically acceptable salt thereof, comprises the following step of:

reacting a compound of formula (VII-a) with a compound of formula (VII-B) or a salt thereof to obtain the compound of formula (VII-A); or reacting a compound of formula (VIII-a) with a compound of formula (VII-B) or a salt thereof to obtain the compound of formula (VIII-A).

The reagent that provides an alkaline condition includes organic bases and inorganic bases. The organic bases include, but are not limited to, triethylamine, a 1 M solution of lithium bis(trimethylsilyl)amide in tetrahydrofuran, N,N-diisopropylethylamine, n-butyllithium, lithium diisopropylamide, potassium acetate, sodium tert-butoxide and potassium tert-butoxide. The inorganic bases include, but are not limited to, sodium hydride, sodium hydroxide, potassium phosphate, sodium carbonate, sodium bicarbonate, potassium carbonate and cesium carbonate.

The condensing agent includes, but is not limited to, 1-(3-dimethylaminopropyl)-3-ethylcarbodiimide hydrochloride, N,N-dicyclohexylcarbodiimide, N,N-diisopropylcarbodiimide, O-benzotriazole-N,N,N',N'-tetramethyluronium tetrafluoroborate, 1-hydroxybenzotriazole, 1-hydroxy-7-azobenzotriazole, O-benzotriazole-N,N,N',N'-tetramethyluronium hexafluorophosphate, O-(7-azabenzotriazol-1-yl)-N,N,N',N'-tetramethyluronium hexafluorophosphate, 2-(7-oxobenzotriazole)-N,N,N',N'-tetramethyluronium hexafluorophosphate, benzotriazol-1-yloxytris(dimethylamino)phosphonium hexafluorophosphate and benzotriazol-1-yl-oxytripyrrolidinylphosphonium hexafluorophosphate, and preferably 2-(7-oxobenzotriazole)-N,N,N',N'-tetramethyluronium hexafluorophosphate.

The above reaction is preferably carried out in a solvent. The solvent used includes, but is not limited to, acetic acid, methanol, ethanol, toluene, tetrahydrofuran, dichloromethane, petroleum ether, ethyl acetate, n-hexane, dimethyl sulfoxide, 1,4-dioxane, water, N,N-dimethylformamide, and mixtures thereof.

Wherein:

G is C or N;

$R^a$ is hydrogen or alkyl, and preferably hydrogen, methyl or ethyl;

each $R^3$ is identical or different and each is independently selected from the group consisting of hydrogen, halogen, alkyl, haloalkyl, alkoxy, haloalkoxy, cyano, amino, nitro, hydroxy, hydroxyalkyl, cycloalkyl, heterocyclyl, aryl, heteroaryl, —$OR^6$, —$C(O)R^6$, —$C(O)OR^6$ and —$S(O)_mR^6$, and preferably hydrogen or alkyl;

$R^8$ is alkyl, preferably methyl;

$R^9$ is alkyl, wherein the alkyl is optionally further substituted by one or more halogens; and $R^4$ and s are as defined in formula (I).

PREFERRED EMBODIMENTS

The present invention will be further described with reference to the following examples, but the examples should not be considered as limiting the scope of the present invention.

EXAMPLES

The structures of the compounds were identified by nuclear magnetic resonance (NMR) and/or mass spectrometry (MS). NMR shifts (δ) are given in $10^{-6}$ (ppm). NMR was determined by a Bruker AVANCE-400 machine. The solvents for determination were deuterated-dimethyl sulfoxide (DMSO-$d_6$), deuterated-chloroform (CDCl$_3$) and deuterated-methanol (CD$_3$OD), and the internal standard was tetramethylsilane (TMS).

MS was determined by a FINNIGAN LCQAd (ESI) mass spectrometer (manufacturer: Thermo, type: Finnigan LCQ advantage MAX).

High performance liquid chromatography (HPLC) analysis was determined on an Agilent HPLC 1200DAD, Agilent HPLC 1200VWD and Waters HPLC e2695-2489 high pressure liquid chromatographs.

Chiral HPLC analysis was determined on an Agilent 1260 DAD high performance liquid chromatograph.

High performance liquid preparation was carried out on Waters 2767, Waters 2767-SQ Detecor2, Shimadzu LC-20AP and Gilson-281 preparative chromatographs.

Chiral preparation was carried out on a Shimadzu LC-20AP preparative chromatograph.

CombiFlash rapid preparation instrument used was Combiflash Rf200 (TELEDYNE ISCO). Yantai Huanghai HSGF254 or Qingdao GF254 silica gel plate was used as the thin-layer silica gel chromatography (TLC) plate. The dimension of the silica gel plate used in TLC was 0.15 mm to 0.2 mm, and the dimension of the silica gel plate used in product purification was 0.4 mm to 0.5 mm.

Yantai Huanghai 200 to 300 mesh silica gel was generally used as a carrier for silica gel column chromatography.

The average kinase inhibition rates and $IC_{50}$ values were determined by a NovoStar ELISA (BMG Co., Germany).

The known starting materials of the present invention can be prepared by the known methods in the art, or can be purchased from ABCR GmbH & Co. KG, Acros Organnics, Aldrich Chemical Company, Accela ChemBio Inc., Dari chemical Company and the like.

Unless otherwise stated, the reactions were carried out under argon atmosphere or nitrogen atmosphere.

"Argon atmosphere" or "nitrogen atmosphere" means that a reaction flask is equipped with an argon or nitrogen balloon (about 1 L).

"Hydrogen atmosphere" means that a reaction flask is equipped with a hydrogen balloon (about 1 L).

Pressurized hydrogenation reactions were performed on a Parr 3916EKX hydrogenation instrument and a Qinglan QL-500 hydrogen generator or HC2-SS hydrogenation instrument.

In hydrogenation reactions, the reaction system was generally vacuumed and filled with hydrogen, and the above operation was repeated three times.

CEM Discover-S 908860 type microwave reactor was used in microwave reactions.

Unless otherwise stated, the solution refers to an aqueous solution.

Unless otherwise stated, the reaction temperature is room temperature from 20° C. to 30° C.

The reaction process in the examples was monitored by thin layer chromatography (TLC). The developing solvent used in the reactions, the eluent system in column chromatography and the developing solvent system in thin layer chromatography for purification of the compounds included: A: dichloromethane/methanol system, B: n-hexane/ethyl acetate system, and C: petroleum ether/ethyl acetate system. The ratio of the volume of the solvent was adjusted according to the polarity of the compounds, and a small quantity of alkaline reagent such as triethylamine or acidic reagent such as acetic acid can also be added for adjustment.

Example 1

(R)—$N^7$-(3,4,5-Trifluorophenyl)-$N^1$-(1,1,1-trifluoropropan-2-yl)-5,6-dihydroimidazo[1,5-α]pyrazine-1,7(8H)-dicarboxamide

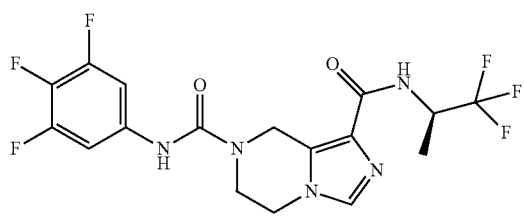

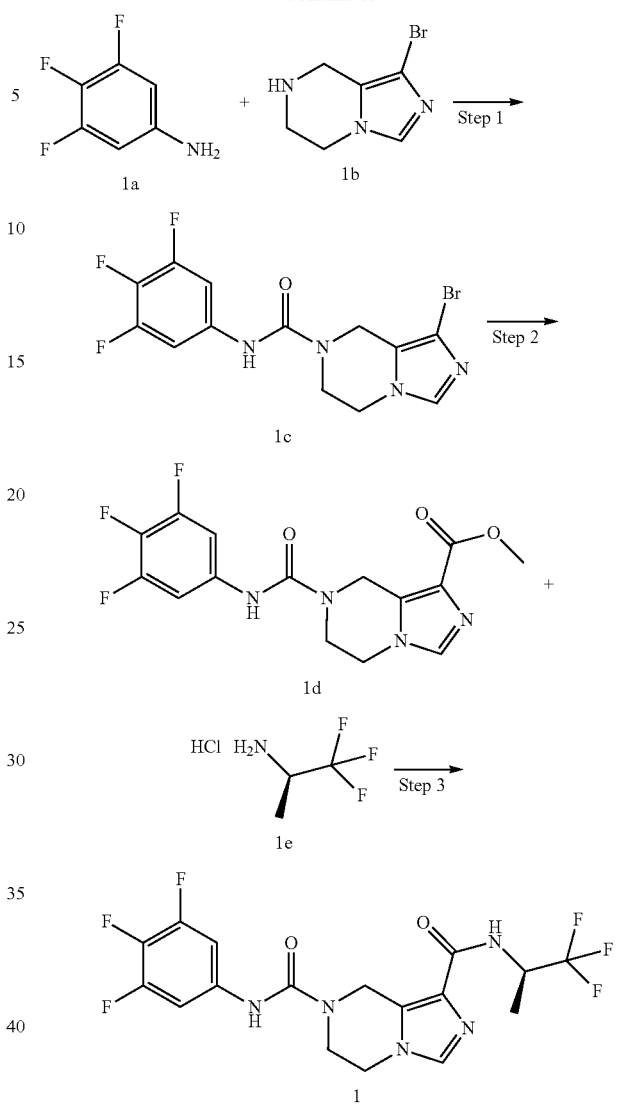

Step 1

1-Bromo-N-(3,4,5-trifluorophenyl)-5,6-dihydroimidazo[1,5-α]pyrazine-7(8H)-carboxamide 1c 3,4,5-Trifluoroaniline 1a (0.365 g, 2.48 mmol, prepared according to the known method disclosed in "*Tetrahedron Letters,* 51(17), 2010, 2265-2268") and 1-bromo-5,6,7,8-tetrahydroimidazo[1,5-α]pyrazine 1b (501.36 mg, 2.48 mmol, Shanghai Shuya Pharmaceutical Technology Co., Ltd.) were dissolved in 30 mL of dichloromethane, followed by addition of triethylamine (753.26 mg, 7.44 mmol) and bis(trichloromethyl)carbonate (294.53 mg, 992.54 μmol). After stirring for 12 hours, the reaction solution was concentrated under reduced pressure, and the resulting residue was purified by thin layer chromatography with developing solvent system A to obtain the title compound 1c (300 mg, yield: 32.2%).

MS m/z (ESI): 376.1 [M+1].

Step 2

Methyl 7-((3,4,5-trifluorophenyl)carbamoyl)-5,6,7,8-tetrahydroimidazo[1,5-α]pyrazine-1-carboxylate 1d Dicobalt octacarbonyl (525.03 mg, 1.54 mmol) and potassium carbonate (1.06 g, 7.68 mmol) were dissolved in 20 mL of methanol under a carbon monoxide atmosphere. The solution was stirred at 60° C. for 15 minutes, followed by addition of compound 1c (300 mg, 767.71 μmol) and methyl 2-chloroacetate (499.88 mg, 4.61 mmol). After stirring for 8 hours, the reaction solution was cooled to room temperature and filtrated. The filtrate was concentrated under reduced pressure, and the resulting residue was purified by thin layer chromatography with developing solvent system A to obtain the title compound 1d (70 mg, yield: 21.8%).

MS m/z (ESI): 355.3 [M+1].

Step 3

(R)—$N^7$-(3,4,5-Trifluorophenyl)-$N^1$-(1,1,1-trifluoropropan-2-yl)-5,6-dihydroimidazo[1,5-α]pyrazine-1,7(8H)-dicarboxamide Compound 1d (70 mg, 197.58 μmol) and (2R)-1,1,1-trifluoropropan-2-amine hydrochloride 1e (59.09 mg, 395.16 μmol, prepared according to the method disclosed in the patent application "CN102875270A") were dissolved in 10 mL of tetrahydrofuran, followed by dropwise addition of 0.988 μL of a 1M solution of lithium bis(trimethylsilyl)amide in tetrahydrofuran at 0° C. After completion of the addition, the reaction solution was warmed up slowly to room temperature, and stirred for 6 hours. The reaction solution was concentrated under reduced pressure, and the resulting residue was added with 15 mL of water, and extracted with ethyl acetate (15 mL×3). The organic phases were combined and concentrated under reduced pressure, and the resulting residue was purified by thin layer chromatography with developing solvent system A to obtain the title compound 1 (15 mg, yield: 17.4%).

MS m/z (ESI): 436.2 [M+1].

$^1$H NMR (400 MHz, DMSO-$d_6$) δ 9.31 (s, 1H), 8.30 (d, 1H), 7.70 (s, 1H), 7.25-7.31 (m, 2H), 5.05 (s, 2H), 4.78-4.86 (m, 1H), 4.21-4.24 (m, 2H), 3.94-3.96 (m, 2H), 1.31-1.44 (dd, 3H).

Example 2

(R)—$N^5$-(3,4-Difluorophenyl)-$N^3$-(1,1,1-trifluoropropan-2-yl)-6,7-dihydropyrazolo[1,5-α]pyrazine-3,5(4H)-dicarboxamide

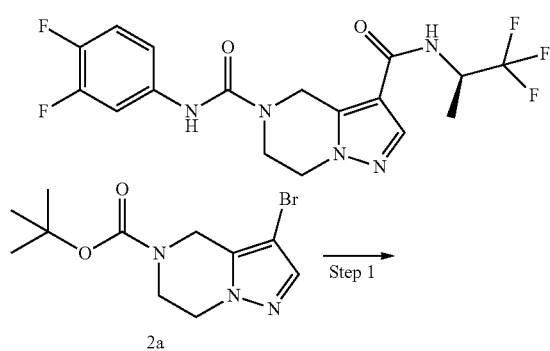

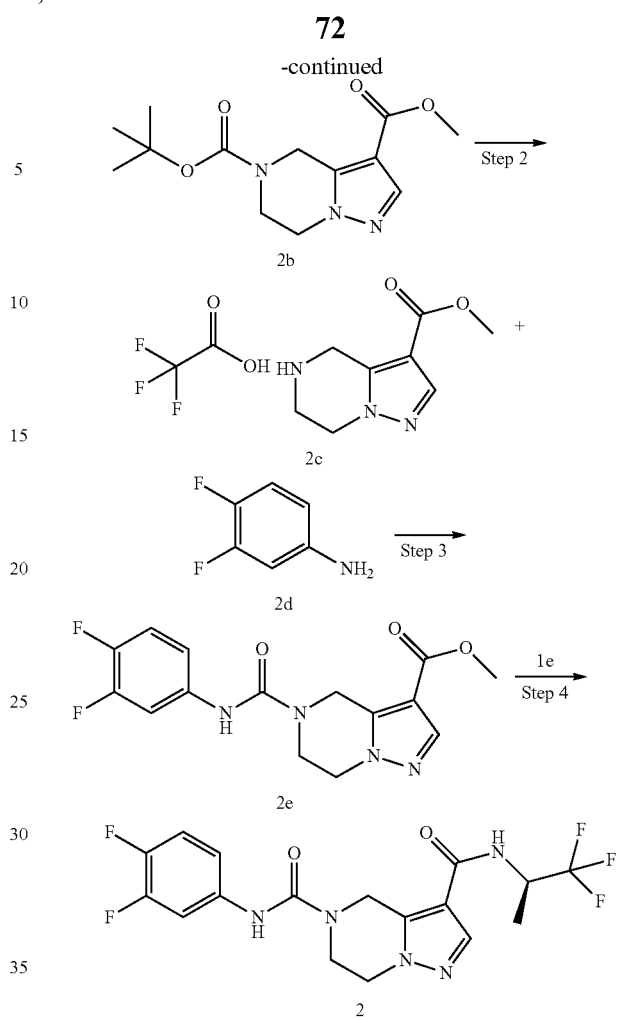

Step 1

5-Tert-butyl 3-methyl 6,7-dihydropyrazolo[1,5-α]pyrazine-3,5(4H)-dicarboxylate 2b Dicobalt octacarbonyl (2.26 g, 6.62 mmol) and potassium carbonate (4.57 g, 33.09 mmol) were dissolved in 20 mL of methanol under a carbon monoxide atmosphere. The solution was stirred at 60° C. for 15 minutes, followed by addition of tert-butyl 3-bromo-6,7-dihydropyrazolo[1,5-α]pyrazine-5(4H)-carboxylate 2a (1 g, 3.31 mmol, prepared according to the known method disclosed in "*ACS Medicinal Chemistry Letters*, 2015, 6(1), 37-41") and methyl 2-chloroacetate (2.15 g, 19.86 mmol). After stirring for 16 hours, the reaction solution was concentrated under reduced pressure, added with 100 mL of ethyl acetate, filtrated, and washed with 100 mL of ethyl acetate. The filtrate was concentrated under reduced pressure, and the resulting residue was purified by thin layer chromatography with developing solvent system A to obtain the title compound 2b (0.5 g, yield: 53%).

MS m/z (ESI): 282.1 [M+1].

Step 2

Methyl 4,5,6,7-tetrahydropyrazolo[1,5-α]pyrazine-3-carboxylate trifluoroacetate 2c Compound 2b (600 mg, 2.13 mmol) was dissolved in 10 mL of dichloromethane, followed by addition of trifluoroacetic acid (2.43 g, 21.33 mmol). After completion of the addition, the reaction solution was stirred for 12 hours, and concentrated under reduced pressure to obtain the crude title compound 2c (250 mg), which was used directly in the next step without purification.

MS m/z (ESI): 182.0 [M+1].

Step 3

Methyl 5-((3,4-difluorophenyl)carbamoyl)-4,5,6,7-tetrahydropyrazolo[1,5-α]pyrazine-3-carboxylate 2e The crude compound 2c (200 mg, 1.10 mmol), 3,4-difluoroaniline 2d (142.51 mg, 1.10 mmol) and triethylamine (335.08 mg, 3.31 mmol) were dissolved in 10 mL of tetrahydrofuran, followed by addition of bis(trichloromethyl)carbonate (114.64 mg, 386.33 μmol) at 0° C. The reaction solution was warmed up slowly to room temperature, and stirred for 3 hours. The reaction solution was concentrated under reduced pressure, and the resulting residue was purified by thin layer chromatography with developing solvent system A to obtain the title compound 2e (100 mg, yield: 26.9%).

MS m/z (ESI): 337.4 [M+1].

Step 4

(R)—N⁵-(3,4-Difluorophenyl)-N³-(1,1,1-trifluoropropan-2-yl)-6,7-dihydropyrazolo[1,5-α]pyrazine-3,5(4H)-dicarboxamide 2

Compound 2e (100 mg, 297.36 μmol) and compound 1e (133.40 mg, 892.08 μmol) were dissolved in 20 mL of tetrahydrofuran, followed by dropwise addition of 4.46 mL of a 1M solution of lithium bis(trimethylsilyl)amide in tetrahydrofuran at 0° C. After completion of the addition, the reaction solution was warmed up slowly to room temperature, and stirred for 3 hours. The reaction solution was added with 2 mL of saturated ammonium chloride solution and 10 mL of water, and extracted with ethyl acetate (20 mL×2). The organic phases were combined and concentrated under reduced pressure, and the resulting residue was purified by thin layer chromatography with developing solvent system A. The resulting crude product was purified by preparative high performance liquid chromatography (Waters 2767-SQ Detecor2, elution system: ammonium bicarbonate, water, acetonitrile) to obtain the title compound 2 (15 mg, yield: 12.1%).

MS m/z (ESI): 418.2 [M+1].
¹H NMR (400 MHz, CD₃OD) δ 8.07 (s, 1H), 7.51-7.46 (m, 1H), 7.22-7.16 (m, 2H), 5.05 (s, 2H), 4.88-4.82 (m, 1H), 4.29-4.26 (m, 2H), 4.05-4.02 (m, 2H), 1.42-1.40 (m, 3H).

Example 3

(R)—N⁷-(3-Cyano-4-fluorophenyl)-N¹-(1,1,1-trifluoropropan-2-yl)-5,6-dihydroimidazo[1,5-α]pyrazine-1,7(81H)-dicarboxamide 3

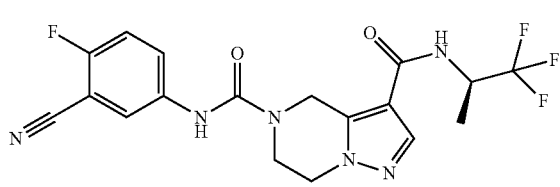

Step 1

Tert-butyl (R)-1-((1,1,1-trifluoropropan-2-yl)carbamoyl)-5,6-dihydroimidazo[1,5-α]pyrazine-7(8H)-carboxylate 3b 7-Tert-butyl 1-methyl 5,6-dihydroimidazo[1,5-α]pyrazine-1,7(8H)-dicarboxylate 3a (469.78 mg, 1.67 mmol, prepared according to the method disclosed in the patent application "US20110034443A1") and compound 1e (249.74 mg, 1.67 mmol) were dissolved in 20 mL of tetrahydrofuran under an argon atmosphere, followed by dropwise addition of 3.3 mL of a 1M solution of lithium bis(trimethylsilyl)amide in tetrahydrofuran in an ice bath. The reaction solution was warmed up to room temperature, and stirred for 1 hour. The reaction solution was concentrated under reduced pressure, and the resulting residue was purified by thin layer chromatography with developing solvent system A to obtain the title compound 3b (130 mg, yield: 21.5%).

MS m/z (ESI): 363.2 [M+1].

Step 2

(R)—N-(1,1,1-Trifluoropropan-2-yl)-5,6,7,8-tetrahydroimidazo[1,5-α]pyrazine-1-carboxamide trifluoroacetate 3c Compound 3b (130 mg, 358.77 μmol) and trifluoroacetic acid (204.54 mg, 1.79 mmol) were dissolved in 2 mL of dichloromethane successively. After stirring for 2 hours, the reaction solution was concentrated under reduced pressure to obtain the crude title compound 3c (135 mg), which was used directly in the next step without purification.

Step 3

(R)—N⁷-(3-Cyano-4-fluorophenyl)-N¹-(1,1,1-trifluoropropan-2-yl)-5,6-dihydroimidazo[1,5-α]pyrazine-1,7(8H)-dicarboxamide 3

The crude compound 3c (50 mg, 190.67 μmol), 5-amino-2-fluorobenzonitrile 3d (25.96 mg, 190.67 μmol, prepared according to the known method disclosed in "*Bioorganic & Medicinal Chemistry Letters*, 2006, 16(19), 5176-5182") and triethylamine (28.94 mg, 286.01 μmol) were dissolved in 10 mL of tetrahydrofuran, followed by addition of bis(trichloromethyl)carbonate (28.29 mg, 95.34 μmol) in an ice bath. After stirring for 1 hour the reaction solution was concentrated under reduced pressure, and the residue was purified by preparative high performance liquid chromatography (Waters 2767-SQ Detecor2, elution system: ammonium bicarbonate, water, acetonitrile) to obtain the title compound 3 (2 mg, yield: 2.5%).

MS m/z (ESI): 425.1 [M+1].

$^1$H NMR (400 MHz, DMSO-d$_6$) δ 9.22 (s, 1H), 8.32 (d, 1H), 7.95 (d, 1H), 7.81-7.77 (m, 2H), 7.47-7.43 (m, 1H), 4.96 (s, 2H), 4.81-4.74 (m, 1H), 4.17-4.10 (m, 2H), 3.89-3.86 (m, 2H), 1.39-1.35 (dd, 3H).

Example 4

(R)—N⁵-(3,4,5-Trifluorophenyl)-N³-(1,1,1-trifluoropropan-2-yl)-6,7-dihydropyrazolo[1,5-α]pyrazine-3,5(4H)-dicarboxamide 4

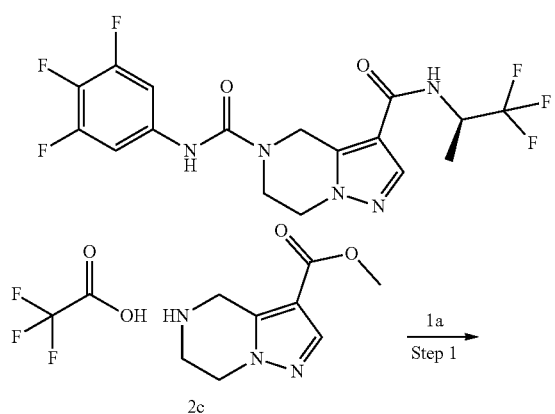

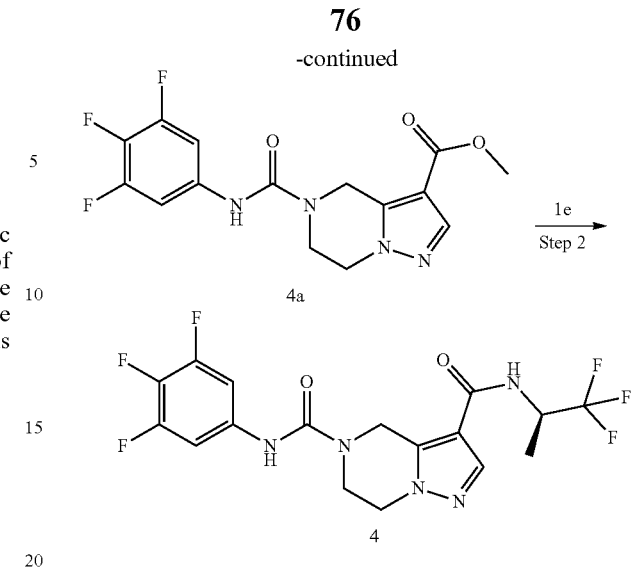

Step 1

Methyl 5-((3,4,5-trifluorophenyl)carbamoyl)-4,5,6,7-tetrahydropyrazolo[1,5-α]pyrazine-3-carboxylate 4a Compound 2c (100 mg, 338.74 μmol), compound 1a (49.83 mg, 338.74 μmol) and trifluoroacetic acid (342.77 mg, 3.39 mmol) were dissolved in 10 mL of tetrahydrofuran, followed by addition of bis(trichloromethyl)carbonate (35.18 mg, 118.56 3 μmol) at 0° C. The reaction solution was warmed up slowly to room temperature, and stirred for 3 hours. The reaction solution was concentrated under reduced pressure, and the resulting residue was purified by thin layer chromatography with developing solvent system A to obtain the title compound 4a (50 mg, yield: 25.0%).

MS m/z (ESI): 355.1 [M+1].

Step 2

(R)—N⁵-(3,4,5-Trifluorophenyl)-N³-(1,1,1-trifluoropropan-2-yl)-6,7-dihydropyrazolo[1,5-α]pyrazine-3,5(4H)-dicarboxamide 4

Compound 4a (50 mg, 141.13 μmol) and compound 1e (63.31 mg, 423.39 μmol) were dissolved in 20 mL of tetrahydrofuran, followed by dropwise addition of 2.12 mL of a 1M solution of lithium bis(trimethylsilyl)amide in tetrahydrofuran at 0° C. After completion of the addition, the reaction solution was warmed up slowly to room temperature, and stirred for 3 hours. The reaction solution was added with 2 mL of saturated ammonium chloride solution and 10 mL of water, and extracted with ethyl acetate (20 mL×2). The organic phases were combined and concentrated under reduced pressure, and the resulting residue was purified by thin layer chromatography with developing solvent system A. The resulting crude product was purified by preparative high performance liquid chromatography (Waters 2767-SQ Detecor2, elution system: ammonium bicarbonate, water, acetonitrile) to obtain the title compound 4 (5 mg, yield: 4%).

MS m/z (ESI): 436.0 [M+1].

$^1$H NMR (400 MHz, CD$_3$OD) δ 8.07 (s, 1H), 7.30-7.26 (m, 2H), 5.04 (s, 2H), 4.88-4.82 (m, 1H), 4.28-4.26 (m, 2H), 4.04-4.01 (m, 2H), 1.42-1.40 (m, 3H).

Example 5

(R)—N⁷-(3,4-Difluorophenyl)-N¹-(1,1,1-trifluoropropan-2-yl)-5,6-dihydroimidazo[1,5-α]pyrazine-1,7(8H)-dicarboxamide 5

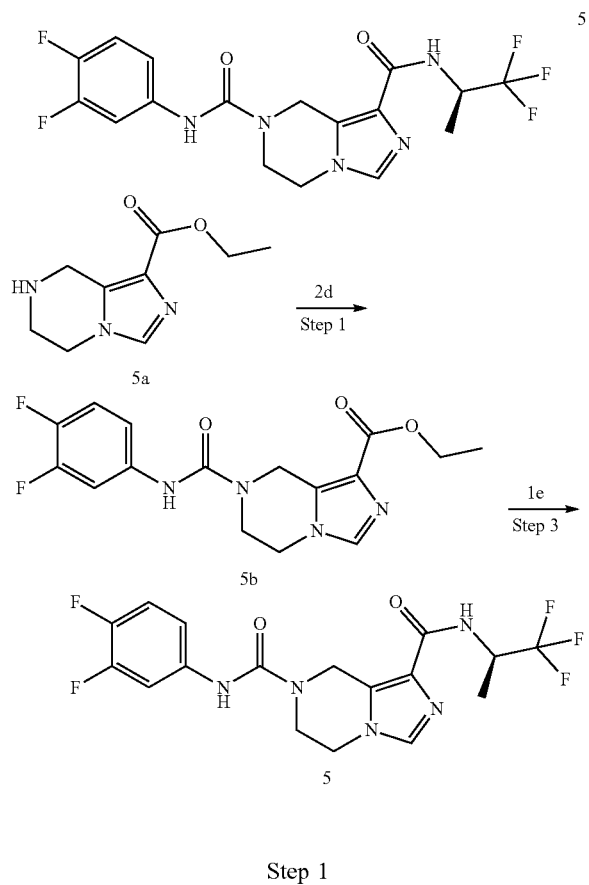

drofuran, followed by addition of lithium bis(trimethylsilyl)amide (107.47 mg, 642.27 μmol) in an ice bath. After stirring for 1 hour, the reaction solution was concentrated under reduced pressure, and the resulting residue was purified by thin layer chromatography with developing solvent system A. The resulting crude product was purified by preparative high performance liquid chromatography (Waters 2767-SQ Detecor2, elution system: ammonium bicarbonate, water, acetonitrile) to obtain the title compound 5 (20 mg, yield: 30.4%).

MS m/z (ESI): 418.2 [M+1].

$^1$H NMR (400 MHz, DMSO-$d_6$) δ 9.09 (s, 1H), 8.31 (d, 1H), 7.76 (s, 1H), 7.64-7.60 (m, 1H), 7.34-7.23 (m, 2H), 4.94 (s, 2H), 4.79-4.77 (m, 1H), 4.16-4.14 (m, 2H), 3.88-3.85 (m, 2H), 1.37-1.35 (dd, 3H).

Example 6

(S)—N⁷-(3,4-Difluorophenyl)-6-methyl-N¹-((R)-1,1,1-trifluoropropan-2-yl)-5,6-dihydroimidazo[1,5-α]pyrazine-1,7(8H)-dicarboxamide 6

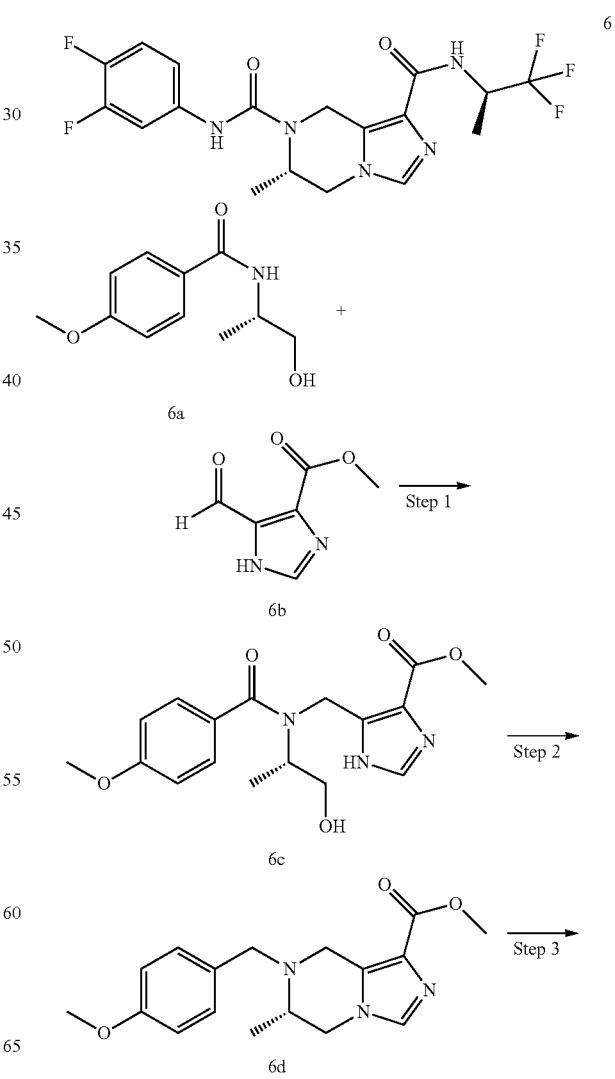

Step 1

Ethyl 7-((3,4-difluorophenyl)carbamoyl)-5,6,7,8-tetrahydroimidazo[1,5-α]pyrazine-1-carboxylate 5b Ethyl 5,6,7,8-tetrahydroimidazo[1,5-α]pyrazine-1-carboxylate 5a (100 mg, 512.25 mol, prepared according to the method disclosed in the patent application "CN102464661A") and compound 2d (79.36 mg, 614.70 μmol) were added to 20 mL of tetrahydrofuran, followed by addition of bis(trichloromethyl)carbonate (76.01 mg, 256.13 mol) in an ice bath. The reaction solution was warmed up to room temperature and stirred for 1 hour. The reaction solution was concentrated under reduced pressure, and the resulting residue was purified by thin layer chromatography with developing solvent system A to obtain the title compound 5b (110 mg, yield: 61.3%).

MS m/z (ESI): 351.1 [M+1].

Step 2

(R)—N⁷-(3,4-Difluorophenyl)-N¹-(1,1,1-trifluoropropan-2-yl)-5,6-dihydroimidazo[1,5-α]pyrazine-1,7(8H)-dicarboxamide 5

Compound 5b (75 mg, 214.09 μmol) and compound 1e (48.02 mg, 321.14 μmol) were added to 20 mL of tetrahy-

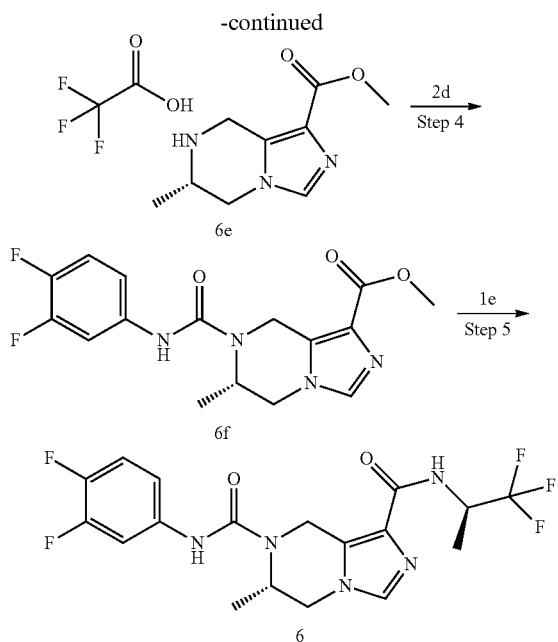

filtrated. The filtrate was concentrated under reduced pressure, and the resulting residue was purified by silica gel column chromatography with eluent system A to obtain the title compound 6d (4.5 g, yield: 43.2%).

MS m/z (ESI): 315.9 [M+1].

Step 3

Methyl (S)-6-methyl-5,6,7,8-tetrahydroimidazo[1,5-α]pyrazine-1-carboxylate trifluoroacetate 6e Compound 6d (0.6 g, 2.33 mmol) was dissolved in 2 mL of trifluoroacetic acid. The reaction solution was heated to 100° C. in a microwave for 5 minutes, cooled to room temperature, and concentrated under reduced pressure to obtain the crude title compound 6e (0.6 g), which was used directly in the next step without purification.

MS m/z (ESI): 196.1 [M+1].

Step 4

Methyl (S)-7-((3,4-difluorophenyl)carbamoyl)-6-methyl-5,6,7,8-tetrahydroimidazo[1,5-α]pyrazine-1-carboxylate 6f The crude compound 6e (240 mg, 776.09 μmol) was dissolved in 15 mL of tetrahydrofuran, then compound 2d (150.3 mg, 1.16 mmol) and triethylamine (314.13 mg, 3.10 mmol) were added, followed by addition of bis(trichloromethyl)carbonate (92.12 mg, 310.44 μmol) in an ice bath. The reaction solution was warmed up to room temperature and stirred for 12 hours. The reaction solution was concentrated under reduced pressure, and the resulting residue was purified by thin layer chromatography with developing solvent system A to obtain the title compound 6f (0.19 g, yield: 69.9%).

MS m/z (ESI): 351.1 [M+1].

Step 5

(S)—$N^7$-(3,4-Difluorophenyl)-6-methyl-$N^1$-((R)-1,1,1-trifluoropropan-2-yl)-5,6-dihydroimidazo[1,5-α]pyrazine-1,7(8H)-dicarboxamide 6

Compound 6f (190 mg, 542.36 μmol) was dissolved in 20 mL of tetrahydrofuran, then compound 1e (121.66 mg, 813.54 μmol) was added, followed by dropwise addition of 4 mL of a 1M solution of lithium bis(trimethylsilyl)amide in tetrahydrofuran in an ice bath. After completion of the addition, the reaction solution was stirred for 2 hours. The reaction solution was added with 10 mL of water, and extracted with ethyl acetate (20 mL×2). The organic phases were combined and concentrated under reduced pressure. The resulting residue was purified by preparative high performance liquid chromatography (Waters 2767-SQ Detecor2, elution system: ammonium bicarbonate, water, acetonitrile) to obtain the title compound 6 (25 mg, yield: 10.6%).

MS m/z (ESI): 432.1 [M+1].

$^1$H NMR (400 MHz, DMSO-$d_6$) δ 9.28 (s, 1H), 8.25 (d, 1H), 7.73 (s, 1H), 7.54-7.45 (m, 1H), 7.21-7.15 (m, 2H), 5.27 (s, 1H), 4.95-4.92 (m, 1H), 4.86-4.80 (m, 2H), 4.28-4.22 (m, 2H), 1.50-1.45 (m, 3H), 1.20 (d, 3H).

Step 1

Methyl (S)-5-(((1-hydroxypropan-2-yl)(4-methoxybenzyl)amino)methyl)-1H-imidazole-4-carboxylate 6c (S)-2-((4-Methoxybenzyl)amino)propan-1-ol 6a (34.92 g, 179.08 mmol, prepared according to the known method disclosed in "Bioorganic & Medicinal Chemistry Letters, 2015, 25(5), 1086-1091") was dissolved in 600 mL of tetrahydrofuran, then methyl 5-formylimidazole-4-carboxylate 6b (23 g, 149.23 mmol, prepared according to the method disclosed in the patent application "US2008/318935") was added, followed by addition of sodium triacetoxyborohydride (47.44 g, 223.85 mmol) in batches. After stirring for 12 hours, the reaction solution was filtrated, and the filtrate was concentrated under reduced pressure. The resulting residue was added with 600 mL of ethyl acetate, washed with water (200 mL×2), dried over anhydrous sodium sulfate and filtrated. The filtrate was concentrated under reduced pressure to obtain the crude title compound 6c (40 g), which was used directly in the next step without purification.

MS m/z (ESI): 334.2 [M+1].

Step 2

Methyl (S)-7-(4-methoxybenzyl)-6-methyl-5,6,7,8-tetrahydroimidazo[1,5-α]pyrazine-1-carboxylate 6d The crude compound 6c (11 g, 33.03 mmol) and triphenylphosphine (12.98 g, 49.49 mmol) (Sinopharm Chemical Reagent Co., Ltd.) were dissolved in 400 mL of tetrahydrofuran, followed by slow addition of diisopropyl azodicarboxylate (10 g, 49.45 mmol, Shanghai Accela ChemBio Co., Ltd.) in an ice bath. The reaction solution was warmed up slowly to room temperature, stirred for 12 hours, and concentrated under reduced pressure. The resulting residue was added with 400 mL of ethyl acetate, washed with water (100 mL×2), dried over anhydrous sodium sulfate and

Example 7

(S)—N⁵-(3,4-Difluorophenyl)-6-methyl-N³-((R)-1,1,1-trifluoropropan-2-yl)-6,7-dihydropyrazolo[1,5-α]pyrazine-3,5(4H)-dicarboxamide 7

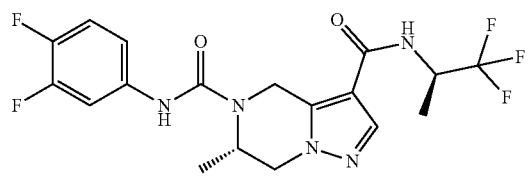

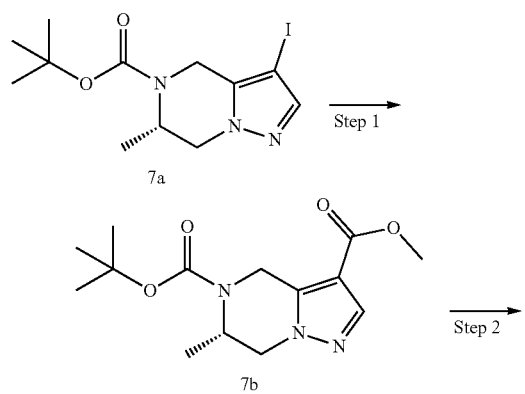

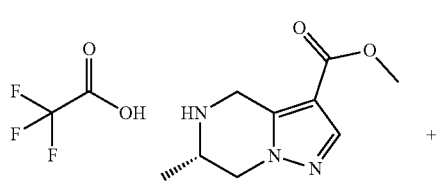

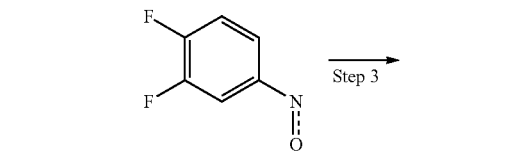

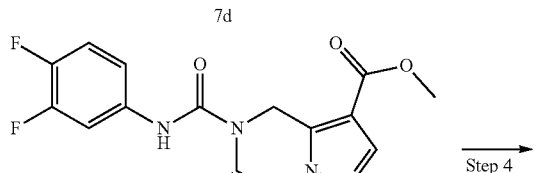

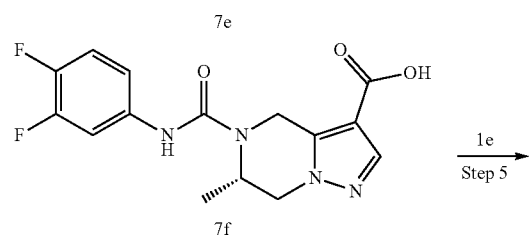

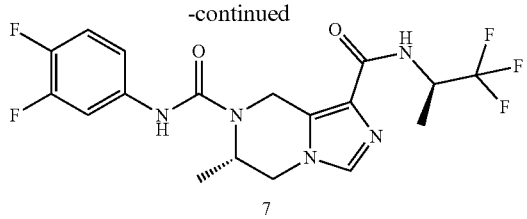

Step 1

5-Tert-butyl 3-methyl (S)-6-methyl-6,7-dihydropyrazolo[1,5-α]pyrazine-3,5(4H)-dicarboxylate 7b Tert-butyl (S)-3-iodo-6-methyl-6,7-dihydropyrazolo[1,5-α]pyrazine-5(4H)-carboxylate 7a (8.3 g, 22.85 mmol, prepared according to the method disclosed in the patent application "WO2016113273A1"), palladium acetate (1.03 g, 4.57 mmol), 1,1'-bis(diphenylphosphino)ferrocene (2.53 g, 4.57 mmol) and triethylamine (9.64 mL, 68.56 mmol) were dissolved in 150 mL of methanol under a carbon monoxide atmosphere. After stirring at 55° C. for 15 hours, the reaction solution was filtrated through celite. The filtrate was concentrated under reduced pressure, and the residue was purified by silica gel column chromatography with eluent system C to obtain the title compound 7b (6.3 g, yield: 93.34%).

Step 2

Methyl (S)-6-methyl-4,5,6,7-tetrahydropyrazolo[1,5-α]pyrazine-3-carboxylate trifluoroacetate 7c Compound 7b (6.3 g, 21.33 mmol) was dissolved in 20 mL of dichloromethane, followed by addition of trifluoroacetic acid (14.1 mL, 190.91 mmol). After stirring for 2 hours, the reaction solution was concentrated under reduced pressure to obtain the crude title compound 7c (14 g), which was used directly in the next step without purification.

MS m/z (ESI): 196.1 [M+1].

Step 3

Methyl (S)-5-((3,4-difluorophenyl)carbamoyl)-6-methyl-4,5,6,7-tetrahydropyrazolo[1,5-α]pyrazine-3-carboxylate 7e The crude compound 7c (2 g, 3.23 mmol) and triethylamine (1.64 g, 16.17 mmol) were dissolved in 20 mL of dichloromethane. After stirring for 10 minutes, the reaction solution was added with 1,2-difluoro-4-isocyanatobenzene (601.87 mg, 3.88 mmol, prepared according to the known method disclosed in "*European Journal of Medicinal Chemistry, 2016, 115, 1–13*") in an ice bath, and reacted for 20 minutes. The reaction solution was warmed up to to room temperature, and stirred for 20 minutes. The reaction solution was purified by silica gel column chromatography with eluent systems C and A successively to obtain the title compound 7e (1 g, yield: 88.27%).

MS m/z (ESI): 351.1 [M+1].

Step 4

(S)-5-((3,4-Difluorophenyl)carbamoyl)-6-methyl-4,5,6,7-tetrahydropyrazolo[1,5-α]pyrazine-3-carboxylic acid 7f

Compound 7e (500 mg, 1.43 mmol) and sodium hydroxide (285.45 mg, 7.14 mmol) were dissolved in 5 mL of a mixed solvent of methanol, tetrahydrofuran and water (V:V:V=2:2:1). The reaction solution was stirred at 40° C. for 1 hour, and then stirred at 35° C. for 15 hours. The reaction solution was concentrated under reduced pressure, added with 10 mL of water, added dropwise with 6 M hydrochloric acid until the pH is 2, and filtrated. The filter cake was collected to obtain the crude title compound 7f (450 mg), which was used directly in the next step without purification.

MS m/z (ESI): 337.4 [M+1].

Step 5

(S)—N⁵-(3,4-Difluorophenyl)-6-methyl-N³-((R)-1,1,1-trifluoropropan-2-yl)-6,7-dihydropyrazolo[1,5-α]pyrazine-3,5(41)-dicarboxamide 7

The crude compound 7f (80 mg, 237.89 μmol), O-(7-azabenzotriazol-1-yl)-N,N,N',N'-tetramethyluronium hexafluorophosphate (67.16 mg, 285.47 μmol) and N,N-diisopropylethylamine (122.98 mg, 951.55 μmol) were dissolved in 3 mL of N,N-dimethylformamide, and reacted for 10 minutes. The reaction solution was added with compound 1e (53.36 mg, 356.83 μmol), and stirred for 3 hours. The reaction solution was concentrated under reduced pressure, and the resulting residue was purified by thin layer chromatography with developing solvent system C. The resulting crude product was purified by preparative high performance liquid chromatography (Waters-2767, elution system: ammonium bicarbonate, water, acetonitrile) to obtain the title compound 7 (70 mg, yield: 68.22%).

MS m/z (ESI): 432.1 [M+1].

$^1$H NMR (400 MHz, CD$_3$OD) δ 8.09 (m, 1H), 7.49-7.47 (m, 1H), 7.16-7.13 (m, 2H), 5.32 (d, 1H), 5.01-4.99 (m, 1H), 4.84-4.80 (m, 1H), 4.66 (d, 1H), 4.32-4.29 (m, 1H), 4.17 (d, 1H), 1.40 (d, 3H), 1.21 (d, 3H).

Example 8

(S)—N³-(Tert-butyl)-N⁵-(3,4-difluorophenyl)-6-methyl-6,7-dihydropyrazolo[1,5-α]pyrazine-3,5(4H)-dicarboxamide 8

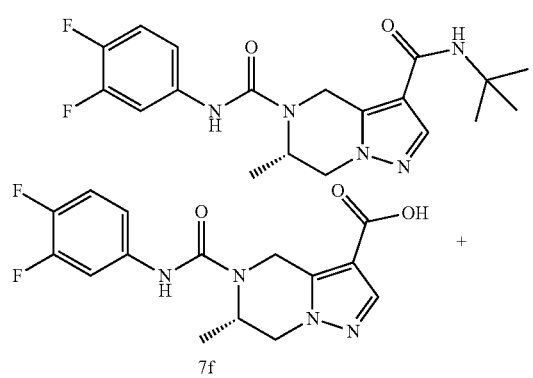

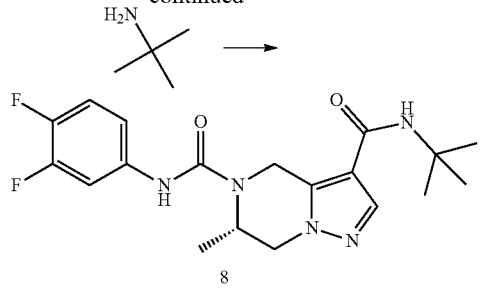

The crude compound 7f (150 mg, 446.04 μmol), O-(7-azabenzotriazol-1-yl)-N,N,N',N'-tetramethyluronium hexafluorophosphate (157.41 mg, 669.06 μmol) and N,N-diisopropylethylamine (230.58 mg, 1.78 mmol) were dissolved in 3 mL of N,N-dimethylformamide, and reacted for 10 minutes. The reaction solution was added with tert-butylamine (48.93 mg, 669.06 μmol), and stirred for 3 hours. The reaction solution was added with 30 mL of water, and extracted with ethyl acetate (30 mL×2). The organic phases were combined and concentrated under reduced pressure, and the resulting residue was purified by thin layer chromatography with developing solvent system C. The resulting crude product was purified by preparative high performance liquid chromatography (Waters-2767, elution system: ammonium bicarbonate, water, acetonitrile) to obtain the title compound 8 (30 mg, yield: 17.18%).

MS m/z (ESI): 392.2 [M+1].

$^1$H NMR (400 MHz, CD$_3$OD) δ 8.02 (s, 1H), 7.53-7.50 (m, 1H), 7.20-7.17 (m, 2H), 5.31 (d, 1H), 5.01-4.98 (m, 1H), 4.68 (d, 1H), 4.33-4.29 (m, 1H), 4.18 (d, 1H), 1.46 (s, 9H), 1.23 (d, 3H).

Example 9

(R)—N⁵-(3-Cyano-4-fluorophenyl)-N³-(1,1,1-trifluoropropan-2-yl)-6,7-dihydropyrazolo[1,5-α]pyrazine-3,5(4H)-dicarboxamide 9

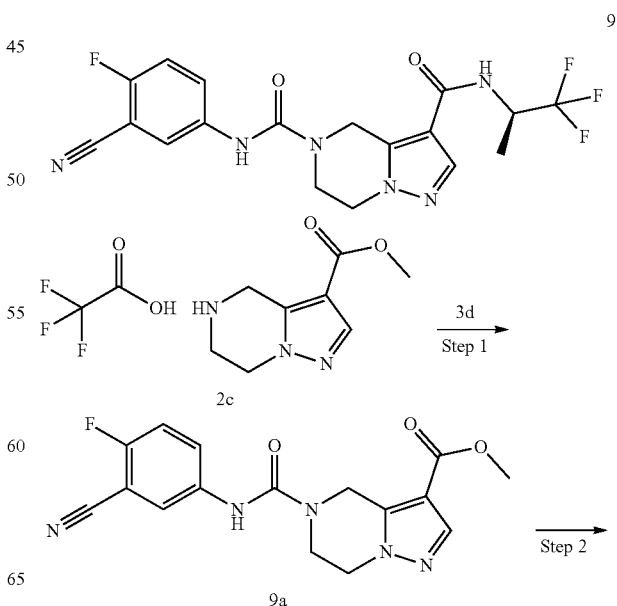

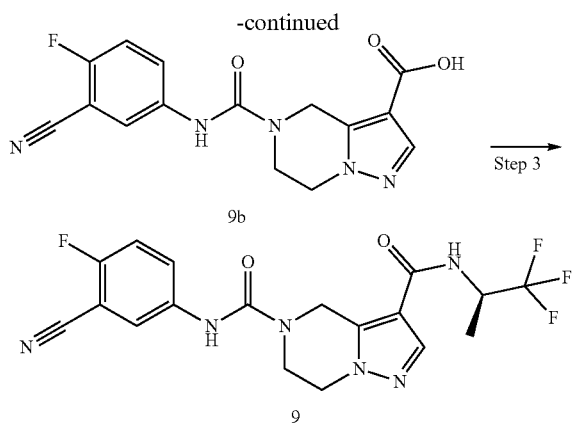

Step 1

Methyl 5-((3-cyano-4-fluorophenyl)carbamoyl)-4,5,6,7-tetrahydropyrazolo[1,5-α]pyrazine-3-carboxylate 9a Compound 2c (50 mg, 275.95 μmol), compound 3d (38.56 mg, 275.95 μmol) and triethylamine (279.23 mg, 2.76 mmol) were dissolved in 10 mL of tetrahydrofuran, followed by addition of bis(trichloromethyl)carbonate (32.76 mg, 110.38 μmol) at 0° C. The reaction solution was warmed up slowly to room temperature, and stirred for 3 hours. The reaction solution was concentrated under reduced pressure, and the resulting residue was purified by thin layer chromatography with developing solvent system A to obtain the title compound 9a (20 mg, yield: 21.1%).

MS m/z (ESI): 344.2 [M+1].

Step 2

5-((3-Cyano-4-fluorophenyl)carbamoyl)-4,5,6,7-tetrahydropyrazolo[1,5-α]pyrazine-3-carboxylic acid 9b Compound 9a (100 mg, 291.28 μmol) was dissolved in 10 mL of methanol, followed by addition of lithium hydroxide (139.52 mg, 5.83 mmol) and 2 mL of water. After stirring for 3 hours, the reaction solution was concentrated under reduced pressure, added with 10 mL of water, and added dropwise with 6 M hydrochloric acid until the pH is 2. The reaction solution was concentrated under reduced pressure to obtain the crude title compound 9b (95.91 mg), which was used directly in the next step without purification.

MS m/z (ESI): 330.1 [M+1].

Step 3

(R)—$N^5$-(3-Cyano-4-fluorophenyl)-$N^3$-(1,1,1-trifluoropropan-2-yl)-6,7-dihydropyrazolo[1,5-α]pyrazine-3,5(4H)-dicarboxamide 9

The crude compound 9b (95.91 mg, 291.28 μmol) was dissolved in 10 mL of N,N-dimethylformamide, then compound 1e (34.34 mg, 303.69 μmol) and triethylamine (92.19 mg, 911.06 μmol) were added, followed by addition of O-(7-azabenzotriazol-1-yl)-N,N,N',N'-tetramethyluronium hexafluorophosphate (85.74 mg, 364.43 μmol) at 0° C. After stirring for 12 hours, the reaction solution was concentrated under reduced pressure, and the resulting residue was purified by preparative high performance liquid chromatography (Waters 2767-SQ Detecor2, elution system: ammonium bicarbonate, water, acetonitrile) to obtain the title compound 9 (5 mg, yield: 3.88%).

MS m/z (ESI): 425.1 [M+1].

$^1$H NMR (400 MHz, CD$_3$OD) δ 8.07 (s, 1H), 7.87-7.85 (m, 2H), 7.32-7.27 (m, 1H), 5.06 (s, 2H), 4.86-4.84 (m, 1H), 4.29-4.27 (m, 2H), 4.06-4.03 (m, 2H), 1.42 (d, 3H).

Example 10

(S)—$N^3$-(Tert-butyl)-6-methyl-$N^5$-(3,4,5-trifluoropheny)-6,7-dihydropyrazolo[1,5-α]pyrazine-3,5(4H)-dicarboxamide 10

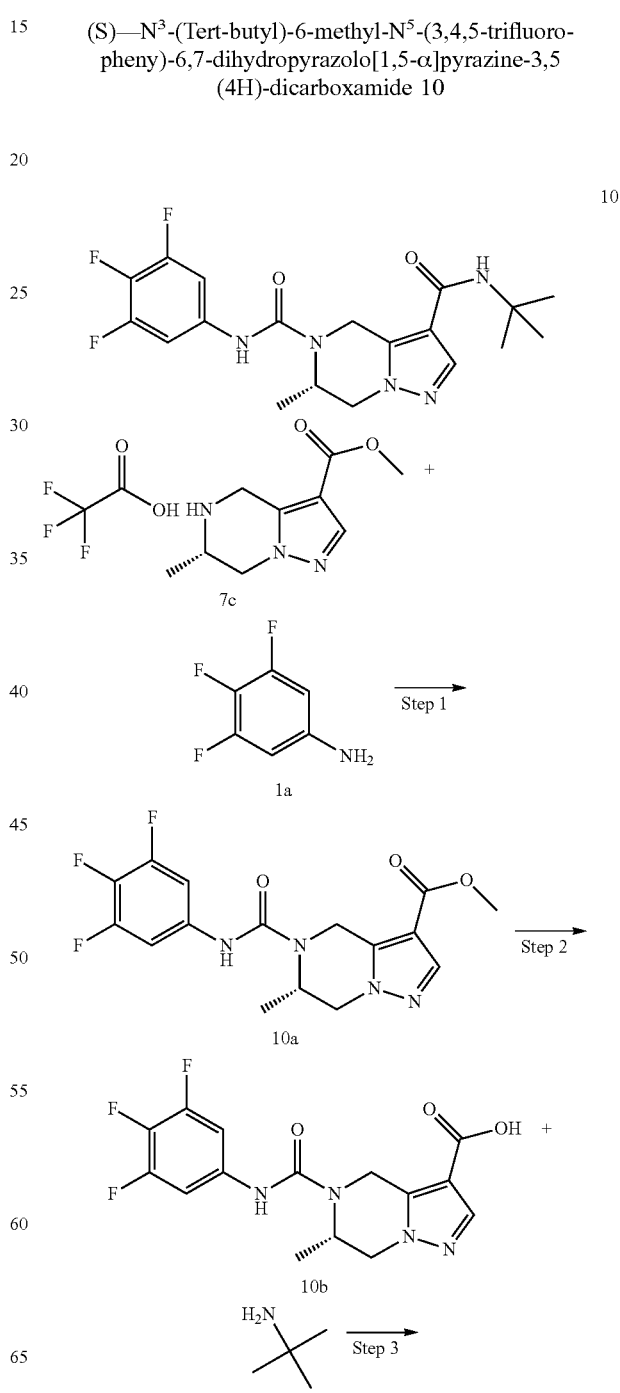

-continued

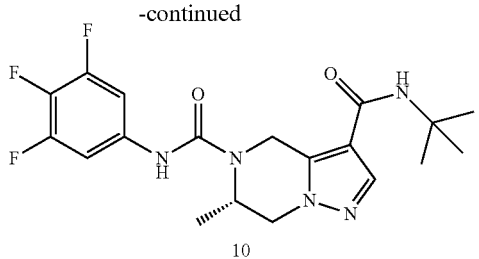

10

Step 1

Methyl (S)-6-methyl-5-((3,4,5-trifluorophenyl)carbamoyl)-4,5,6,7-tetrahydropyrazolo[1,5-α]pyrazine-3-carboxylate 10a Compound 1a (1.17 g, 7.92 mmol) and compound 7c (1.63 g, 5.28 mmol) were dissolved in 30 mL of dichloromethane, followed by addition of triethylamine (2.14 g, 21.22 mmol) and bis(trichloromethyl)carbonate (626.8 mg, 2.11 mmol). After stirring for 2 hours, the reaction solution was concentrated under reduced pressure, and the resulting residue was purified by thin layer chromatography with developing solvent system A to obtain the title compound 10a (730 mg, yield: 37.5%).

MS m/z (ESI): 369.1 [M+1].

Step 2

(S)-6-Methyl-5-((3,4,5-trifluorophenyl)carbamoyl)-4,5,6,7-tetrahydropyrazolo[1,5-α]pyrazine-3-carboxylic acid 10b Compound 10a (730 mg, 1.98 mmol) and sodium hydroxide (396.45 mg, 9.91 mmol) were dissolved in 10 mL of a mixed solvent of methanol, tetrahydrofuran and water (V:V:V=2:2:1). The reaction solution was stirred at 40° C. for 1 hour, and then stirred at 35° C. for 15 hours. The reaction solution was concentrated under reduced pressure, added with 10 mL of water, added dropwise with 6 M hydrochloric acid until the pH is 2, and filtrated. The filter cake was collected to obtain the crude title compound 10b (702 mg, 1.98 mmol), which was used directly in the next step without purification.

MS m/z (ESI): 355.4 [M+1].

Step 3

(S)—N³-(Tert-butyl)-6-methyl-N⁵-(3,4,5-trifluorophenyl)-6,7-dihydropyrazolo[1,5-α]pyrazine-3,5 (4H)-dicarboxamide 10

The crude compound 10b (85 mg, 239.92 μmol), O-(7-azabenzotriazol-1-yl)-N,N,N',N'-tetramethyluronium hexafluorophosphate (67.74 mg, 287.91 μmol), N,N-diisopropylethylamine (129.21 mg, 719.76 μmol) were dissolved in 3 mL of N,N-dimethylformamide, and reacted for 10 minutes. The reaction solution was added with tert-butylamine (35.09 mg, 479.84 μmol), and stirred for 3 hours. The reaction solution was concentrated under reduced pressure, and the resulting residue was purified by thin layer chromatography with developing solvent system C. The resulting crude product was purified by preparative high performance liquid chromatography (Waters-2767, elution system:

ammonium bicarbonate, water, acetonitrile) to obtain the title compound 10 (50 mg, yield: 50.90%).

MS m/z (ESI): 410.2 [M+1].

¹H NMR (400 MHz, CD₃OD) δ 8.00 (s, 1H), 7.30-7.28 (m, 2H), 5.31 (d, 1H), 4.98-4.96 (m, 1H), 4.69 (d, 1H), 4.31-4.27 (m, 1H), 4.17 (d, 1H), 1.44 (s, 9H), 1.22 (d, 3H).

Example 11

(S)—N⁷-(3-Cyano-4-fluorophenyl)-6-methyl-N¹-((R)-1,1,1-trifluoropropan-2-yl)-5,6-dihydroimidazo [1,5-α]pyrazine-1,7-(8H)-dicarboxamide 11

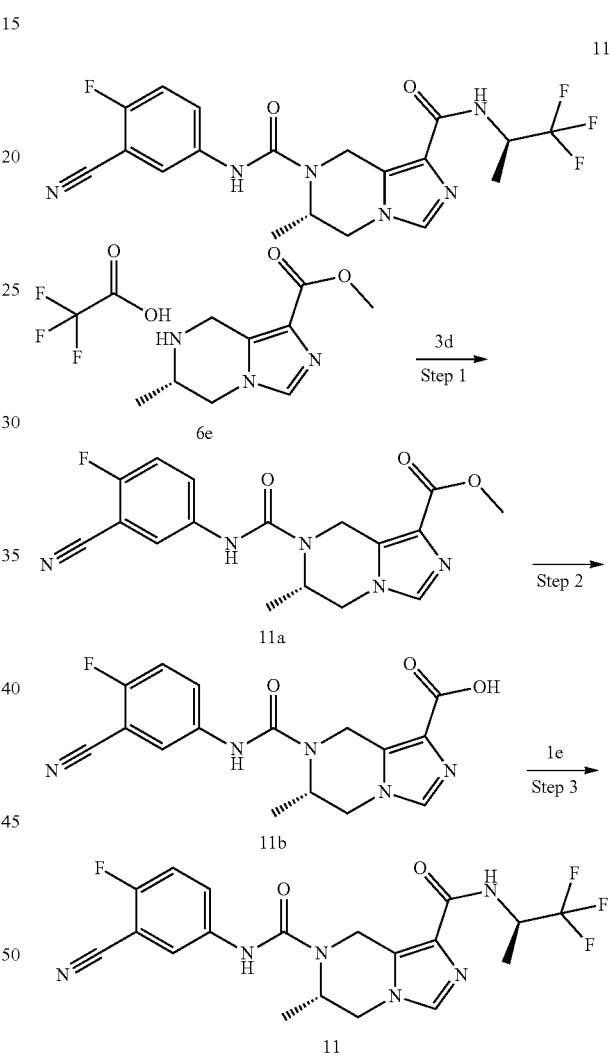

Step 1

Methyl (S)-7-((3-cyano-4-fluorophenyl)carbamoyl)-6-methyl-5,6,7,8-tetrahydroimidazo[1,5-α]pyrazine-1-carboxylate 11a The crude compound 6e (9.2 g, 47.13 mmol) was dissolved in 50 mL of tetrahydrofuran, then compound 3d (6.5 g, 47.13 mmol) and triethylamine (5.82 g, 56.55 mmol) were added, followed by addition of bis(trichloromethyl)carbonate (4.9 g, 16.49 mmol) at 0° C. The reaction solution was warmed up slowly to room temperature and stirred for 12 hours. The reaction solution was filtrated, and the filtrate was concentrated under reduced pressure to obtain the crude title compound 11a (16.84 g), which was used directly in the next step without purification.

MS m/z (ESI): 358.1 [M+1].

Step 2

(S)-7-((3-Cyano-4-fluorophenyl)carbamoyl)-6-methyl-5,6,7,8-tetrahydroimidazo[1,5-α]pyrazine-1-carboxylic acid 11b The crude compound 11a (16.84 g, 47.13 mmol) was dissolved in 50 mL of methanol, followed by dropwise addition of a pre-formulated sodium hydroxide solution (dissolving sodium hydroxide (12 g, 282.76 mmol) in 60 mL of water) at 0° C. The reaction solution was warmed up slowly to room temperature, and stirred for 4 hours. The reaction solution was concentrated under reduced pressure to remove the organic solvent. The resulting residue was washed with dichloromethane, and the pH of the aqueous phase was adjusted to 1-2 with 6 M hydrochloric acid. The solution was concentrated under reduced pressure to obtain the crude title compound 11b (16.18 g), which was used directly in the next step without purification.

MS m/z (ESI): 344.1 [M+1].

Step 3

(S)—N⁷-(3-Cyano-4-fluorophenyl)-6-methyl-N¹-((R)-1,1,1-trifluoropropan-2-yl)-5,6-dihydroimidazo[1,5-α]pyrazine-1,7-(8H)-dicarboxamide 11

The crude compound 11b (13 g, 37.87 mmol), compound 1e (7.4 g, 49.23 mmol) and triethylamine (11.6 g, 113.6 mmol) were dissolved in 200 mL of N,N-dimethylformamide. After cooling to 0° C., the reaction solution was added with O-(7-azabenzotriazol-1-yl)-N,N,N',N'-tetramethyluronium hexafluorophosphate (29 g, 75.73 mmol). The reaction solution was warmed up slowly to room temperature, and stirred for 12 hours. The reaction solution was added with 300 mL of ethyl acetate, and washed with water (100 mL×3). The organic phase was concentrated under reduced pressure, and the resulting residue was purified by preparative high performance liquid chromatography (Waters 2767-SQ Detecor2, elution system: ammonium bicarbonate, water, acetonitrile) to obtain the title compound 11 (1.8 g, yield: 10.8%).

MS m/z (ESI): 439.0 [M+1].

¹H NMR (400 MHz, CD₃OD) δ 7.87-7.85 (m, 1H), 7.73-7.70 (m, 2H), 7.69-7.27 (m, 1H), 5.30-5.26 (d, 1H), 4.83-4.82 (m, 1H), 4.85-4.72 (m, 2H), 4.23-4.21 (m, 2H), 1.43 (d, 3H), 1.20 (d, 3H).

Example 12

(S)—N¹-(Tert-butyl)-N⁷-(3,4-difluorophenyl)-6-methyl-5,6-dihydroimidazo[1,5-α]pyrazine-1,7-(8H)-dicarboxamide 12

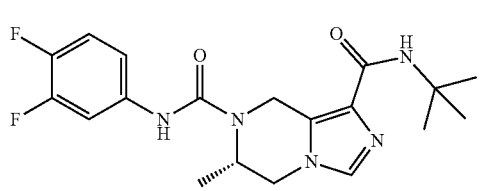

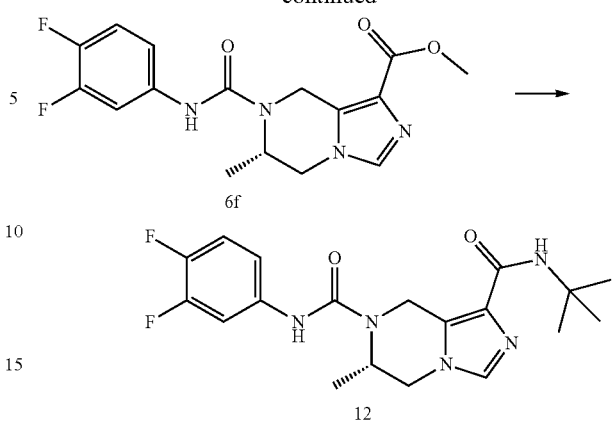

Compound 6f (2.11 g, 6.27 mmol) was dissolved in 15 mL of tetrahydrofuran, then tert-butylamine (600 mg, 8.16 mmol) was added, followed by dropwise addition of a 1 M solution of lithium bis(trimethylsilyl)amide in tetrahydrofuran (5 g, 31.37 mmol) at 0° C. After stirring for 2 hours, the reaction solution was added with 100 mL of water, and extracted with ethyl acetate (100 mL×3). The organic phases were combined, dried over anhydrous sodium sulfate and filtrated. The filtrate was concentrated under reduced pressure, and the resulting residue was purified by preparative high performance liquid chromatography (Waters 2767-SQ Detecor2, elution system: ammonium bicarbonate, water, acetonitrile) to obtain the title compound 12 (120 mg, yield: 4.9%).

MS m/z (ESI): 392.1 [M+1].

¹H NMR (400 MHz, CD₃OD) δ 7.65 (s, 1H), 7.50-7.49 (m, 1H), 7.19-7.17 (m, 2H), 5.25-5.21 (d, 1H), 4.92-4.90 (m, 1H), 4.77-4.73 (m, 1H), 4.20-4.18 (m, 2H), 1.46 (s, 9H), 1.19-1.17 (d, 3H).

Example 13

(S)-6-Methyl-N¹-(3-methyloxetan-3-yl)-N⁷-(3,4,5-trifluorophenyl)-5,6-dihydroimidazo[1,5-α]pyrazine-1,7(8H)-dicarboxamide 13

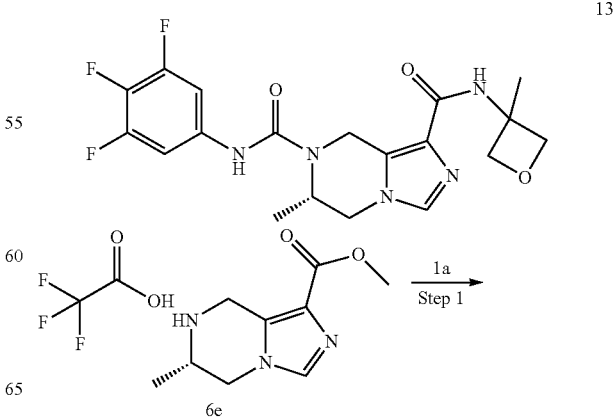

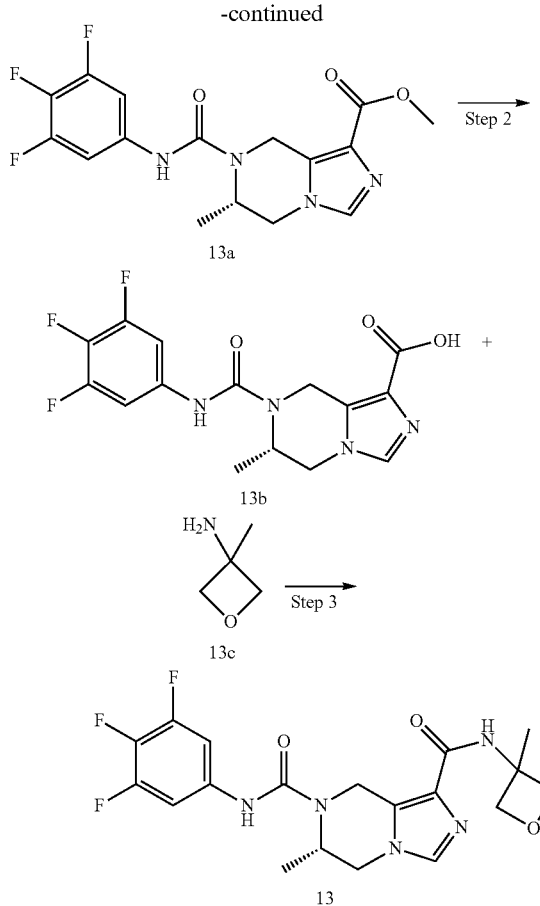

reduced pressure to obtain the crude title compound 13b (75 mg), which was used directly in the next step without purification.

MS m/z (ESI): 355.0 [M+1].

Step 3

(S)-6-Methyl-$N^1$-(3-methyloxetan-3-yl)-$N^7$-(3,4,5-trifluorophenyl)-5,6-dihydroimidazo[1,5-α]pyrazine-1,7(8H)-dicarboxamide 13

The crude compound 13b (75 mg, 211.69 μmol) was dissolved in 10 mL of N,N-dimethylformamide, then 3-methyl-3-amino-oxetane 13c (27.66 mg, 317.53 μmol, Shanghai Shuya Pharmaceutical Technology Co. Ltd.) and triethylamine (64.26 mg, 635.07 μmol) were added, followed by addition o O-(7-azabenzotriazol-1-yl)-N,N,N',N'-tetramethyluronium hexafluorophosphate (99.61 mg, 423.38 μmol) at 0° C. After stirring at room temperature for 12 hours, the reaction solution was concentrated under reduced pressure, and the resulting residue was purified by preparative high performance liquid chromatography (Waters 2767-SQ Detecor2, elution system: ammonium bicarbonate, water, acetonitrile) to obtain the title compound 13 (16 mg, yield: 17.9%).

MS m/z (ESI): 424.0 [M+1].

$^1$H NMR (400 MHz, DMSO-$d_6$) δ 8.87 (s, 1H), 8.36 (s, 1H), 7.68 (s, 1H), 7.33-7.27 (m, 2H), 5.27-5.20 (m, 1H), 4.92 (d, 2H), 4.73 (d, 2H), 4.78-4.73 (m, 1H), 4.52 (d, 2H), 4.26-4.20 (m, 2H), 1.73 (s, 3H), 1.20 (d, 3H).

Example 14

(S)-6-Methyl-$N^3$-(3-methyloxetan-3-yl)-$N^5$-(3,4,5-trifluorophenyl)-6,7-dihydropyrazolo[1,5-α]pyrazine-3,5(41)-dicarboxamide 14

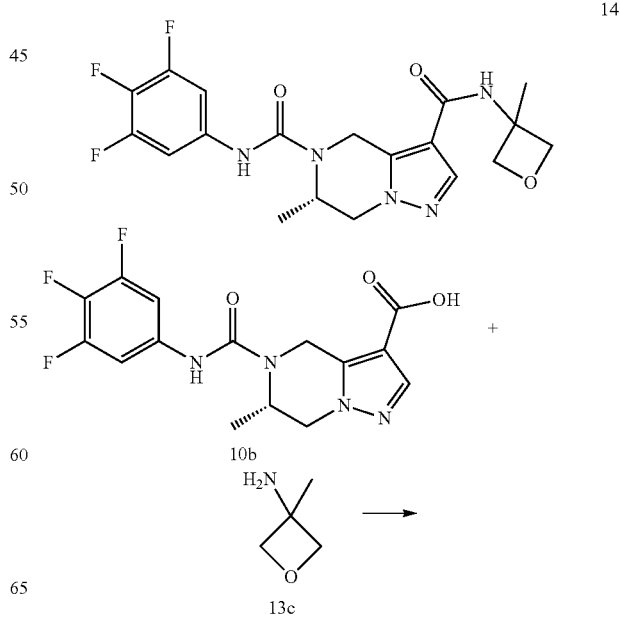

Step 1

Methyl (S)-6-methyl-7-((3,4,5-trifluorophenyl)carbamoyl)-5,6,7,8-tetrahydroimidazo[1,5-α]pyrazine-1-carboxylate 13a The crude compound 6e (140.00 mg, 452.72 μmol) was dissolved in 15 mL of tetrahydrofuran, then compound 1a (99.89 mg, 679.08 μmol) and triethylamine (183.24 mg, 1.81 mmol) were added, followed by addition of bis(trichloromethyl)carbonate (53.74 mg, 181.09 μmol) at 0° C. The reaction solution was warmed up slowly to room temperature and stirred for 12 hours. The reaction solution was concentrated under reduced pressure, and the resulting residue was purified by thin layer chromatography with developing solvent system A to obtain the title compound 13a (88 mg, yield: 52.8%).

MS m/z (ESI): 369.1 [M+1].

Step 2

(S)-6-Methyl-7-((3,4,5-trifluorophenyl)carbamoyl)-5,6,7,8-tetrahydroimidazo[1,5-α]pyrazine-1-carboxylic acid 13b Compound 13a (75 mg, 203.63 μmol) was dissolved in 10 mL of methanol, followed by addition of sodium hydroxide (81.45 mg, 2.04 mmol) and 2 mL of water. After stirring for 3 hours, the reaction solution was concentrated under -continued

14

The crude compound 10b (100 mg, 282.26 μmol), compound 13e (36.89 mg, 423.39 mol) and N,N-diisopropylethylamine (42.84 mg, 423.39 μmol) were dissolved in 10 mL of N,N-dimethylformamide, followed by addition of O-(7-azabenzotriazol-1-yl)-N,N,N',N'-tetramethyluronium hexafluorophosphate (79.69 mg, 338.71 μmol). After stirring for 1 hour, the reaction solution was concentrated under reduced pressure, and the resulting residue was purified by thin layer chromatography with developing solvent system A. The resulting crude product was purified by preparative high performance liquid chromatography (Waters-2767, elution system: ammonium bicarbonate, water, acetonitrile) to obtain the title compound 14 (80 mg, yield: 66.94%).

MS m/z (ESI): 424.5 [M+1].

$^1$H NMR (400 MHz, DMSO-$d_6$) δ 8.89 (s, 1H), 8.37 (s, 1H), 7.99 (s, 1H), 7.33-7.17 (m, 2H), 5.33 (d, 1H), 5.00-4.98 (m, 1H), 4.88 (d, 2H), 4.71 (d, 1H), 4.52 (d, 2H), 4.34-4.31 (m, 1H), 4.21-4.18 (m, 1H), 1.72 (s, 3H), 1.25 (d, 3H).

Example 15

(S)—$N^5$-(3-Cyano-4-fluorophenyl)-6-methyl-$N^3$-((R)-1,1,1-trifluoropropan-2-yl)-6,7-dihydropyrazolo[1,5-α]pyrazine-3,5(4H)-dicarboxamide 15

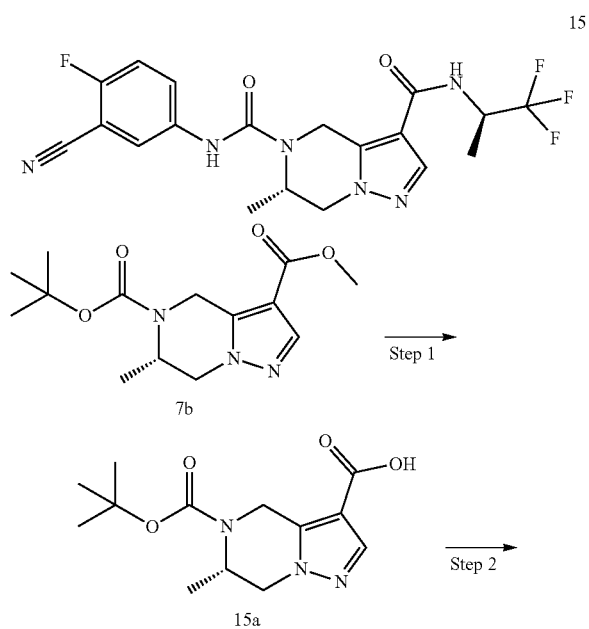

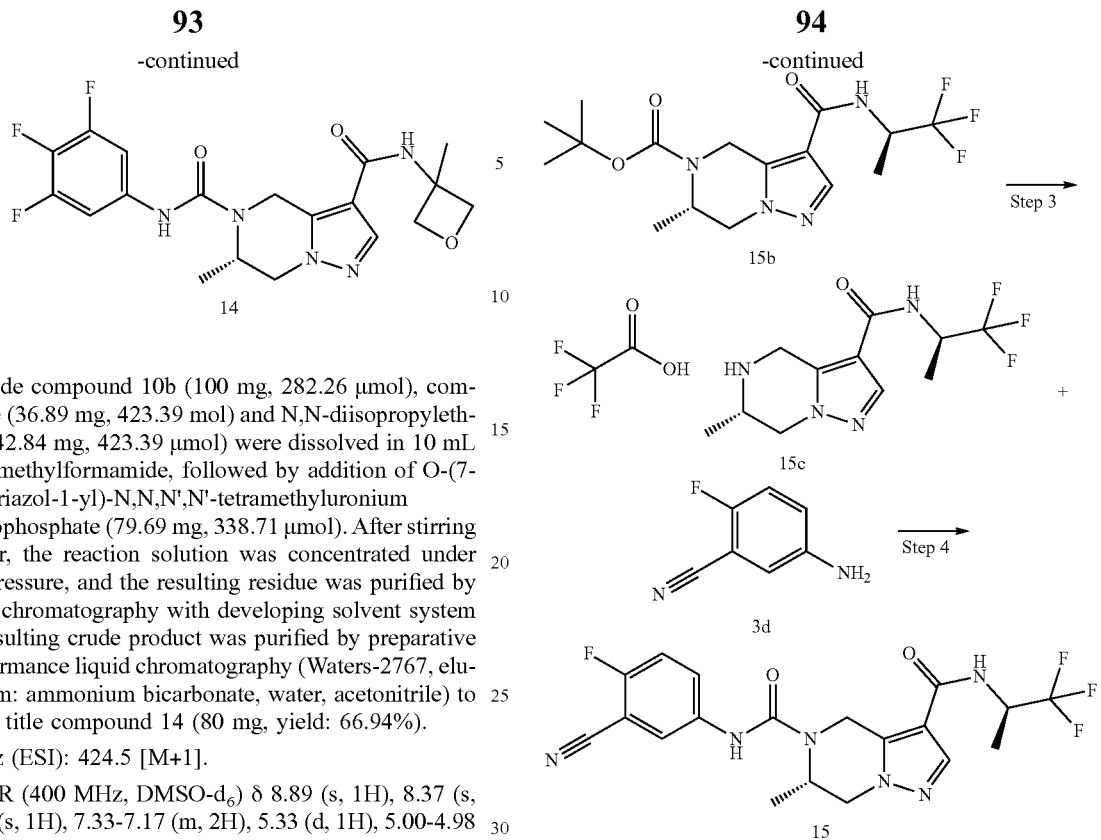

Step 1

(S)-5-(Tert-butoxycarbonyl)-6-methyl-4,5,6,7-tetrahydropyrazolo[1,5-α]pyrazine-3-carboxylic acid 15a Compound 7b (525 mg, 1.78 mmol) and lithium hydroxide monohydrate (373 mg, 8.9 mmol) were dissolved in 10 mL of a mixed solvent of methanol, tetrahydrofuran and water (V:V:V=2:2:1). After stirring for 16 hours, the reaction solution was concentrated under reduced pressure, added with 10 mL of water, added dropwise with 6 M hydrochloric acid until the pH is 2, and extracted with ethyl acetate (20 mL×2). The organic phases were combined, and concentrated under reduced pressure to obtain the crude title compound 15a (500 mg), which was used directly in the next step without purification.

MS m/z (ESI): 282.2 [M+1].

Step 2

Tert-butyl (S)-6-methyl-3-(((R)-1,1,1-trifluoropropan-2-yl)carbamoyl)-6,7-dihydropyrazolo[1,5-α]pyrazine-5(41)-carboxylate 15b The crude compound 15a (500 mg, 1.78 mmol), compound 1e (479 mg, 3.2 mmol) and N,N-diisopropylethylamine (360 mg, 3.56 mmol) were dissolved in 20 mL of N,N-dimethylformamide, followed by addition of O-(7-azabenzotriazol-1-yl)-N,N,N',N'-tetramethyluronium hexafluorophosphate (628 mg, 2.67 mmol). After stirring for 2 hours, the reaction solution was concentrated under reduced pressure, and the resulting residue was purified by thin layer chromatography with developing solvent system A to obtain the title compound 15b (600 mg, yield: 89.56%).

MS m/z (ESI): 377.2 [M+1].

Step 3

(S)-6-Methyl-N—((R)-1,1,1-trifluoropropan-2-yl)-4,5,6,7-tetrahydropyrazolo[1,5-α]pyrazine-3-carboxamide trifluoroacetate 15c Compound 15b (500 mg, 1.33 mmol) was dissolved in 20 mL of dichloromethane, followed by addition of trifluoroacetic acid (758 mg, 6.65 mmol). After stirring for 2 hours, the reaction solution was concentrated under reduced pressure to obtain the crude title compound 15c (500 mg), which was used directly in the next step without purification.

MS m/z (ESI): 277.2 [M+1].

Step 4

(S)—N⁵-(3-Cyano-4-fluorophenyl)-6-methyl-N³-((R)-1,1,1-trifluoropropan-2-yl)-6,7-dihydropyrazolo[1,5-α]pyrazine-3,5(41)-dicarboxamide 15

The crude compound 15c (50 mg, 128 μmol) was dissolved in 10 mL of tetrahydrofuran, then compound 3d (26 mg, 192 μmol) and triethylamine (26 mg, 256 mol) were added, followed by addition of bis(trichloromethyl)carbonate (13 mg, 45 mol) at 0° C. The reaction solution was warmed up to room temperature and stirred for 1 hour. The reaction solution was concentrated under reduced pressure, and the resulting residue was purified by thin layer chromatography with developing solvent system A. The resulting crude product was purified by preparative high performance liquid chromatography (Waters-2767, elution system: ammonium bicarbonate, water, acetonitrile) to obtain the title compound 15 (20 mg, yield: 35.61%).

MS m/z (ESI): 439.2 [M+1].

$^1$H NMR (400 MHz, CDCl$_3$) δ 7.87-7.86 (m, 1H), 7.83 (s, 1H), 7.70-7.68 (m, 1H), 7.42 (s, 1H), 7.20-7.16 (m, 1H), 6.01 (d, 1H), 5.34-5.23 (m, 2H), 4.92-4.89 (m, 1H), 4.84 (d, 1H), 4.38-4.34 (m, 1H), 4.25 (d, 1H), 1.49 (d, 3H), 1.27 (d, 3H).

Example 16

(S)—N⁵-(2,6-Difluoropyridin-4-yl)-6-methyl-N³-((R)-1,1,1-trifluoropropan-2-yl)-6,7-dihydropyrazolo[1,5-α]pyrazine-3,5(4H)-dicarboxamide 16

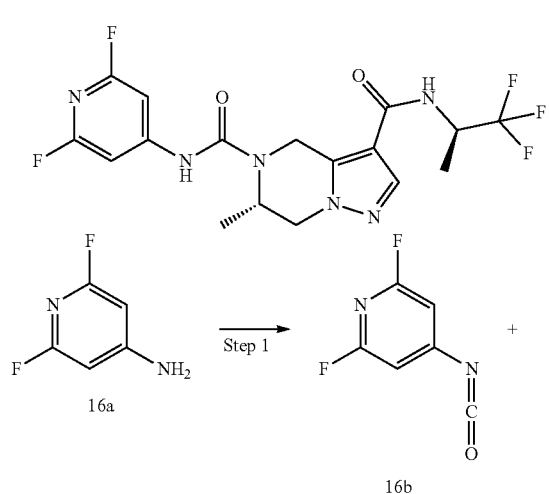

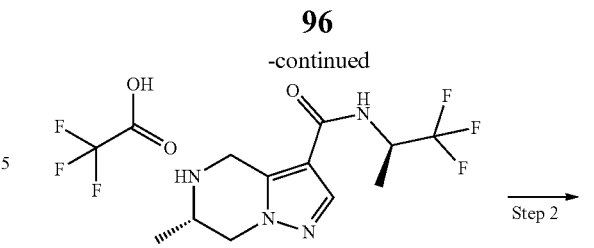

Step 1

2,6-Difluoro-4-isocyanatopyridine 16b 2,6-Difluoro-4-aminopyridine 16a (500 mg, 3.84 mmol) and N,N-diisopropylethylamine (583 mg, 5.76 mmol) were dissolved in 25 mL of toluene, followed by addition of bis(trichloromethyl)carbonate (297 mg, 4.61 mmol). After stirring at 110° C. for 4 hours, the reaction solution was concentrated under reduced pressure to obtain the crude title compound 16b (1 g), which was used directly in the next step without purification.

Step 2

(S)—N⁵-(2,6-Difluoropyridin-4-yl)-6-methyl-N³-((R)-1,1,1-trifluoropropan-2-yl)-6,7-dihydropyrazolo[1,5-α]pyrazine-3,5(41)-dicarboxamide 16

The crude compound 15c (100 mg, 256 μmol) was dissolved in 10 mL of dichloromethane, followed by addition of the crude compound 16b (80 mg) and triethylamine (78 mg, 769 μmol). After stirring for 2 hours, the reaction solution was concentrated under reduced pressure, and the resulting residue was purified by thin layer chromatography with developing solvent system A. The resulting crude product was purified by preparative high performance liquid chromatography (Waters-2767, elution system: ammonium bicarbonate, water, acetonitrile) to obtain the title compound 16 (20 mg, yield: 18.05%).

MS m/z (ESI): 433.5 [M+1].

$^1$H NMR (400 MHz, CDCl$_3$) δ 8.19 (s, 1H), 7.84 (s, 1H), 7.31 (s, 1H), 7.10 (s, 1H), 6.05 (d, 1H), 5.34 (d, 1H), 5.27-5.25 (m, 1H), 4.90-4.88 (m, 1H), 4.84 (d, 1H), 4.38-4.34 (m, 1H), 4.28 (d, 1H), 1.48 (d, 3H), 1.29 (d, 3H).

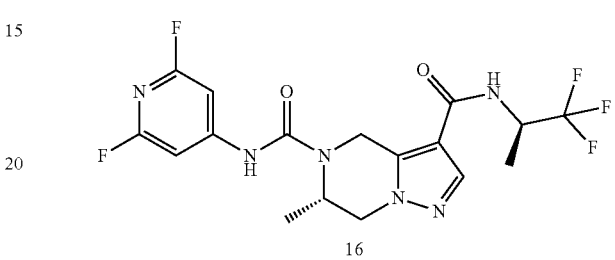

Example 17

(R)—N⁵-(3,4,5-Trifluorophenyl)-N³-(1,1,1-trifluoropropan-2-yl)-6,7-dihydro-[1,2,3]triazolo[1,5-α]pyrazine-3,5(4)-dicarboxamide 17

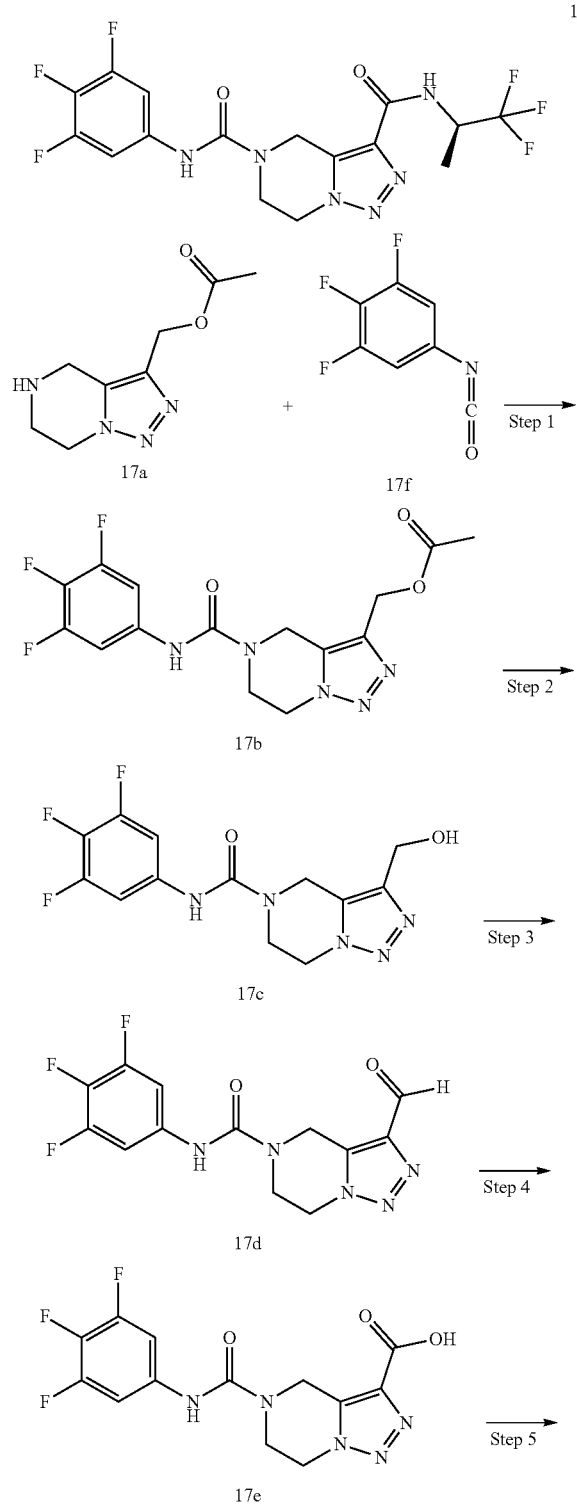

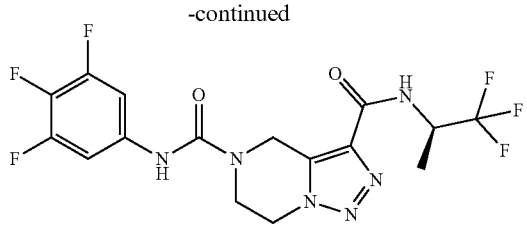

Step 1

(5-((3,4,5-Trifluorophenyl)carbamoyl)-4,5,6,7-tetrahydro-[1,2,3]triazolo[1,5-α]pyrazin-3-yl)methyl acetate 17b (4,5,6,7-Tetrahydro-[1,2,3]triazolo[1,5-α]pyrazin-3-yl)methyl acetate 17a (350 mg, 2 mmol, prepared according to the known method disclosed in *"Journal of Medicine Chemistry,* 2014, 57(9), 3687-3706") and diisopropylethylamine (790 mg, 6 mmol) were dissolved in 20 mL of dichloromethane. After stirring for 10 minutes, the reaction solution was added with 1,2,3-trifluoro-5-isocyanatobenzene 17f (400 mg, 2 mmol, J&K Scientific Co. Ltd.) in an ice bath and reacted for 20 minutes, then warmed up to room temperature and stirred for 20 minutes. The reaction solution was concentrated under reduced pressure, and purified by silica gel column chromatography with eluent systems C and A to obtain the title compound 17b (190 mg, yield: 25.24%).

MS m/z (ESI): 370.1 [M+1].

Step 2

3-(Hydroxymethyl)-N-(3,4,5-trifluorophenyl)-6,7-dihydro-[1,2,3]triazolo[1,5-α]pyrazine-5(41H)-carboxamide 17c Compound 17b (190 mg, 0.51 mmol) was dissolved in 5 mL of a mixed solvent of methanol and water (V:V=4:1), followed by addition of lithium hydroxide (108 mg, 2.57 mmol). After stirring for 2 hours, the reaction solution was added with 20 mL of water, and extracted with ethyl acetate (15 mL×3). The organic phases were combined, and concentrated under reduced pressure to obtain the crude title compound 17c (65 mg), which was used directly in the next step without purification.

MS m/z (ESI): 328.1 [M+1].

Step 3

3-Formyl-N-(3,4,5-trifluorophenyl)-6,7-dihydro-[1,2,3]triazolo[1,5-α]pyrazine-5(4H)-carboxamide 17d The crude compound 17c (65 mg, 0.2 mmol) was dissolved in 5 mL of dichloromethane, followed by addition of pyridinium chlorochromate (138 mg, 0.64 mmol) and silica gel (140 mg, 100-200 mesh). After stirring for 3 hours, the reaction solution was filtrated and concentrated under reduced pressure, and the resulting residue was purified by thin layer chromatography with developing solvent system A to obtain the title compound 17d (30 mg, yield: 43.12%).

MS m/z (ESI): 326.1 [M+1].

Step 4

5-((3,4,5-Trifluorophenyl)carbamoyl)-4,5,6,7-tetrahydro-[1,2,3]triazolo[1,5-α]pyrazine-3-carboxylic acid 17e Compound 17d (30 mg, 0.1 mmol) was dissolved in 5 mL of a mixed solvent of acetonitrile and water (V:V=3:2), followed by addition of sulfamic acid (20 mg, 0.2 mmol). After stirring for 10 minutes, the solution was added with sodium chlorite (20 mg, 0.2 mmol), and stirred for 2 hours. The reaction solution was added with 0.5 mL of saturated sodium sulfite solution and 10 mL of water successively, and extracted with ethyl acetate (10 mL×3). The organic phases were combined, and concentrated under reduced pressure to obtain the crude compound 17e (25 mg), which was used directly in the next step without purification.

MS m/z (ESI): 342.1 [M+1].

Step 5

(R)—N$^5$-(3,4,5-Trifluorophenyl)-N$^3$-(1,1,1-trifluoropropan-2-yl)-6,7-dihydro-[1,2,3]triazolo[1,5-α]pyrazine-3,5(4H)-dicarboxamide 17

The crude compound 17e (25 mg, 73.2 μmol), O-(7-azabenzotriazol-1-yl)-N,N,N',N'-tetramethyluronium hexafluorophosphate (35 mg, 146.5 μmol) and N,N-diisopropylethylamine (47 mg, 366.2 μmol) were dissolved in 3 mL of N,N-dimethylformamide, and reacted for 10 minutes. The reaction solution was added with compound 1e (33 mg, 220 μmol), and stirred for 3 hours. The reaction solution was concentrated under reduced pressure, and the resulting residue was purified by thin layer chromatography with developing solvent system C to obtain the title compound 17 (5 mg, yield: 15.6%).

MS m/z (ESI): 437.1 [M+1].
$^1$H NMR (400 MHz, CD$_3$OD) δ 7.29-7.27 (m, 2H), 4.60 (br, 1H), 4.54 (t, 2H), 4.04 (t, 2H), 2.80 (s, 2H), 1.45 (d, 3H).

Example 18

(S)-6-Methyl-N$^7$-(3,4,5-trifluorophenyl)-N$^1$-((R)-1,1,1-trifluoropropan-2-yl)-5,6-dihydroimidazo[1,5-α]pyrazine-1,7(8l)-dicarboxamide 18

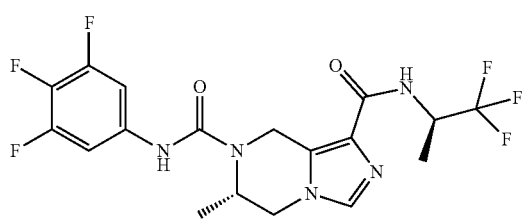

In accordance with the synthetic route of Example 6, the starting compound 2d in Step 4 was replaced with the starting compound 1a, accordingly, the title compound 18 (2.8 mg) was prepared.

MS m/z (ESI): 450.2 [M+1].

$^1$H NMR (400 MHz, DMSO-d$_6$) δ 8.86 (s, 1H), 8.33 (d, 1H), 7.73 (s, 1H), 7.33-7.28 (m, 2H), 5.29 (d, 1H), 4.92 (d, 1H), 4.85-4.76 (m, 2H), 4.28-4.22 (m, 2H), 1.44 (d, 3H), 1.34 (d, 3H).

Example 19

N$^3$-(3-Methyloxetan-3-yl)-N$^5$-(3,4,5-trifluorophenyl)-6,7-dihydropyrazolo[1,5-α]pyrazine-3,5(4H)-dicarboxamide 19

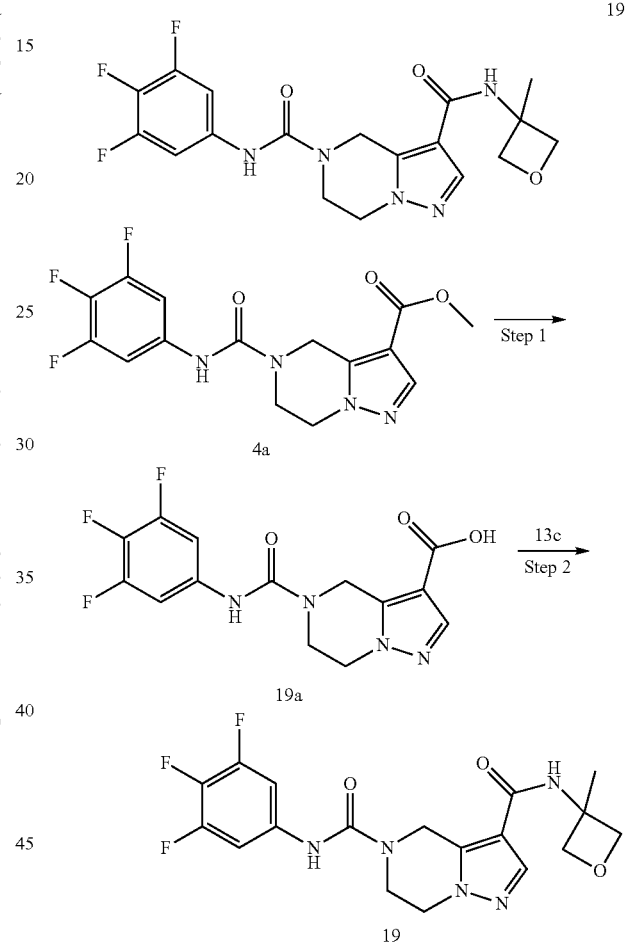

Step 1

5-((3,4,5-Trifluorophenyl)carbamoyl)-4,5,6,7-tetrahydropyrazolo[1,5-α]pyrazine-3-carboxylic acid 19a Compound 4a (3 g, 8.74 mmol) was dissolved in 20 mL of methanol and 20 mL of tetrahydrofuran, followed by addition of sodium hydroxide (3.39 g, 84.67 mmol) and 10 mL of water. After stirring for 16 hours, the reaction solution was concentrated under reduced pressure, added with 20 mL of water, and added dropwise with 6M hydrochloric acid until the pH is 2. The reaction solution was concentrated under reduced pressure to obtain the crude title compound 19a (100 mg), which was used directly in the next step without purification.

MS m/z (ESI): 341.1 [M+1].

Step 2

N³-(3-Methyloxetan-3-yl)-N⁵-(3,4,5-trifluorophenyl)-6,7-dihydropyrazolo[1,5-α]pyrazine-3,5(41H)-dicarboxamide 19

The crude compound 19a (100 mg, 293.90 μmol), O-(7-azabenzotriazol-1-yl)-N,N,N',N'-tetramethyluronium hexafluorophosphate (69.14 mg, 293.90 μmol) and triethylamine (29.74 mg, 293.90 μmol) were dissolved in 5 mL of N,N-dimethylformamide, and reacted for 10 minutes. The reaction solution was added with compound 13e (108.96 mg, 881.69 μmol), and stirred for 3 hours. The reaction solution was added with 10 mL of water, and extracted with ethyl acetate (20 mL×2). The organic phases were combined and concentrated under reduced pressure, and the resulting residue was purified by thin layer chromatography with developing solvent system C. The resulting crude product was purified by preparative high performance liquid chromatography (Waters-2767, elution system: ammonium bicarbonate, water, acetonitrile) to obtain the title compound 19 (20 mg, yield: 16.62%).

MS m/z (ESI): 410.1 [M+1].

¹H NMR (400 MHz, CD₃OD) δ 7.95 (s, 1H), 7.30-7.26 (m, 2H), 5.01 (s, 2H), 4.88 (d, 2H), 4.50 (d, 2H), 4.28-4.25 (m, 2H), 4.04-4.01 (m, 2H), 1.71 (s, 3H).

Example 20

(S)—N⁷-(2,6-Difluoropyridin-4-yl)-6-methyl-N¹-((R)-1,1,1-trifluoropropan-2-yl)-5,6-dihydroimidazo[1,5-α]pyrazine-1,7-(8)-dicarboxamide 20

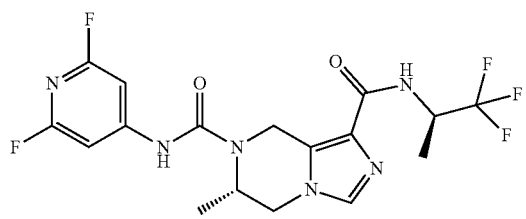

In accordance with the synthetic route of Example 6, the starting compound 2d in Step 4 was replaced with the starting compound 2,6-difluoro-4-pyridylamine (Shanghai Bide Pharmatech Ltd.), accordingly, the title compound 20 (10 mg) was prepared.

MS m/z (ESI): 433.1 [M+1].

¹H NMR (400 MHz, CD₃OD) δ 7.69 (s, 1H), 7.11-7.09 (d, 2H), 5.33-5.29 (m, 1H), 4.97-4.77 (m, 1H), 4.56-4.41 (m, 1H), 4.27-4.21 (m, 1H), 3.80-3.45 (m, 2H), 1.38 (d, 3H), 1.15 (d, 3H).

Example 21

(R)—N³-(Sec-butyl)-N⁵-(3,4,5-trifluorophenyl)-6,7-dihydropyrazol[1,5-α]pyrazine-3,5(41H)-dicarboxamide 21

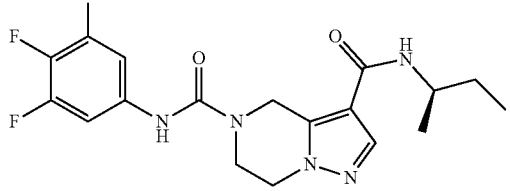

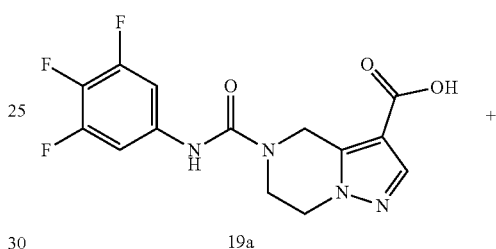

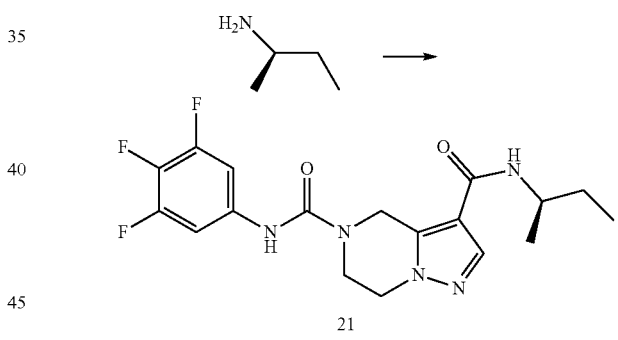

The crude compound 19a (96 mg, 282.26 μmol) was dissolved in 10 mL of N,N-dimethylformamide, then (R)-but-2-amine (20.64 mg, 282.26 μmol, TCI (Shanghai) Development Co., Ltd.) and triethylamine (85.69 mg, 846.78 μmol) were added, followed by addition of O-(7-azabenzotriazol-1-yl)-N,N,N',N'-tetramethyluronium hexafluorophosphate (79.69 mg, 338.71 μmol) at 0° C. The reaction solution was warmed up to room temperature and reacted for 12 hours. The reaction solution was concentrated under reduced pressure, and the resulting residue was purified by preparative high performance liquid chromatography (Waters 2767-SQ Detecor2, elution system: ammonium bicarbonate, water, acetonitrile) to obtain the title compound 21 (10 mg, yield: 8.96%).

MS m/z (ESI): 396.1 [M+1].

¹H NMR (400 MHz, CD₃OD) δ 8.00 (s, 1H), 7.30-7.26 (m, 2H), 5.04 (s, 2H), 4.27-4.25 (m, 2H), 4.04-4.00 (m, 3H), 1.60-1.56 (m, 2H), 1.22 (d, 3H), 0.96 (t, 3H).

Example 22

(S)—N³-((R)-Sec-butyl)-N⁵-(3,4-difluorophenyl)-6-methyl-6,7-dihydropyrazolo[1,5-α]pyrazine-3,5(4H)-dicarboxamide 22

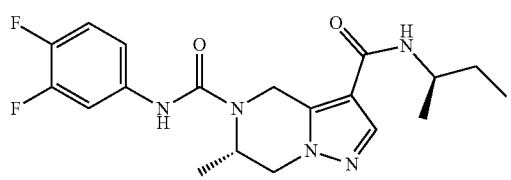

In accordance with the synthetic route of Example 7, the starting compound 1e was replaced with the starting compound (R)-but-2-amine, accordingly, the title compound 22 (20 mg) was prepared.

MS m/z (ESI): 392.1 [M+1].

¹H NMR (400 MHz, CDCl₃) δ 7.69 (s, 1H), 7.53-7.50 (m, 1H), 7.23 (s, 1H), 7.06-7.02 (m, 2H), 5.62 (d, 1H), 5.23 (d, 2H), 4.82 (d, 1H), 4.31-4.28 (m, 1H), 4.28 (d, 1H), 4.07 (d, 1H), 1.60-1.57 (m, 2H), 1.22 (d, 6H), 0.99 (t, 3H).

Example 23

(S)—N⁵-(3,4-Difluorophenyl)-N³-isopropyl-6-methyl-6,7-dihydropyrazolo[1,5-α]pyrazine-3,5(41H)-dicarboxamide 23

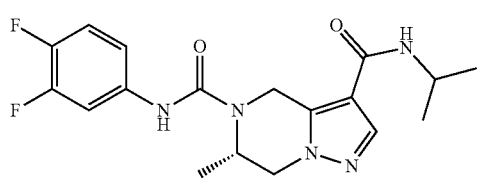

In accordance with the synthetic route of Example 7, the starting compound 1e in Step 5 was replaced with the starting compound isopropylamine, accordingly, the title compound 23 (25 mg) was prepared.

MS m/z (ESI): 378.1 [M+1].

¹H NMR (400 MHz, CD₃OD) δ 8.00 (s, 1H), 7.50-7.45 (m, 1H), 7.18-7.14 (m, 2H), 5.35-5.30 (m, 1H), 4.99-4.95 (m, 1H), 4.69-4.62 (m, 1H), 4.32-4.22 (m, 1H), 4.22-4.12 (m, 2H), 1.23-1.16 (m, 9H).

Example 24

(S)—N⁵-(3,4-Difluorophenyl)-N³-(1-methoxy-2-methylpropan-2-yl)-6-methyl-6,7-dihydropyrazolo[1,5-α]pyrazine-3,5(4H)-dicarboxamide 24

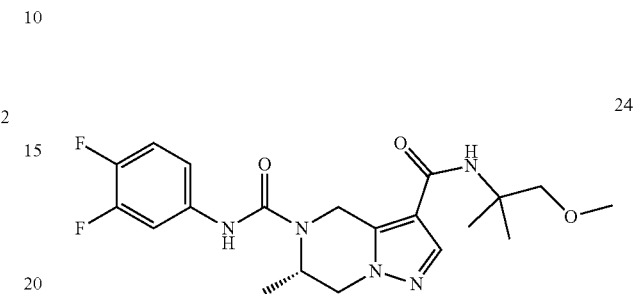

In accordance with the synthetic route of Example 7, the starting compound 1e in Step 5 was replaced with the starting compound 1-methoxy-2-methylpropane-2-amine (Sinopharm Chemical Reagent Co., Ltd. (Shanghai)), accordingly, the title compound 24 (15 mg) was prepared.

MS m/z (ESI): 422.1 [M+1].

¹H NMR (400 MHz, CDCl₃) δ 7.69 (s, 1H), 7.56-7.51 (m, 1H), 7.15-7.09 (m, 3H), 6.13 (s, 1H), 5.26-5.22 (m, 1H), 5.20 (d, 1H), 4.85 (d, 1H), 4.36-4.32 (m, 1H), 4.22 (d, 1H), 3.47 (s, 3H), 3.44 (s, 2H), 1.50 (s, 6H), 1.25 (d, 3H).

Example 25

(S)—N⁵-(3-Chloro-2-fluoropyridin-4-yl)-6-methyl-N³-((R)-1,1,1-trifluoropropan-2-yl)-6,7-dihydropyrazolo[1,5-α]pyrazine-3,5 (41)-dicarboxamide 25

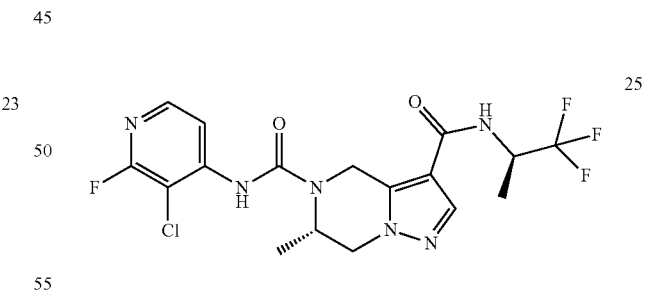

In accordance with the synthetic route of Example 3, the starting compound 3a in Step 1 was replaced with the starting compound 7b, the starting compound 3d in Step 3 was replaced with the starting compound 2-chloro-3-fluoropyridine-4-amine (Shanghai Bide Pharmatech Ltd.), accordingly, the title compound 25 (20 mg) was prepared.

MS m/z (ESI): 449.1 [M+1].

¹H NMR (400 MHz, CD₃OD) δ 8.09 (s, 1H), 8.04 (d, 1H), 7.87 (t, 1H), 5.42 (d, 1H), 5.02 (t, 1H), 4.84 (t, 1H), 4.77 (d, 1H), 4.38-4.35 (m, 1H), 4.21 (d, 1H), 1.41 (d, 3H), 1.29 (d, 3H).

Example 26

(R)—N¹-(Sec-butyl)-N⁷-(3,4,5-trifluorophenyl)-5,6-dihydroimidazo[1,5-α]pyrazine-1,7(8H)-dicarboxamide 26

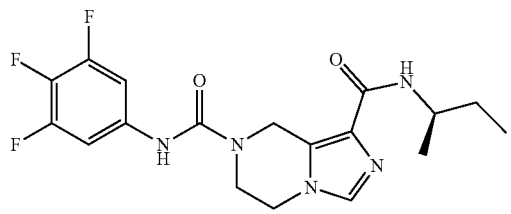

In accordance with the synthetic route of Example 1, the starting compound 1e in Step 3 was replaced with the starting compound (R)-but-2-amine, accordingly, the title compound 26 (4 mg) was prepared.

MS m/z (ESI): 396.2 [M+1].

¹H NMR (400 MHz, CD₃OD) δ 7.68 (s, 1H), 7.31-7.29 (m, 2H), 5.05 (s, 2H), 4.23-4.21 (m, 2H), 4.01-3.95 (m, 3H), 1.61-1.58 (m, 2H), 1.24-1.23 (m, 3H), 0.96 (t, 3H).

Example 27

(S)—N³-(Tetrahydrofuran-3-yl)-N⁵-(3,4,5-trifluorophenyl)-6,7-dihydropyrazolo[1,5-α]pyrazine-3,5(4H)-dicarboxamide 27

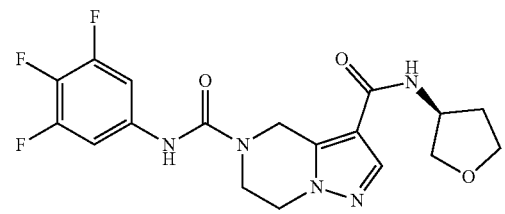

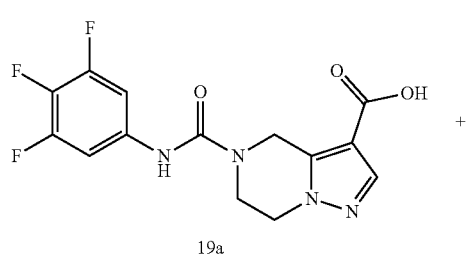

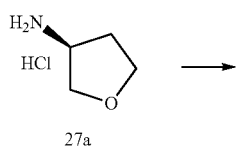

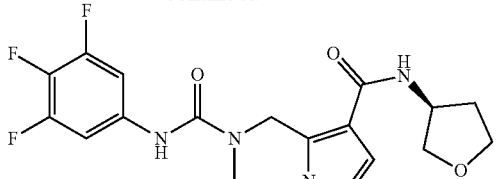

The crude compound 19a (100 mg, 293.90 mol), O-(7-azabenzotriazol-1-yl)-N,N,N',N'-tetramethyluronium hexafluorophosphate (138.29 mg, 587.79 μmol) and triethylamine (148.70 mg, 1.47 mmol) were dissolved in 3 mL of N,N-dimethylformamide, and reacted for 10 minutes. The reaction solution was added with (S)-tetrahydrofuran-3-amine hydrochloride 27a (72.64 mg, 587.79 μmol, Shanghai Bide Pharmatech Ltd.), and stirred for 3 hours. The reaction solution was added with 10 mL of water, and extracted with ethyl acetate (20 mL×2). The organic phases were combined and concentrated under reduced pressure, and the resulting residue was purified by thin layer chromatography with developing solvent system C. The resulting crude product was purified by preparative high performance liquid chromatography (Waters-2767, elution system: ammonium bicarbonate, water, acetonitrile) to obtain the title compound 27 (20 mg, yield: 16.62%).

MS m/z (ESI): 410.1 [M+1].

¹H NMR (400 MHz, CD₃OD) δ 8.02 (s, 1H), 7.30-7.26 (m, 2H), 5.03 (s, 2H), 4.56-4.55 (m, 1H), 4.27-4.25 (m, 2H), 4.04-3.95 (m, 4H), 3.85-3.84 (m, 1H), 3.72-3.71 (m, 1H), 2.32-2.27 (m, 1H), 2.02-1.96 (m, 1H).

Example 28

(S)—N⁵-(3,4-Difluorophenyl)-N³-(1-hydroxy-2-methylpropan-2-yl)-6-methyl-6,7-dihydropyrazolo[1,5-α]pyrazine-35(4H)-dicarboxamide 28

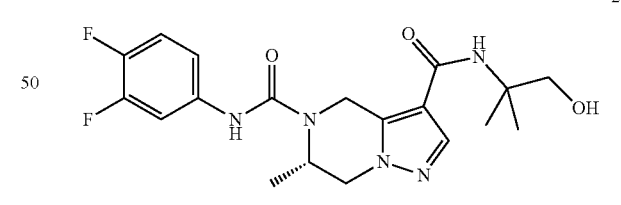

In accordance with the synthetic route of Example 7, the starting compound 1e in Step 5 was replaced with the starting compound 2-amino-2-methylpropane-1-ol (Accela ChemBio Inc), accordingly, the title compound 28 (10 mg) was prepared.

MS m/z (ESI): 408.1 [M+1].

¹H NMR (400 MHz, CDCl₃) δ 7.70 (s, 1H), 7.57-7.52 (m, 1H), 7.16-7.10 (m, 3H), 5.94 (s, 1H), 5.25-5.23 (m, 1H), 5.22 (d, 1H), 4.83 (d, 1H), 4.59-4.58 (m, 1H), 4.37-4.32 (m, 1H), 4.21 (d, 1H), 3.77-3.69 (m, 2H), 1.45 (s, 6H), 1.25 (d, 3H).

Example 29

(R)—N⁵-(3,4-Difluorophenyl)-2-methyl-N³-(1,1,1-trifluoropropan-2-yl)-6,7-dihydropyrazolo[1,5-α]pyrazine-3,5(4H)-dicarboxamide 29

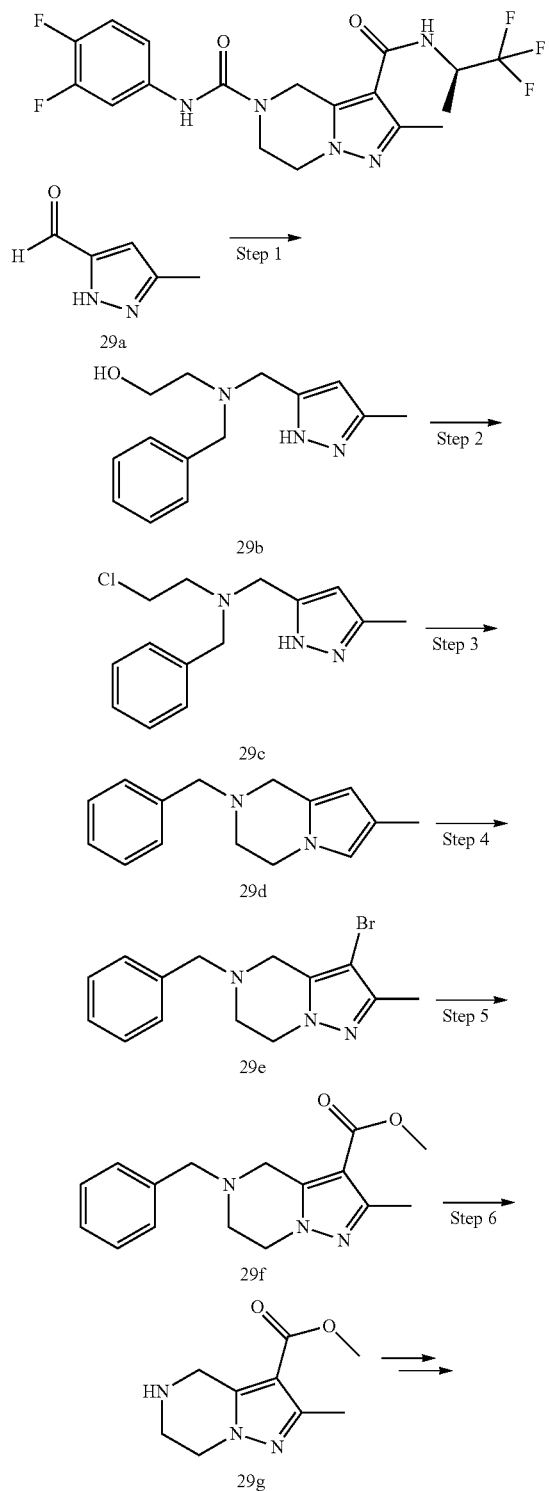

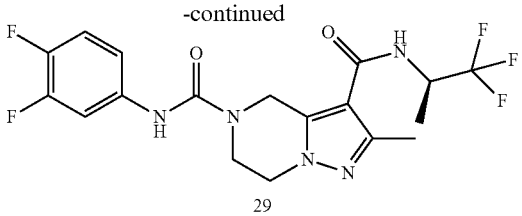

Step 1

2-(Benzyl((3-methyl-1H-pyrazol-5-yl)methyl)amino)ethan-1-ol 29b

3-Methyl-1H-pyrazole-5-carbaldehyde 29a (5.1 g, 45.41 mmol, Shanghai Bide Pharmatech Ltd.) was dissolved in 100 mL of dichloromethane, followed by addition of 2-(benzylamino)ethanol (6.87 g, 45.41 mmol). After stirring for 1 hours, the reaction solution was added with sodium borohydride acetate (9.62 g, 45.41 mmol), and stirred for 16 hours. The reaction solution was concentrated under reduced pressure, and the resulting residue was purified by silica gel column chromatography with eluent systems C and A to obtain the title compound 29b (11 g, yield: 98.75%).

MS m/z (ESI): 246.1 [M+1].

Step 2

N-Benzyl-2-chloro-N-((3-methyl-1H-pyrazol-5-yl)methyl)ethan-1-amine 29c

Compound 29b (11 g, 44.84 mmol) was dissolved in 200 mL of dichloromethane. After cooling to 0° C., the reaction solution was added dropwise with dichlorosulfoxide (16.00 g, 134.52 mmol), and reacted at 40° C. for 16 hours. The reaction solution was cooled to room temperature, and concentrated under reduced pressure to obtain the crude title compound 29c (11.8 g), which was used directly in the next step without purification.

MS m/z (ESI): 264.1 [M+1].

Step 3

5-Benzyl-2-methyl-4,5,6,7-tetrahydropyrazolo[1,5-α]pyrazine 29d

The crude compound 29c (11.8 g, 44.74 mmol) was dissolved in 200 mL of acetonitrile. After cooling to 0° C., the reaction solution was added with triethylamine (46 g, 447.37 mmol), and reacted at 80° C. for 16 hours. The reaction solution was cooled to room temperature, and concentrated under reduced pressure. The residue was added with 100 mL of water, and extracted with ethyl acetate (200 mL×2). The organic phases were combined, and concentrated under reduced pressure obtain the crude title compound 29d (10.17 g), which was used directly in the next step without purification.

MS m/z (ESI): 228.1 [M+1].

Step 4

5-Benzyl-3-bromo-2-methyl-4,5,6,7-tetrahydropyrazolo[1,5-α]pyrazine 29e

The crude compound 29d (228 mg, 1.0 mmol) was dissolved in 10 mL of acetonitrile, followed by addition of N-bromosuccinimide (180 mg, 1.0 mmol) at 0° C. The reaction solution was warmed up slowly to room temperature, and stirred for 16 hours. The reaction solution was concentrated under reduced pressure, and the resulting residue was purified by thin layer chromatography with developing solvent system A to obtain the title compound 29e (185 mg, yield: 60.6%).

MS m/z (ESI): 306.1 [M+1].

Step 2

Methyl 5-benzyl-2-methyl-4,5,6,7-tetrahydropyrazolo[1,5-α]pyrazine-3-carboxylate 29f Dicobalt octacarbonyl (226 mg, 662 μmol) and potassium carbonate (457 mg, 3.31 mmol) were added to 10 mL of methanol under a carbon monoxide atmosphere. After stirring at 60° C. for 45 minutes, the reaction solution was added with compound 29e (100 mg, 327 μmol) and methyl 2-chloroacetate (215 mg, 1.98 mmol), and stirred for 16 hours. The reaction solution was concentrated under reduced pressure, added with 100 mL of ethyl acetate, filtrated, and washed with 100 mL of ethyl acetate. The filtrate was concentrated under reduced pressure, and the resulting residue was purified by thin layer chromatography with developing solvent system A to obtain the title compound 29f (60 mg, yield: 64.39%).

MS m/z (ESI): 286.2 [M+1].

Step 3

Methyl 2-methyl-4,5,6,7-tetrahydropyrazolo[1,5-α]pyrazine-3-carboxylate 29g

Compound 29f (60 mg, 210.28 μmol) was dissolved in 10 mL of methanol under a hydrogen atmosphere, followed by addition of palladium-carbon hydrogenation catalyst (wet) (22.38 mg, 210.28 μmol). After stirring for 16 hours, the reaction solution was filtrated. The filtrate was concentrated under reduced pressure to obtain the crude title compound 29g (30 mg), which was used directly in the next step without purification.

MS m/z (ESI): 196.2 [M+1].

In accordance with the synthetic route of Example 2, the starting compound 2c in Step 3 was replaced with the crude starting compound 29g, accordingly, the title compound 29 (10 mg) was prepared.

MS m/z (ESI): 432.2[M+1].

$^1$H NMR (400 MHz, CD$_3$OD) δ 7.49-7.44 (m, 1H), 7.19-7.14 (m, 2H), 4.96 (s, 2H), 4.87-4.83 (m, 1H), 4.20-4.17 (m, 2H), 4.01-3.96 (m, 2H), 2.40 (s, 3H), 1.42-1.39 (m, 3H).

Example 30

N$^1$-(3-Methyloxetan-3-yl)-N$^7$-(3,4,5-trifluorophenyl)-5,6-dihydroimidazo[1,5-α]pyrazine-1,7(8H)-dicarboxamide 30

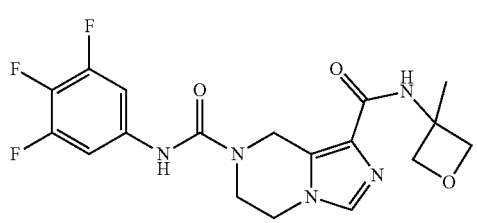

In accordance with the synthetic route of Example 1, the starting compound 1e in Step 5 was replaced with the starting compound 13c, accordingly, the title compound 30 (5 mg) was prepared.

MS m/z (ESI): 410.0 [M+1].

$^1$H NMR (400 MHz, DMSO-d$_6$) δ 8.39 (s, 1H), 7.80 (s, 1H), 7.67 (s, 1H), 7.31-7.26 (m, 2H), 5.02 (s, 2H), 4.54-4.51 (d, 2H), 4.23-4.20 (m, 2H), 3.96-3.93 (m, 2H), 3.57-3.53 (m, 2H), 1.72 (s, 3H).

Example 31

(R)—N$^5$-(3,4-Difluorophenyl)-N$^3$-(1,1,1-trifluoropropan-2-yl)-6,7-dihydro-[1,2,3]triazolo[1,5-α]pyrazine-3,5(4H)-dicarboxamide 31

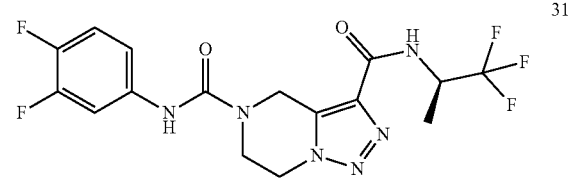 [SMILES: C[C@@H](NC(=O)c1nnn2c1CN(C(=O)Nc1ccc(F)c(F)c1)CC2)C(F)(F)F]

In accordance with the synthetic route of Example 17, the starting compound 17f in Step 1 was replaced with the starting compound 7d, accordingly, the title compound 31 (20 mg) was prepared.

MS m/z (ESI): 419.1 [M+1].

$^1$H NMR (400 MHz, CDCl$_3$) δ 8.11 (s, 1H), 8.09 (s, 1H), 7.56-7.52 (m, 1H), 7.13-7.08 (m, 1H), 7.06 (br, 1H), 5.35-5.32 (m, 1H), 4.99 (s, 1H), 4.94 (s, 1H), 4.68 (s, 2H), 2.26 (t, 2H), 1.42 (d, 3H).

Example 32

(R)—N$^7$-(2,6-Difluoropyridin-4-yl)-N$^1$-(1,1,1-trifluoropropan-2-yl)-5,6-dihydroimidazo[1,5-α]pyrazine-1,7(8H)-dicarboxamide 32

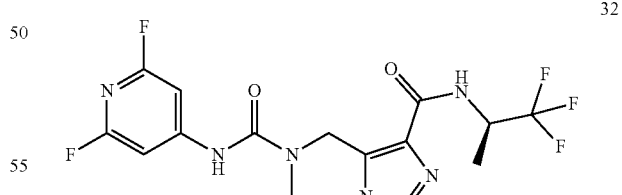

In accordance with the synthetic route of Example 16, the starting compound 15c in Step 2 was replaced with the starting compound 3c, accordingly, the title compound 32 (25 mg) was prepared.

MS m/z (ESI): 419.1 [M+1].

$^1$H NMR (400 MHz, DMSO-d$_6$) δ 8.79 (s, 1H), 8.33 (s, 1H), 7.70 (s, 1H), 7.10 (s, 2H), 5.08 (s, 2H), 4.84-4.80 (m, 1H), 4.26-4.23 (m, 2H), 3.99-3.96 (m, 2H), 1.44 (d, 3H).

Example 33

(S)-6-Methyl-$N^5$-(3,4,5-trifluorophenyl)-$N^3$-((R)-1,1,1-trifluoropropan-2-yl)-6,7-dihydropyrazolo[1,5-α]pyrazine-3,5(41)-dicarboxamide 33

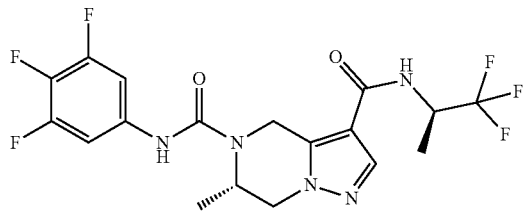

In accordance with the synthetic route of Example 7, the starting compound 7d in Step 3 was replaced with compound 17f, accordingly, the title compound 33 (20 mg) was prepared.

MS m/z (ESI): 450.0 [M+1].

$^1$H NMR (400 MHz, CD$_3$OD) δ 8.09 (s, 1H), 7.30-7.27 (m, 2H), 5.36 (d, 1H), 4.98-4.95 (m, 1H), 4.83-4.80 (m, 1H), 4.70 (d, 1H), 4.31-4.27 (m, 1H), 4.20 (d, 1H), 1.41 (d, 3H), 1.22 (d, 3H).

Example 34

(S)—$N^5$-(3,4-Difluorophenyl)-6-methyl-$N^3$—((S)-tetrahydrofuran-3-yl)-6,7-dihydropyrazolo[1,5-α]pyrazine-3,5(41)-dicarboxamide 34

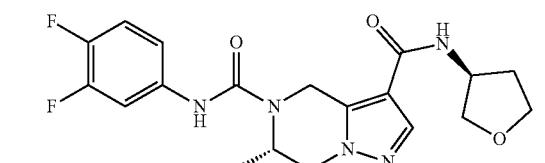

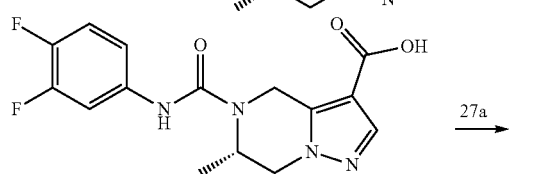

The crude compound 7f (150 mg, 446.04 μmol), O-(7-azabenzotriazol-1-yl)-N,N,N',N'-tetramethyluronium hexafluorophosphate (157.41 mg, 669.06 μmol) and N,N-diisopropylethylamine (230.58 mg, 1.78 mmol) were dissolved in 3 mL of N,N-dimethylformamide, and reacted for 10 minutes. The reaction solution was added with compound 27a (82.3 mg, 669.06 μmol), and stirred for 3 hours. The reaction solution was added with 30 mL of water, and extracted with ethyl acetate (30 mL×2). The organic phases were combined and concentrated under reduced pressure, and the resulting residue was purified by thin layer chromatography with developing solvent system C. The resulting crude product was purified by preparative high performance liquid chromatography (Waters-2767, elution system: ammonium bicarbonate, water, acetonitrile) to obtain the title compound 34 (30 mg, yield: 16.54%).

MS m/z (ESI): 406.2 [M+1].

$^1$H NMR (400 MHz, CD$_3$OD) δ 8.05 (s, 1H), 7.52-7.47 (m, 1H), 7.20-7.17 (m, 2H), 5.33 (d, 1H), 5.00-4.99 (m, 1H), 4.70 (d, 1H), 4.56-4.54 (m, 1H), 4.34-4.32 (m, 1H), 4.21-4.20 (m, 1H), 4.04-3.95 (m, 2H), 3.85-3.83 (m, 1H), 3.73-3.72 (m, 1H), 2.32-2.27 (m, 1H), 2.01-1.94 (m, 3H), 1.24 (d, 1H).

Example 35

$N^1$-(3-Methyltetrahydrofuran-3-yl)-$N^7$-(3,4,5-trifluorophenyl)-5,6-dihydroimidazo[1,5-α]pyrazine-1,7-(81H)-dicarboxamide 35

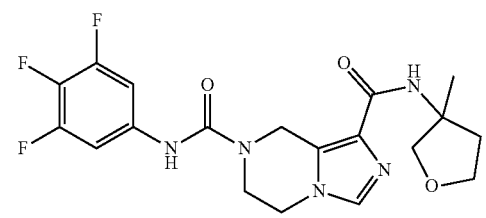

In accordance with the synthetic route of Example 1, the starting compound 1e in Step 5 was replaced with the starting compound 3-methyltetrahydrofuran-3-amine (Shanghai Bide Pharmatech Ltd.), accordingly, the title compound 35 (16 mg) was prepared.

MS m/z (ESI): 424.1 [M+1].

1H NMR (400 MHz, DMSO-d$_6$) δ 8.87 (s, 1H), 8.35 (s, 1H), 7.67 (s, 1H), 7.31-7.27 (m, 2H), 5.03 (s, 2H), 4.21 (t, 2H), 4.10 (d, 1H), 3.96-3.92 (m, 4H), 3.75 (d, 1H), 2.46-2.41 (m, 1H), 2.09-2.01 (m, 1H), 1.59 (s, 3H).

Example 36

(R)—$N^2$-(3,4-Difluorophenyl)-$N^8$-(1,1,1-trifluoropropan-2-yl)-3,4-dihydropyrrolo[1,2-α]pyrazine-2,8(1H)-dicarboxamide 36

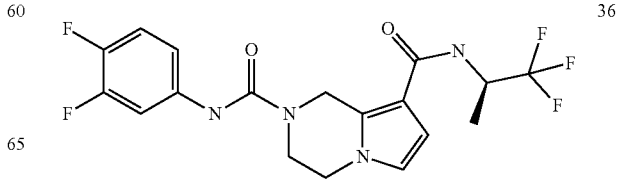

-continued

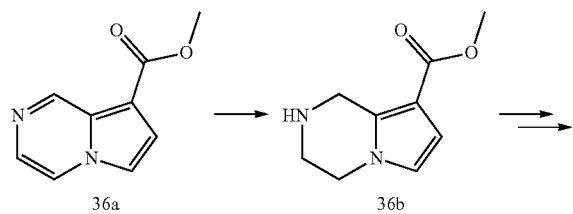

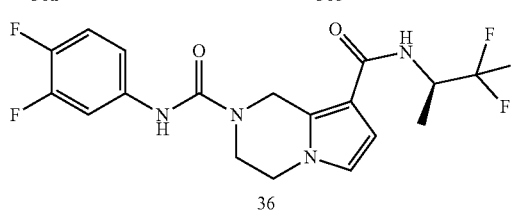

Methyl pyrrolo[1,2-α]pyrazine-8-carboxylate 36a (500 mg, 2.84 mmol, prepared according to the method disclosed in the patent application "US2015/51189 A1") and palladium-carbon (698.38 mg, 2.84 mmol) were dissolved in 10 mL of methanol under a hydrogen atmosphere. After stirring for 16 hours, the reaction solution was filtrated, and concentrated under reduced pressure to obtain the crude product methyl 1,2,3,4-tetrahydropyrrolo[1,2-α]pyrazine-8-carboxylate 36b (511 mg, yield: 100%).

MS m/z (ESI): 181.2 [M+1].

In accordance with the synthetic route of Example 2, the starting compound 2c in Step 3 was replaced with the crude starting compound 36b, accordingly, the title compound 36 (10 mg) was prepared.

MS m/z (ESI): 417.1 [M+1].

$^1$H NMR (400 MHz, CD$_3$OD) δ 7.51-7.46 (m, 1H), 7.19-7.15 (m, 2H), 6.71-6.70 (m, 2H), 5.00 (s, 2H), 4.85-4.82 (m, 1H), 4.11-4.09 (m, 2H), 3.94-3.91 (m, 2H), 1.39 (d, 3H).

Example 37

(R)—N$^7$-(2-(Difluoromethyl)pyridin-4-yl)-N$^1$-(1,1,1-trifluoropropan-2-yl)-5,6-dihydroimidazo[1,5-α]pyrazine-1,7(8H)-dicarboxamide 37

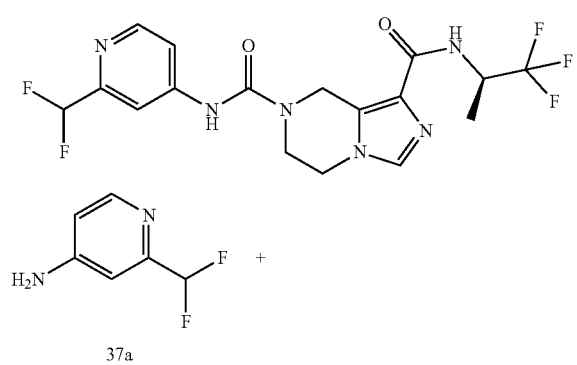

-continued

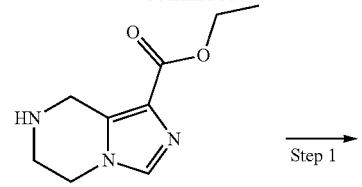

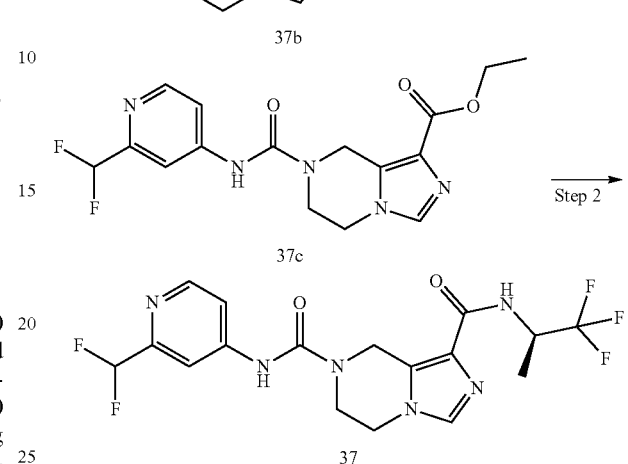

Step 1

Ethyl 7-((2-(difluoromethyl)pyridin-4-yl)carbamoyl)-5,6,7,8-tetrahydroimidazo[1,5-α]pyrazine-1-carboxylate 37c 2-(Difluoromethyl)pyridin-4-amine 37a (73.83 mg, 512.25 μmol, prepared according to the method disclosed in the patent application "WO2015/118057A1"), ethyl 5,6,7,8-tetrahydroimidazo[1,5-α]pyrazine-1-carboxylate 37b (100 mg, 512.25 μmol, Shanghai Bide Pharmatech Ltd.) and triethylamine (103.67 mg, 1.02 mmol) were dissolved in 10 mL of tetrahydrofuran, followed by addition of bis(trichloromethyl)carbonate (60.80 mg, 204.09 μmol) at 0° C. The reaction solution was warmed up slowly to room temperature, and stirred for 3 hours. The reaction solution was concentrated under reduced pressure, and the resulting residue was purified by thin layer chromatography with developing solvent system A to obtain the title compound 37c (120 mg, yield: 64.2%).

MS m/z (ESI): 366.2 [M+1].

Step 2

(R)—N$^7$-(2-(Difluoromethyl)pyridin-4-yl)-N$^1$-(1,1,1-trifluoropropan-2-yl)-5,6-dihydroimidazo[1,5-α]pyrazine-1,7(8H)-dicarboxamide 37

Compound 37c (100 mg, 273.72 μmol) and compound 1e (30.95 mg, 273.72 μmol) were dissolved in 10 mL of tetrahydrofuran, followed by addition of 1 mL of a 1M solution of lithium bis(trimethylsilyl)amide in tetrahydrofuran at 0° C. After completion of the addition, the solution was warmed up slowly to room temperature, and stirred for 6 hours. The reaction solution was concentrated under reduced pressure, and the resulting residue was purified by preparative high performance liquid chromatography (Waters 2767-SQ Detecor2, elution system: ammonium bicarbonate, water, acetonitrile) to obtain the title compound 37 (20 mg, yield: 16.9%).

MS m/z (ESI): 433.2 [M+1].

¹H NMR (400 MHz, CD₃OD) δ 8.42 (d, 1H), 7.88-7.87 (m, 1H), 7.70-7.66 (m, 2H), 6.80-6.53 (m, 1H), 5.10 (s, 2H), 4.83-4.81 (m, 1H), 4.26-4.24 (m, 2H), 4.00-3.98 (m, 2H), 1.44 (d, 3H).

Example 38

(S)—N³,N⁵-Bis(3,4-difluorophenyl)-6-methyl-6,7-dihydropyrazolo[1,5-α]pyrazine-3,5(4H)-dicarboxamide 38

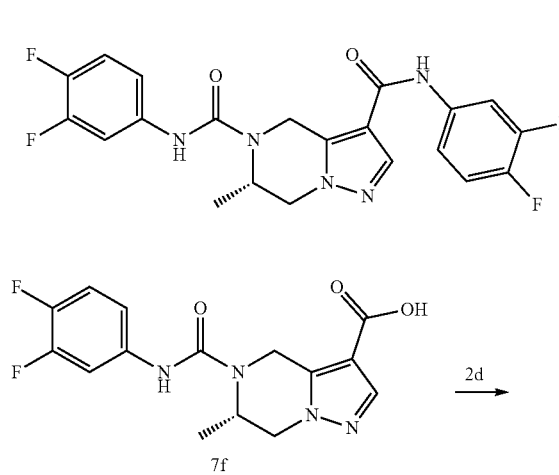

The crude compound 7f (80 mg, 237.89 μmol), O-(7-azabenzotriazol-1-yl)-N,N,N',N'-tetramethyluronium hexafluorophosphate (83.95 mg, 356.83 μmol) and N,N-diisopropylethylamine (92.23 mg, 713.66 μmol) were dissolved in 3 mL of N,N-dimethylformamide, and reacted for 10 minutes. The reaction solution was added with compound 2d (46.07 mg, 356.83 μmol), and stirred for 16 hours. The reaction solution was added with 10 mL of water, and extracted with ethyl acetate (40 mL×2). The organic phases were combined and concentrated under reduced pressure, and the resulting residue was purified by thin layer chromatography with developing solvent system C. The resulting crude product was purified by preparative high performance liquid chromatography (Waters-2767, elution system: ammonium bicarbonate, water, acetonitrile) to obtain the title compound 38 (10 mg, yield: 9.4%).

MS m/z (ESI): 448.1[M+1].

¹H NMR (400 MHz, CD₃OD) δ 8.18 (s, 1H), 7.83-7.81 (m, 1H), 7.52-7.50 (m, 1H), 7.41-7.39 (m, 1H), 7.24-7.17 (m, 3H), 5.39 (d, 1H), 5.04-5.01 (m, 1H), 4.75 (d, 1H), 4.38-4.36 (m, 1H), 4.22 (d, 1H), 1.26 (d, 3H).

Example 39

(S)—N⁵-(3,4-Difluorophenyl)-6-methyl-N³-((R)-1,1,1-trifluoropropan-2-yl)-6,7-dihydro-[1,2,3]triazolo[1,5-α]pyrazine-3,5(4H)-dicarboxamide 39

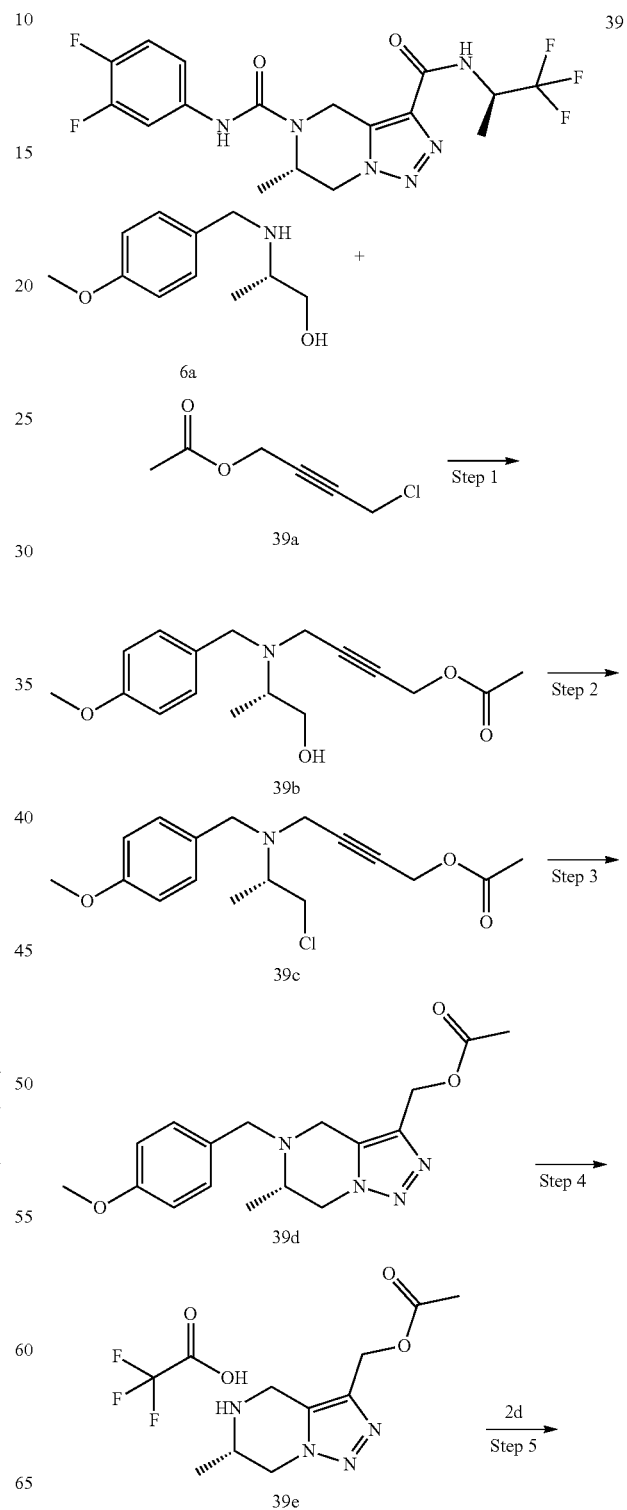

-continued

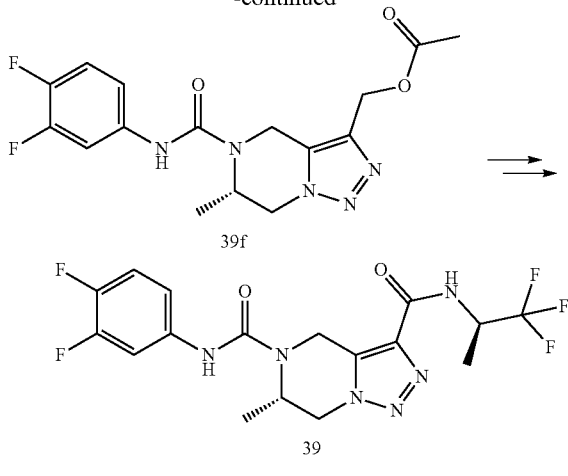

Step 1

(S)-4-((1-Hydroxypropan-2-yl)(4-methoxybenzyl)amino)but-2-yn-1-yl acetate 39b

Compound 6a (3.00 g, 15.00 mmol) was dissolved in 60 mL of dioxane, followed by addition of 4-chlorobut-2-yn-1-yl acetate 39a (5.73 g, 39.00 mmol, prepared according to the known method disclosed in "*Journal of Medicine Chemistry*, 2014, 57(9), 3687-3706") and triethylamine (4.7 g, 46.00 mmol). After stirring at 60° C. for 12 hours, the reaction solution was filtrated. The filtrate was concentrated under reduced pressure, and the resulting residue was purified by silica gel column chromatography with eluent system A to obtain the title compound 39b (2.20 g, yield: 42.2%).

MS m/z (ESI): 306.2 [M+1].

Step 2

(S)-4-((1-Chloropropan-2-yl)(4-methoxybenzyl)amino)but-2-yn-1-yl acetate 39c

Compound 39b (2.20 g, 7.20 mmol) and pyridine (854 mg, 10.08 mmol) were dissolved in 30 mL of dichloromethane, followed by slowly dropwise addition of thionyl chloride (1.50 g, 12.60 mmol) in an ice bath. The reaction solution was warmed up slowly to room temperature and stirred for 2 hours. The reaction solution was added with 100 mL of dichloromethane, washed with water (50 mL×2), dried over anhydrous sodium sulfate and filtrated. The filtrate was concentrated under reduced pressure to obtain the title compound 39c (2.20 g), which was used directly in the next step without purification.

Step 3

(S)-(5-(4-Methoxybenzyl)-6-methyl-4,5,6,7-tetrahydro-[1,2,3]triazolo[1,5-α]pyrazin-3-yl)methyl acetate 39d The crude compound 39c (2.20 g, 6.79 mmol) was dissolved in 20 mL of N,N-dimethylformamide, followed by addition of sodium azide (574 mg, 8.83 mmol). After stirring at 80° C. for 12 hours, the reaction solution was cooled to room temperature, added with 50 mL of ethyl acetate, washed with water (20 mL×2), dried over anhydrous sodium sulfate and filtrated. The filtrate was concentrated under reduced pressure, and the resulting residue was purified by silica gel column chromatography with eluent system A to obtain the title compound 39d (1.30 g, yield: 57.9%).

MS m/z (ESI): 331.1 [M+1].

Step 4

(S)-(6-Methyl-4,5,6,7-tetrahydro-[1,2,3]triazolo[1,5-α]pyrazin-3-yl)methyl acetate trifluoroacetate 39e Compound 39d (1.30 g, 2.33 mmol) was dissolved in 5 mL of trifluoroacetic acid. The reaction solution was heated to 100° C. in a microwave for 5 minutes, cooled to room temperature, and concentrated under reduced pressure to obtain the crude title compound 39e (1.28 g), which was used directly in the next step without purification.

Step 5

(S)-(5-((3,4-Difluorophenyl)carbamoyl)-6-methyl-4,5,6,7-tetrahydro-[1,2,3]triazolo[1,5-α]pyrazin-3-yl)methyl acetate 39f The crude compound 39e (200 mg, 0.62 mmol), compound 2d (228 mg, 1.90 mmol) and triethylamine (290 mg, 2.86 mmol) were dissolved in 10 mL of tetrahydrofuran, followed by addition of bis(trichloromethyl)carbonate (87 mg, 0.3 mmol) in an ice bath. After stirring for 3 hours, the reaction solution was concentrated under reduced pressure, and the residue was purified by silica gel column chromatography with eluent system C to obtain the title compound 39f (90 mg, yield: 40.1%).

MS m/z (ESI): 366.1 [M+1].

In accordance with the synthetic route of Example 17, the starting compound 17b in Step 2 was replaced with compound 39f, accordingly, the title compound 39 (20 mg) was prepared.

MS m/z (ESI): 433.1 [M+1].

$^1$H NMR (400 MHz, CD$_3$OD) δ 7.50-7.48 (m, 1H), 7.18-7.16 (m, 2H), 5.43 (d, 1H), 5.08-5.06 (m, 1H), 4.89-4.87 (m, 1H), 4.74 (d, 1H), 4.60 (d, 1H), 4.49-4.46 (m, 1H), 1.49 (d, 3H), 1.21 (d, 3H).

Example 40

(S)—N$^5$-(4-Fluoro-3-methylphenyl)-6-methyl-N$^3$-((R)-1,1,1-trifluoropropan-2-yl)-6,7-dihydro-[1,2,3]triazolo[1,5-α]pyrazine-3,5(4H)-dicarboxamide 40

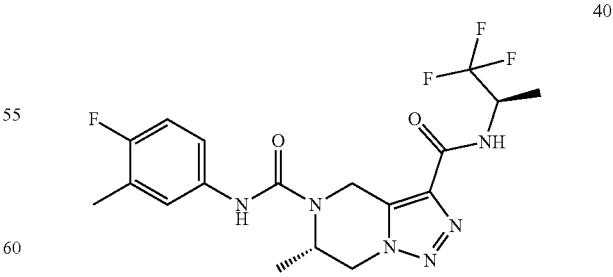

In accordance with the synthetic route of Example 39, the starting compound 2d in Step 5 was replaced with 3-methyl-4-fluoroaniline 40a, accordingly, the title compound 40 (25 mg) was prepared.

MS m/z (ESI): 429.1 [M+1].

¹H NMR (400 MHz, CD₃OD) δ 7.29-7.26 (m, 1H), 7.21-7.20 (m, 1H), 6.99-6.94 (m, 1H), 5.45-5.41 (d, 1H), 5.09-5.08 (m, 2H), 4.76-4.71 (d, 1H), 4.63-4.59 (m, 1H), 4.52-4.51 (d, 1H), 2.27-2.26 (d, 3H), 1.48-1.46 (d, 3H), 1.23-1.22 (d, 3H).

Example 41

(S)—N⁷-(3,4-Difluorophenyl)-6-methyl-N¹—((S)-1,1,1-trifluoropropan-2-yl)-5,6-dihydroimidazo[1,5-α]pyrazine-1,7(8H)-dicarboxamide 41

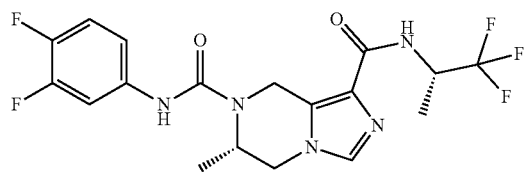

41

In accordance with the synthetic route of Example 6, the starting compound 1e was replaced with the starting compound (2S)-1,1,1-trifluoropropyl-2-amine hydrochloride (Shanghai Bide Pharmatech Ltd.), accordingly, the title compound 41 (110 mg) was prepared.

MS m/z (ESI): 432.1 [M+1].

¹H NMR (400 MHz, CDCl₃) δ 7.54-7.51 (m, 1H), 7.50 (s, 1H), 7.21-7.02 (m, 3H), 6.83 (s, 1H), 5.26-5.16 (m, 1H), 5.15-5.04 (m, 1H), 4.95-4.92 (m, 1H), 4.86-4.80 (m, 1H), 4.28-4.22 (m, 1H), 4.01-4.05 (m, 1H), 1.48 (d, 3H), 1.20 (d, 3H).

Example 42

(R)—N⁵-(3,4-Difluorophenyl)-7-methyl-N³-((R)-1,1,1-trifluoropropan-2-yl)-6,7-dihydro-[1,2,3]triazolo[1,5-α]pyrazine-3,5(4)-dicarboxamide 42

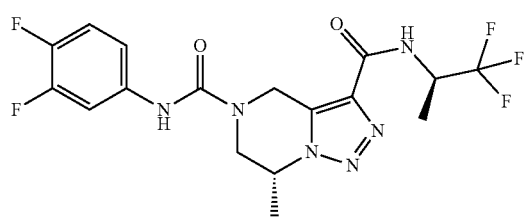

42

In accordance with the synthetic route of Example 39, the starting compound 6a in Step 1 was replaced with the compound (2R)-1-((4-methoxybenzyl)amino)propan-1-ol (prepared according to the known method disclosed in "*Organic and Biomolecular Chemistry*, 2014, 12, 16, 2584-2591"), accordingly, the title compound 42 (20 mg) was prepared.

MS m/z (ESI): 433.1 [M+1].

¹H NMR (400 MHz, CD₃OD) δ 7.50-7.48 (m, 1H), 7.15-7.12 (m, 2H), 5.16 (d, 1H), 5.02 (d, 1H), 4.77-4.75 (m, 1H), 4.13-4.10 (m, 1H), 3.77 (m, 1H), 3.06-3.03 (m, 1H), 1.67 (d, 3H), 1.44 (d, 3H).

Example 43

(S)—N⁵-(3,4-Difluorophenyl)-6-methyl-N³—((S)-1,1,1-trifluoropropan-2-yl)-6,7-dihydro-[1,2,3]triazolo[1,5-α]pyrazine-3,5(4-)-dicarboxamide 43

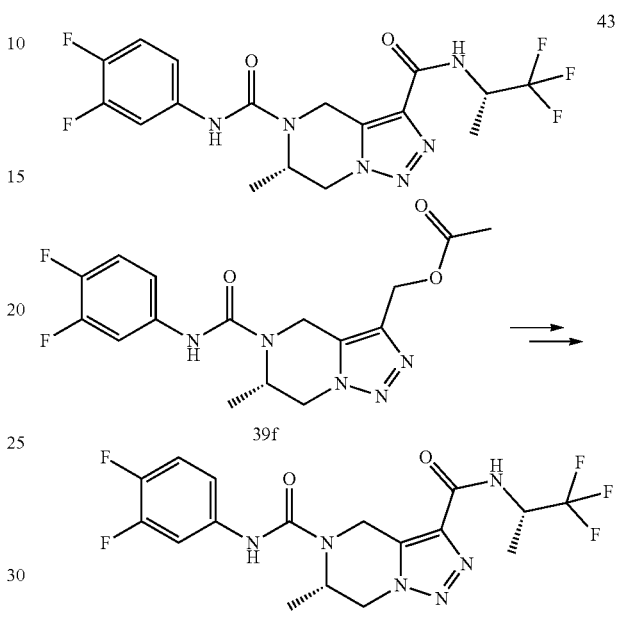

In accordance with the synthetic route of Example 17, the starting compound 17b in Step 2 was replaced with compound 39f, and the starting compound 1e was replaced with the starting compound (2S)-1,1,1-trifluoropropyl-2-amine hydrochloride, accordingly, the title compound 43 (30 mg) was prepared.

MS m/z (ESI): 433.3 [M+1].

¹H NMR (400 MHz, CDCl₃) δ 7.53-7.50 (m, 1H), 7.30 (d, 1H), 7.15 (dd, 1H), 7.06-7.04 (m, 1H), 6.84 (s, 1H), 5.37-5.32 (m, 1H), 5.27 (d, 1H), 4.89-4.85 (m, 2H), 4.61 (d, 1H), 4.52-4.48 (m, 1H), 1.50 (d, 3H), 1.26 (d, 3H).

Example 44

(R)—N⁵-(3-Cyano-4-fluorophenyl)-7-methyl-N³-((R)-1,1,1-trifluoropropan-2-yl)-6,7-dihydro-[1,2,3]triazolo[1,5-α]pyrazine-3,5(4H)-dicarboxamide 44

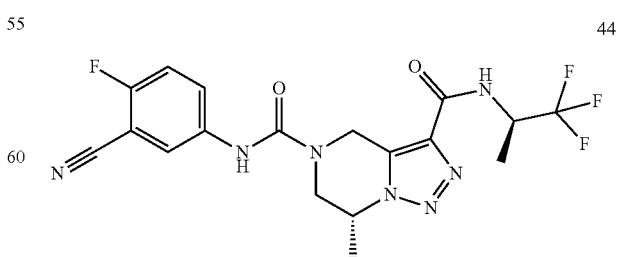

44

In accordance with the synthetic route of Example 39, the starting compound 6a in Step 1 was replaced with the compound (2R)-1-((4-methoxybenzyl)amino)propan-1-ol, and the starting compound 2d in Step 5 was replaced with compound 3d, accordingly, the title compound 44 (15 mg) was prepared.

MS m/z (ESI): 440.3 [M+1].

$^1$H NMR (400 MHz, CD$_3$OD) δ 7.86-7.84 (m, 1H), 7.73-7.70 (m, 1H), 7.29 (t, 1H), 5.19 (d, 1H), 5.05 (d, 1H), 4.85-4.82 (m, 1H), 4.12 (d, 1H), 3.77-3.73 (m, 1H), 3.64-3.62 (m, 1H), 1.69 (d, 3H), 1.46 (d, 3H).

Example 45

(S)—N$^5$-(3-Cyano-4-fluorophenyl)-6-methyl-N$^3$-((R)-1,1,1-trifluoropropan-2-yl)-6,7-dihydro-[1,2,3]triazolo[1,5-α]pyrazine-3,5(4H)-dicarboxamide 45

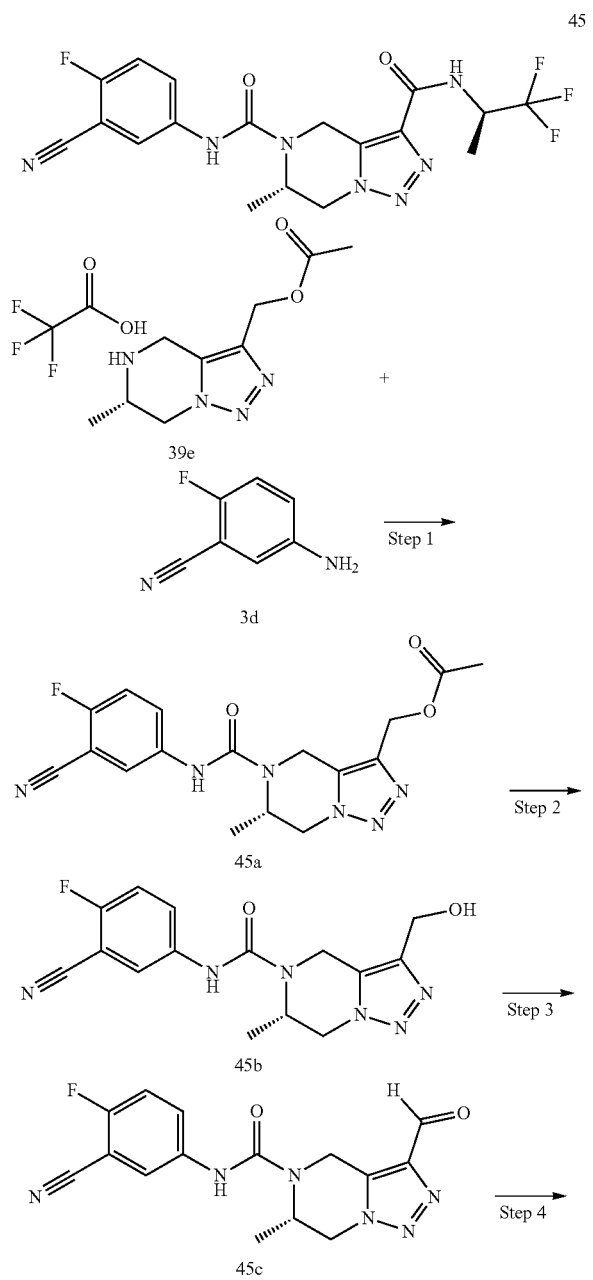

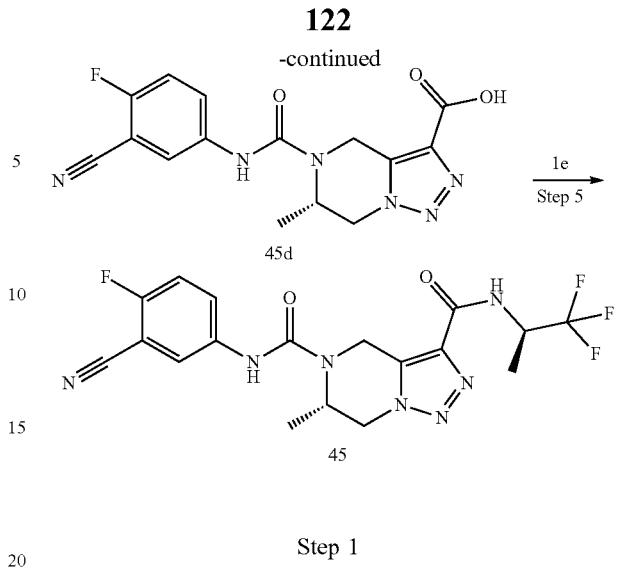

Step 1

(S)-(5-((3-Cyano-4-fluorophenyl)carbamoyl)-6-methyl-4,5,6,7-tetrahydro-[1,2,3]triazolo[1,5-α]pyrazin-3-yl)methyl acetate 45a The crude compound 39e (400 mg, 1.24 mmol), compound 3d (450 mg, 3.80 mmol) and triethylamine (580 mg, 5.80 mmol) were dissolved in 20 mL of tetrahydrofuran, followed by addition of bis(trichloromethyl)carbonate (180 mg, 0.6 mmol) in an ice bath. After stirring for 3 hours, the reaction solution was concentrated under reduced pressure, and the residue was purified by silica gel column chromatography with eluent system C to obtain the title compound 45a (195 mg, yield: 40.1%).

MS m/z (ESI): 373.1 [M+1].

Step 2

(S)—N-(3-Cyano-4-fluorophenyl)-3-(hydroxymethyl)-6-methyl-6,7-dihydro-[1,2,3]triazolo[1,5-α]pyrazine-5(4H)-carboxamide 45b Compound 45a (190 mg, 0.51 mmol) was dissolved in 5 mL of a mixed solvent of methanol and water (V:V=4:1), followed by addition of lithium hydroxide (108 mg, 2.57 mmol). After stirring for 2 hours, the reaction solution was added with 20 mL of water, and extracted with ethyl acetate (15 mL×3). The organic phases were combined, and concentrated under reduced pressure to obtain the crude title compound 45b (120 mg), which was used directly in the next step without purification.

MS m/z (ESI): 331.2 [M+1].

Step 3

(S)—N-(3-Cyano-4-fluorophenyl)-3-formyl-6-methyl-6,7-dihydro-[1,2,3]triazolo[1,5-α]pyrazine-5(4H)-carboxamide 45c The crude compound 45b (100 mg, 0.3 mmol) was dissolved in 5 mL of dichloromethane, followed by addition of pyridinium chlorochromate (138 mg, 0.64 mmol) and silica gel (140 mg, 100-200 mesh). After stirring for 3 hours, the reaction solution was filtrated and concentrated under reduced pressure, and the resulting residue was purified by thin layer chromatography with developing solvent system A to obtain the title compound 45c (60 mg, yield: 43.1%).

MS m/z (ESI): 329.5 [M+1].

Step 4

(S)-5-((3-Cyano-4-fluorophenyl)carbamoyl)-6-methyl-4,5,6,7-tetrahydro-[1,2,3]triazolo[1,5-α]pyrazine-3-carboxylic acid 45d Compound 45c (30 mg, 0.1 mmol) was dissolved in 5 mL of a mixed solvent of acetonitrile and water (V:V=3:2), followed by addition of sulfamic acid (20 mg, 0.2 mmol). After stirring for 10 minutes, the solution was added with sodium chlorite (20 mg, 0.2 mmol), and stirred for 2 hours. The reaction solution was added with 0.5 mL of saturated sodium sulfite solution and 10 mL of water successively, and extracted with ethyl acetate (10 mL×3). The organic phases were combined, and concentrated under reduced pressure to obtain the crude compound 45d (25 mg), which was used directly in the next step without purification.

MS m/z (ESI): 345.2 [M+1].

Step 5

(S)—$N^5$-(3-Cyano-4-fluorophenyl)-6-methyl-$N^3$-((R)-1,1,1-trifluoropropan-2-yl)-6,7-dihydro-[1,2,3]triazolo[1,5-α]pyrazine-3,5(4H)-dicarboxamide 45

The crude compound 45d (20 mg, 58.0 μmol), O-(7-azabenzotriazol-1-yl)-N,N,N',N'-tetramethyluronium hexafluorophosphate (105 mg, 146.5 μmol) and N,N-diisopropylethylamine (150 mg, 366.2 μmol) were dissolved in 3 mL of N,N-dimethylformamide, and reacted for 10 minutes. The reaction solution was added with compound 1e (50 mg, 110 μmol), and stirred for 3 hours. The reaction solution was concentrated under reduced pressure, and the resulting residue was purified by thin layer chromatography with developing solvent system C to obtain the title compound 45 (8 mg, yield: 31.3%).

MS m/z (ESI): 440.3 [M+1].
$^1$H NMR (400 MHz, CD$_3$OD) δ 7.87-7.84 (m, 1H), 7.73-7.70 (m, 1H), 7.29 (t, 1H), 5.45 (t, 1H), 5.08-5.06 (m, 1H), 4.92-4.89 (m, 1H), 4.77 (d, 1H), 4.62 (d, 1H), 4.50 (d, 1H), 1.46 (d, 3H), 1.21 (d, 3H).

Example 46

(S)—$N^7$-(3-Cyano-4-fluorophenyl)-6-methyl-$N^1$-(1-methylcyclobutyl)-5,6-dihydroimidazo[1,5-α]pyrazine-1,7(8H)-dicarboxamide 46

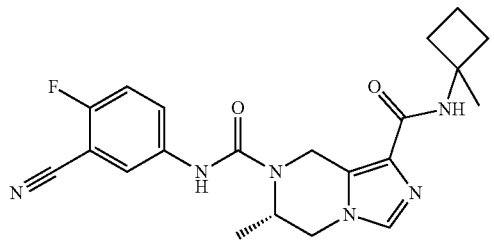

46

In accordance with the synthetic route of Example 11, the starting compound 1e in Step 3 was replaced with the compound 1-methylcyclobutyl-1-amine (Shanghai Bide Pharmatech Ltd.), accordingly, the title compound 46 (20 mg) was prepared.

MS m/z (ESI): 411.4 [M+1].
$^1$H NMR (400 MHz, CD$_3$OD) δ 7.86-7.84 (m, 1H), 7.72-7.70 (m, 1H), 7.65 (s, 1H), 7.28 (t, 1H), 5.26 (d, 1H), 4.92-4.89 (m, 1H), 4.78 (d, 1H), 4.20-4.17 (m, 2H), 2.45-2.43 (m, 2H), 2.10-2.07 (m, 2H), 1.92-1.90 (m, 2H), 1.55 (s, 3H), 1.20 (d, 3H).

Example 47

(R)—$N^7$-(3-Cyano-4-fluorophenyl)-5-methyl-$N^1$-((R)-1,1,1-trifluoropropan-2-yl)-5,6-dihydroimidazo[1,5-α]pyrazine-1,7(8H)-dicarboxamide 47

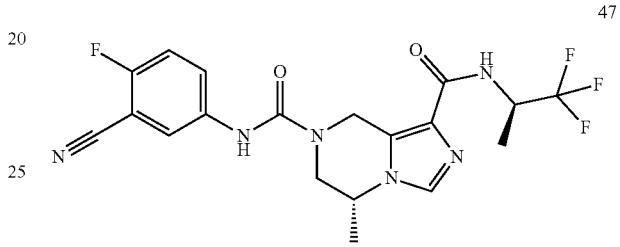

47

In accordance with the synthetic route of Example 6, the starting compound 6a in Step 1 was replaced with the starting compound (2S)-1-((4-methoxybenzyl)amino)propan-1-ol, and the starting compound 2d in Step 4 was replaced with the starting compound 3d, accordingly, the title compound 47 (12 mg) was prepared.

MS m/z (ESI): 439.2 [M+1].
$^1$H NMR (400 MHz, CDCl$_3$) δ 7.88 (dd, 1H), 7.62-7.61 (m, 1H), 7.57 (s, 1H), 7.22-7.17 (m, 3H), 5.20 (d, 1H), 5.03 (d, 1H), 4.84-4.80 (m, 1H), 4.42-4.40 (m, 1H), 4.25-4.21 (dd, 1H), 3.58-3.53 (dd, 1H), 1.64 (d, 3H), 1.47 (d, 3H).

Example 48

(S)—$N^7$-(3-Cyano-4-fluorophenyl)-6-methyl-$N^1$-(1-methylcyclopropyl)-5,6-dihydroimidazo[1,5-α]pyrazine-1,7(8H)-dicarboxamide 48

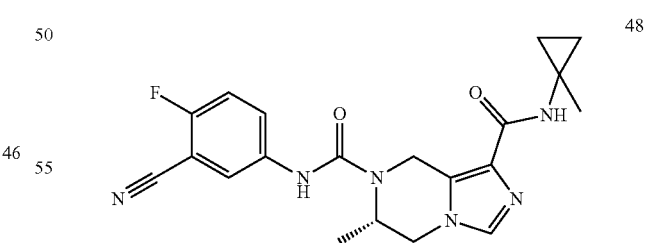

48

In accordance with the synthetic route of Example 11, the starting compound 1e in Step 3 was replaced with the compound 1-methylcyclopropyl-1-amine (Shanghai Bide Pharmatech Ltd.), accordingly, the title compound 48 (20 mg) was prepared.

MS m/z (ESI): 397.3 [M+1].
$^1$H NMR (400 MHz, CD$_3$OD) δ 7.86-7.84 (m, 1H), 7.72-7.70 (m, 1H), 7.63 (s, 1H), 7.29 (t, 1H), 5.28 (d, 1H), 4.91-4.89 (m, 1H), 4.80 (d, 1H), 4.20-4.17 (m, 2H), 1.44 (s, 3H), 1.20 (d, 3H), 0.71-0.68 (m, 2H), 0.68-0.66 (m, 2H).

Example 49

(R)—N⁵-(3,4-Difluorophenyl)-6-methyl-N³-((R)-1,1,1-trifluoropropan-2-yl)-6,7-dihydropyrazolo[1,5-α]pyrazine-3,5(4H)-dicarboxamide 49

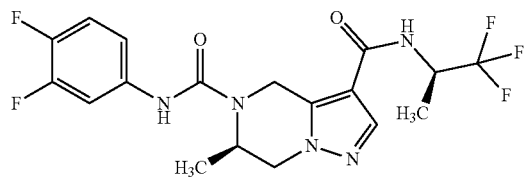

49

In accordance with the synthetic route of Example 7, the starting compound 7a in Step 1 was replaced with the starting compound tert-butyl (R)-3-iodo-6-methyl-6,7-dihydropyrazolo[1,5-α]pyrazine-5(4H)-carboxylate (prepared according to the method disclosed in the patent application "WO2017198744A1"), accordingly, the title compound 49 (20 mg) was prepared.

MS m/z (ESI): 432.2 [M+1].

¹H NMR (400 MHz, CD₃OD) δ 8.11 (m, 1H), 7.52-7.47 (m, 1H), 7.21-7.16 (m, 2H), 5.38-5.33 (d, 2H), 5.02-4.99 (m, 1H), 4.74-4.69 (d, 1H), 4.36-4.33 (m, 1H), 4.23-4.19 (d, 1H), 1.43-1.42 (d, 3H), 1.27-1.25 (d, 3H).

Example 50

(S)—N¹-(Tert-butyl)-N⁷-(3-cyano-4-fluorophenyl)-6-methyl-5,6-dihydroimidazo[1,5-α]pyrazine-1,7(8H)-dicarboxamide 50

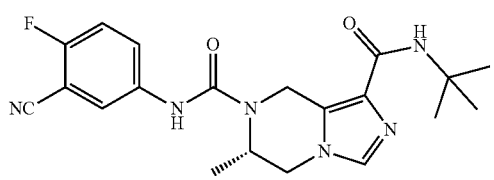

50

In accordance with the synthetic route of Example 11, the starting compound 1e in Step 3 was replaced with the starting compound tert-butylamine (Sinopharm Chemical Reagent Co., Ltd.), accordingly, the title compound 50 (180 mg) was prepared.

MS m/z (ESI): 399.2 [M+1].

¹H NMR (400 MHz, CD₃OD) δ 7.90-7.88 (m, 1H), 7.75-7.67 (m, 1H), 7.33 (s, 1H), 7.31-7.29 (m, 1H), 5.28-5.24 (d, 1H), 4.94 (m, 1H), 4.81-4.77 (m, 1H), 4.26-4.20 (m, 2H), 1.48 (d, 9H), 1.22-1.20 (d, 3H).

Example 51

(S)—N⁷-(3-Cyano-4-fluorophenyl)-N¹-((R)-1-fluoropropan-2-yl)-6-methyl-5,6-dihydroimidazo[1,5-α]pyrazine-1,7(8H)-dicarboxamide 51

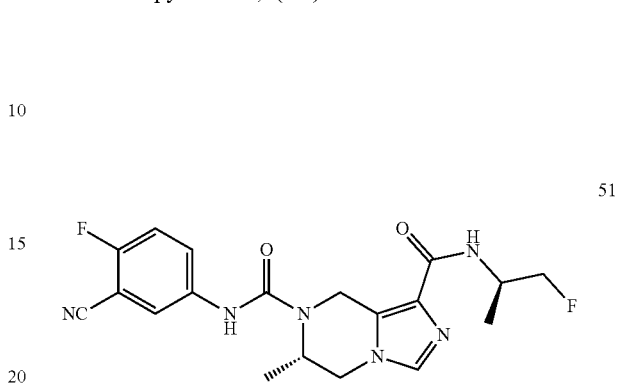

51

In accordance with the synthetic route of Example 11, the starting compound 1e in Step 3 was replaced with the starting compound (S)-2-fluoro-1-methyl-ethylamine hydrochloride (Shanghai Bide Pharmatech Ltd.), accordingly, the title compound 51 (20 mg) was prepared.

MS m/z (ESI): 403.2 [M+1].

¹H NMR (400 MHz, CD₃OD) δ 7.89-7.87 (m, 1H), 7.77-7.74 (m, 1H), 7.73 (s, 1H), 7.31-7.29 (m, 1H), 5.31-5.27 (d, 1H), 4.94-4.92 (m, 1H), 4.83-4.78 (d, 1H), 4.52-4.50 (d, 1H), 4.40-4.39 (m, 2H), 4.25-4.22 (m, 2H), 1.32-1.30 (d, 3H), 1.22-1.20 (d, 3H).

Example 52

(S)—N⁷-(3-Cyano-4-fluorophenyl)-6-methyl-N¹—((S)-1,1,1-trifluoropropan-2-yl)-5,6-dihydroimidazo[1,5-α]pyrazine-1,7(8H)-dicarboxamide 52

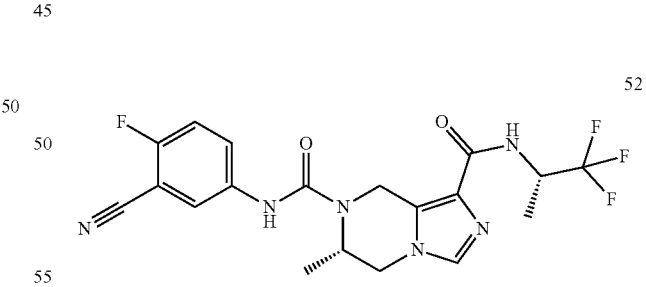

52

In accordance with the synthetic route of Example 11, the starting compound 1e in Step 3 was replaced with the starting compound (2S)-1,1,1-trifluoropropyl-2-amine hydrochloride, accordingly, the title compound 52 (20 mg) was prepared.

MS m/z (ESI): 439.2 [M+1].

¹H NMR (400 MHz, CDCl₃) δ 7.91 (dd, 1H), 7.63-7.62 (m, 1H), 7.50 (s, 1H), 7.20-7.14 (m, 3H), 5.22-5.16 (m, 2H), 4.95 (d, 1H), 4.85-4.83 (m, 1H), 4.26-4.23 (m, 1H), 4.11-4.08 (dd, 1H), 1.48 (d, 3H), 1.26 (d, 3H).

Example 53

(R)—N[7]-(3,4-Difluorophenyl)-6-methyl-N[1]-((R)-1,1,1-trifluoropropan-2-yl)-5,6-dihydroimidazo[1,5-α]pyrazine-1,7(8H)-dicarboxamide 53

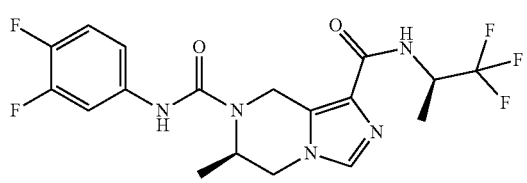

In accordance with the synthetic route of Example 6, the starting compound 6a in Step 1 was replaced with the starting compound (R)-2-((4-methoxybenzyl)amino)propan-1-ol (prepared according to the known method disclosed in "*Bioorganic & Medicinal Chemistry Letters,* 2015, 25(5), 1086-1091"), accordingly, the title compound 53 (90 mg) was prepared.

MS m/z (ESI): 432.2 [M+1].

$^1$H NMR (400 MHz, CD$_3$OD) δ 7.71 (s, 1H), 7.52-7.47 (m, 1H), 7.21-7.17 (m, 2H), 5.31-5.27 (d, 1H), 4.94-4.92 (m, 1H), 4.76-4.84 (m, 2H), 4.24-4.22 (m, 2H), 1.45-1.43 (d, 3H), 1.23-1.21 (d, 3H).

Example 54

(R)—N[7]-(3-Cyano-4-fluorophenyl)-6-methyl-N[1]-((R)-1,1,1-trifluoropropan-2-yl)-5,6-dihydroimidazo[1,5-α]pyrazine-1,7(8H)-dicarboxamide 54

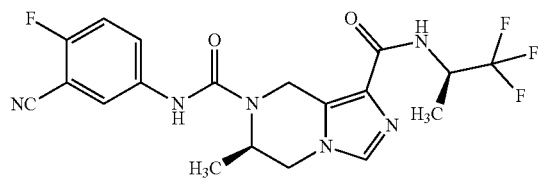

In accordance with the synthetic route of Example 6, the starting compound 6a in Step 1 was replaced with the starting compound (R)-2-((4-methoxybenzyl)amino)propan-1-ol, and the starting compound 2d in Step 4 was replaced with compound 3d, accordingly, the title compound 54 (88 mg) was prepared.

MS m/z (ESI): 439.2 [M+1].

1H NMR (400 MHz, CD$_3$OD) δ 7.89-7.87 (m, 1H), 7.75-7.73 (m, 1H), 7.71 (s, 1H), 7.33-7.29 (m, 1H), 5.32-5.28 (d, 1H), 4.95-4.93 (m, 1H), 4.85-4.82 (m, 2H), 4.25-4.22 (m, 2H), 1.45-1.43 (d, 3H), 1.23-1.22 (d, 3H).

Example 55

(R)—N[7]-(3-Cyano-4-fluorophenyl)-6-methyl-N[1]—((S)-1,1,1-trifluoropropan-2-yl)-5,6-dihydroimidazo[1,5-α]pyrazine-1,7(8H)-dicarboxamide 55

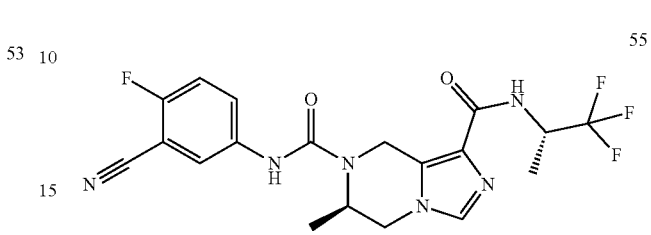

In accordance with the synthetic route of Example 6, the starting compound 6a in Step 1 was replaced with the starting compound (R)-2-((4-methoxybenzyl)amino)propan-1-ol, the starting compound 2d in Step 4 was replaced with compound 3d, and the starting compound 1e in Step 5 was replaced with the starting compound (2S)-1,1,1-trifluoropropyl-2-amine hydrochloride, accordingly, the title compound 55 (20 mg) was prepared.

MS m/z (ESI): 439.2 [M+1].

$^1$H NMR (400 MHz, CDCl$_3$) δ 7.86 (dd, 1H), 7.70-7.65 (m, 2H), 7.30-7.26 (m, 3H), 5.30 (d, 1H), 4.94-4.93 (m, 1H), 4.81-4.76 (m, 2H), 4.26-4.17 (m, 2H), 1.43 (d, 3H), 1.20 (d, 3H).

Example 56

(S)—N[7]-(3-Cyano-4-fluorophenyl)-5-methyl-N[1]-((R)-1,1,1-trifluoropropan-2-yl)-5,6-dihydroimidazo[1,5-α]pyrazine-1,7(8H)-dicarboxamide 56

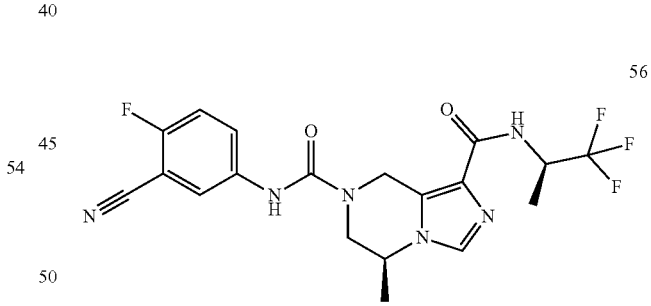

In accordance with the synthetic route of Example 6, the starting compound 6a in Step 1 was replaced with the starting compound (S)-1-((4-methoxybenzyl)amino)propan-2-ol (prepared according to the known method disclosed in "*Organic and Biomolecular Chemistry,* 2014, 12, 16, 2584-2591"), and the starting compound 2d in Step 4 was replaced with the starting compound 3d, accordingly, the title compound 56 (10 mg) was prepared.

MS m/z (ESI): 439.2 [M+1].

1H NMR (400 MHz, CD$_3$OD) δ 7.88-7.86 (m, 1H), 7.83 (s, 1H), 7.76-7.72 (m, 1H), 7.33-7.28 (m, 1H), 5.16-5.11 (d, 1H), 5.03-4.98 (m, 1H), 4.85-4.81 (m, 2H), 4.04-4.00 (m, 1H), 3.72-3.66 (m, 1H), 1.60-1.56 (d, 3H), 1.44-1.42 (d, 3H).

Example 57

N[5]-(3-Cyano-4-fluorophenyl)-7-methyl-N[3]-((R)-1,1,1-trifluoropropan-2-yl)-6,7-dihydro-[1,2,3]triazolo[1,5-α]pyrazine-3,5(4H)-dicarboxamide 57

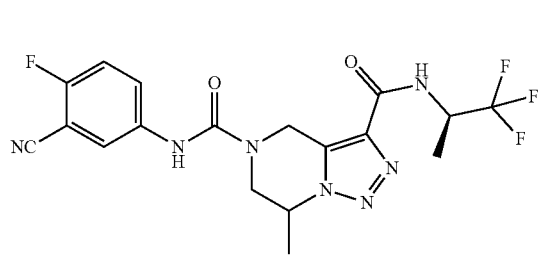

In accordance with the synthetic route of Example 39, the starting compound 6a in Step 1 was replaced with the starting compound 1-((4-methoxybenzyl)amino)propan-2-ol (prepared according to the known method disclosed in "*Organic and Biomolecular Chemistry,* 2014, 12, 16, 2584-2591"), and the starting compound 2d in Step 5 was replaced with the starting compound 3d, accordingly, the title compound 57 (220 mg) was prepared.

MS m/z (ESI): 440.2 [M+1].

$^1$H NMR (400 MHz, CD$_3$OD) δ 7.85-7.87 (m, 1H), 7.72-7.75 (m, 1H), 7.28-7.33 (m, 1H), 5.01-5.06 (d, 1H), 5.16-5.21 (d, 1H), 4.80-4.81 (m, 2H), 4.13-4.17 (m, 1H), 3.75-3.80 (m, 1H), 1.69-1.70 (d, 3H), 1.18-1.21 (d, 3H).

Example 58

(S)—N[7]-(4-Fluoro-3-methylphenyl)-6-methyl-N[1]-((R)-1,1,1-trifluoropropan-2-yl)-5,6-dihydroimidazo[1,5-α]pyrazine-1,7(8H)-dicarboxamide 58

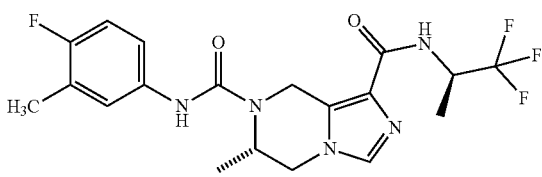

In accordance with the synthetic route of Example 6, the starting compound 2d in Step 4 was replaced with the starting compound 4-fluoro-3-methylaniline (Shanghai Bide Pharmatech Ltd.), accordingly, the title compound 58 (14 mg) was prepared.

MS m/z (ESI): 427.9 [M+1].

$^1$H NMR (400 MHz, CD$_3$OD) 7.71 (s, 1H), 7.29-7.27 (m, 1H), 7.22-7.20 (m, 1H), 6.99-6.94 (m, 1H), 5.30-5.25 (d, 1H), 4.94-4.92 (m, 1H), 4.81-4.75 (m, 2H), 4.24-4.21 (m, 2H), 2.27-2.26 (d, 3H), 1.45-1.43 (d, 3H), 1.20-1.19 (d, 3H).

Example 59

(S)—N-(3,4-Difluorophenyl)-6-methyl-1-(pyrrolidine-1-carbonyl)-5,6-dihydroimidazo[1,5-α]pyrazine-7(8H)-carboxamide 59

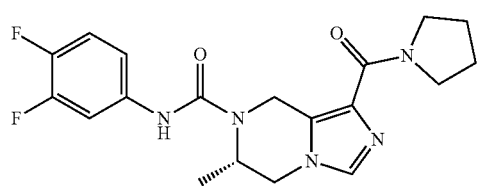

In accordance with the synthetic route of Example 11, the starting compound 3d in Step 1 was replaced with the compound 2d, the starting compound 1e in Step 3 was replaced with the starting compound pyrrolidine (Sinopharm Chemical Reagent Co., Ltd.), accordingly, the title compound 59 (10 mg) was prepared.

MS m/z (ESI): 389.8 [M+1].

$^1$H NMR (400 MHz, CDCl$_3$) δ 7.69 (s, 1H), 7.52-7.47 (m, 1H), 7.20-7.16 (m, 3H), 5.26 (d, 1H), 4.93-4.90 (m, 1H), 4.77 (d, 1H), 4.23-4.21 (m, 2H), 4.04-4.01 (m, 2H), 3.63-3.60 (m, 2H), 2.01-1.93 (m, 4H), 1.22 (d, 3H).

Biological Assay

Test Example 1

In vitro anti-HBV activity test of the compound of the present invention (quantitative assay of intracellular HBV DNA)

I. Experimental Materials and Instruments
1. QIAamp 96 DNA QIAcube HT Kit (Qiagen)
2. QIAcube HT plasticware (Qiagen)
3. Hepatitis B virus nucleic acid quantitative detection kit (Triplex International Biosciences Co., Ltd.)
4. DNA extraction device (QIAcube) (Qiagen)
5. QuantStudio 6 Fiex (ABI, ThermFisher)
6. Microplate reader (BMG)
7. HepG2.2.15 cells (Shanghai Ruilu Biotechnology Co., Ltd.)

II. Experimental Procedures

HepG2.2.15 cell is a stable expression cell line that has integrated HBV genome.

Virus particles containing HBV DNA can be synthesized by replication, transcription and encapsidation in the cells, and then secreted. In this study, the quantitative analysis of HBV DNA produced by HepG2.2.15 in vitro proliferation was carried out by quantitative PCR method, thereby determining the activity of the compound of the present invention on inhibiting the HBV DNA replication by inhibiting the assembly of HBV capsid protein.

HepG2.2.15 cells were cultured in DMEM/high glucose medium (10% FBS, 400 g/ml G418) and passaged every three days. On the day of the experiment, a cell suspension was prepared with fresh cell culture medium, and incubated in a 96-well plate (Corning, #3599) at 40,000 cells/well, at 5% carbon dioxide, 37° C. On Day 2, the compound was dissolved in pure DMSO at a concentration of 20 mM, and then the first concentration of 2 mM was formulated with DMSO, and and diluted in 4-fold concentration gradient to 8 concentrations. A control well was added with 90 μl of DMSO. The compound solution was diluted 200-fold with DMEM/high glucose medium. The cell culture plate inoculated on Day 1 was taken out. The medium in the wells was removed by a negative pressure suction device, and the formulated medium containing the compound at each concentration was added respectively to each well at 200 μl/well. The plate was incubated at 37° C. for 72 hours. On Day 5, the medium of the cultured cells was replaced with fresh medium containing the same compound in the same way as Day 2, and then the plate was incubated at 37° C. for 72 hours. On Day 8, the cell culture plate was taken out, centrifuged at 300 g for 3 minutes, and the culture supernatant was collected at 200 μl/well. HBV DNA was extracted from the cell culture supernatant with Qiagen automatic DNA extraction device, and the specific method referred to the instructions of the reagents and instruments. Finally, the extracted DNA was eluted with DNA elution buffer at 100 μl/well. The extracted DNA was subjected to quantitative PCR analysis of HBV DNA using Hepatitis B virus nucleic acid quantitative detection kit (Triplex International Biosciences Co., Ltd.), and the specific method referred to the instruction of the kit. The quantitative standard curve was obtained with the standard sample provided in the kit, and the experiments were performed in parallel. Quantitative conversion of each sample was carried out according to the standard curve. Finally, the $EC_{50}$ value of the compound was calculated with Graphpad Prism software according to each concentration of the compound and the corresponding DNA value. Emax is the effect value of the compound to maximally inhibit HBV DNA replication.

The in vitro activity of the compound of the present invention on inhibiting the HBV DNA replication by inhibiting the assembly of HBV capsid protein was determined by the above experiment. The measured $EC_{50}$ values are shown in Table 1.

TABLE 1

$EC_{50}$ values of the compound of the present invention in the anti--HBV activity test (quantitative assay of intracellular HBV DNA)

| Example No. | $EC_{50}$ (nM) | Emax (%) |
| --- | --- | --- |
| 2 | 30 | 100 |
| 4 | 27 | 100 |
| 6 | 4 | 100 |
| 7 | 38 | 100 |
| 8 | 15 | 100 |
| 9 | 28 | 100 |
| 10 | 29 | 100 |
| 11 | 18 | 100 |
| 12 | 32 | 100 |
| 13 | 35 | 100 |
| 14 | 44 | 100 |
| 15 | 29 | 100 |
| 16 | 50 | 100 |
| 17 | 70 | 80 |
| 39 | 19 | 100 |
| 40 | 20 | 100 |
| 41 | 24 | 100 |
| 42 | 75 | 100 |
| 43 | 39 | 99 |
| 44 | 60 | 99 |
| 45 | 38 | 102 |
| 46 | 65 | 97 |
| 47 | 82 | 100 |
| 48 | 93 | 98 |

TABLE 1-continued $EC_{50}$ values of the compound of the present invention in the anti--HBV activity test (quantitative assay of intracellular HBV DNA)

| Example No. | $EC_{50}$ (nM) | Emax (%) |
| --- | --- | --- |
| 58 | 15 | 100 |
| 59 (Control Example) | 5271 | 90 |

Conclusion: The compound of the present invention has a significant inhibition effect on HBV DNA replication, and has a significant advantage compared with Comparative Example 59. The main structural difference between Comparative Example 59 and the compound of the present application is that the amino group in the acylamino group is a tertiary amine, indicating that the secondary amino group in the acylamino group of the compound of the present application improves the biological activity significantly.

Test Example 2. Effect of the Compound of the Present Invention on In Vitro Proliferation of HepG2 Cells I. Experimental Materials and Instruments
1. HepG2 cells (ATCC)
2. CellTiter-Glo™ Cell Proliferation Kit (Promega)
3. Automatic Pipetting Workstation (Bravo): Agilent Technologies Co.
4. Microplate reader (VICTOR 3): PerkinElmer Co.
5. $CO_2$ incubator (Fisher Scientific)
6. Centrifuge (Fisher Scientific)

II. Experimental Procedures

HepG2 cells in logarithmic growth phase were taken and digested with trypsin to prepare a cell suspension, which was incubated in a 96-well plate (transparent bottom white 96-well plate, PerkinElmer) at 6,000 cells/well, at 5% carbon dioxide, 37° C. for 16-20 hours. On Day 2, the compound was dissolved in pure DMSO at a concentration of 20 mM. The compound was diluted in 3-fold concentration gradient using an automatic pipetting station (Bravo), 8 concentration points for each compound, and the control well was DMSO. The compound formulated in DMSO at each concentration point was diluted 200-fold with EMEM (containing 10% FBS) medium. The cell culture plate inoculated on Day 1 was taken out. The medium in the wells was removed by a negative pressure suction device, and the formulated medium containing the compound at each concentration was added respectively to each well at 100 μl/well. The plate was incubated at 37° C. for 72 hours. On Day 5, the 96-well cell culture plate was taken out, and freshly formulated CellTiter Glo was added to each well at 100 μl/well. The 96-well plate was left to stand for 5-10 minutes, the bottom was then sealed with a white bottom sealing film (PerkinElmer). The plate was placed in the microplate reader to measure the luminescence signal. The $CC_{50}$ value of the compound was calculated with Graphpad Prism software according to each concentration of the compound and the corresponding proliferation inhibition signal value.

The inhibition effect of the compound of the present invention on in vitro proliferation of HepG2 cells was determined by the above experiment. The measured $CC_{50}$ values are shown in Table 2.

TABLE 2

$CC_{50}$ values of the compound of the present invention on in vitro proliferation inhibition of HepG2 cells

| Example No. | $CC_{50}$ (μM) |
| --- | --- |
| 2 | >100 |
| 4 | >100 |
| 6 | >100 |
| 7 | >100 |

TABLE 2-continued $CC_{50}$ values of the compound of the present invention on in vitro proliferation inhibition of HepG2 cells

| Example No. | $CC_{50}$ (μM) |
|---|---|
| 8 | >100 |
| 9 | >100 |
| 10 | >100 |
| 11 | >100 |
| 12 | >100 |
| 13 | >100 |
| 14 | >100 |
| 15 | >100 |
| 16 | >100 |
| 17 | >100 |
| 39 | >100 |
| 40 | >100 |
| 41 | >100 |
| 42 | >100 |
| 43 | >100 |
| 44 | >100 |
| 45 | >100 |
| 46 | >100 |
| 47 | >100 |
| 48 | >100 |
| 58 | >100 |

Conclusion: The compound of the present invention has no or little effect on the in vitro proliferation inhibition of HepG2 cells, and shows a high safety.

Pharmacokinetics Evaluation

Test Example 3

Pharmacokinetics assay of the compound of the present invention

1. Abstract

Rats were used as test animals. The drug concentration in plasma at different time points was determined by LC/MS/MS method after intragastrical administration of the compound of Example 1, the compound of Example 2, the compound of Example 4, the compound of Example 6, the compound of Example 7, the compound of Example 11, the compound of Example 39, the compound of Example 42, the compound of Example 44, the compound of Example 45 and the compound of Example 47 to rats. The pharmacokinetic behavior and property of the compound of the present invention were studied and evaluated in rats.

2. Test Protocol 2.1 Test Compounds

Compound of Example 1, compound of Example 2, compound of Example 4, compound of Example 6, compound of Example 7, compound of Example 11, compound of Example 39, compound of Example 42, compound of Example 44, compound of Example 45 and compound of Example 47.

2.2 Test Animals

44 Healthy adult SD rats (half male and half female, 4 rats/group) were purchased from Shanghai Jiesijie Laboratory Animal Co., LTD, with Certificate No.: SCXK (Shanghai) 2013-0006.

2.3 Preparation of the Test Compound

A certain amount of the test compound was weighed, and added with 5% by volume of DMSO, 5% by volume of tween 80 and 90% by volume of normal saline to prepare a 0.2 mg/mL colorless, clear and transparent solution.

2.4 Administration

After an overnight fast, SD rats were administrated intragastrically with the test compound at an administration dose of 2.0 mg/kg and an administration volume of 10.0 mL/kg.

3. Process

The rats were intragastrically administrated the compound of Example 1, the compound of Example 2, the compound of Example 4, the compound of Example 6, the compound of Example 7, the compound of Example 11, the compound of Example 39, the compound of Example 42, the compound of Example 44, the compound of Example 45 and the compound of Example 47. 0.1 ml of blood was taken from the orbit before administration and at 0.5, 1.0, 2.0, 4.0, 6.0, 8.0, 11.0 and 24.0 hours after administration. The samples were stored in heparinized tubes, and centrifuged for 10 minutes at 3500 rpm to separate the blood plasma. The plasma samples were stored at −20° C. The rats were fed two hours after administration.

The content of the test compound in the plasma of rats after intragastrical administration of the test compound at different concentrations was determined: 25 μL of rat plasma at each time after administration was taken, added with 40 μL of the internal standard solution of camptothecin (100 ng/mL) and 200 μL of acetonitrile, vortex-mixed for 5 minutes, and centrifuged for 10 minutes (4000 rpm). 0.2 μL of the supernatant was taken from the plasma samples for LC/MS/MS analysis.

4. Results of Pharmacokinetic Parameters

Pharmacokinetic parameters of the compound of the present invention are shown below:

| | Pharmacokinetics assay (2 mg/kg) | | | | | | |
|---|---|---|---|---|---|---|---|
| No. | Plasma concentration Cmax (ng/mL) | Area under curve AUC (ng/mL*h) | Half-life T1/2 (h) | Residence time MRT (h) | Clearance CLz/F (ml/min/kg) | Apparent distribution volume Vz/F (ml/kg) | Bio-availability (%) F % |
| Example 1 | 640 ± 102 | 14438 ± 3012 | 11.7 ± 2.3 | 17.4 ± 3.0 | 2.39 ± 0.5 | 2357 ± 245 | 119 |
| Example 2 | 661 ± 200 | 9251 ± 3309 | 8.01 ± 2.26 | 11.5 ± 2.8 | 4 ± 1.48 | 2584 ± 638 | 107 |
| Example 4 | 425 ± 100 | 7129 ± 2636 | 8.8 ± 1.95 | 13.1 ± 2.5 | 5.08 ± 1.48 | 3692 ± 532 | 120 |
| Example 6 | 629 ± 167 | 12920 ± 6605 | 10.8 ± 8.1 | 16.7 ± 10.1 | 3.22 ± 1.66 | 2162 ± 721 | 120 |
| Example 7 | 1078 ± 151 | 16528 ± 9264 | 9.72 ± 5.94 | 14.1 ± 8.0 | 2.63 ± 1.46 | 1649 ± 174 | 98 |
| Example 11 | 597 ± 64 | 10870 ± 4522 | 11.2 ± 5.63 | 16.3 ± 7.6 | 3.53 ± 1.50 | 2888 ± 389 | 111 |
| Example 39 | 682 ± 168 | 8105 ± 1585 | 6.49 ± 1.71 | 9.82 ± 1.75 | 4.21 ± 0.69 | 2328 ± 590 | 114 |
| Example 42 | 433 ± 102 | 7380 ± 3177 | 15.9 ± 8.9 | 22.1 ± 12.4 | 5.3 ± 2.47 | 5962 ± 1222 | 87 |
| Example 44 | 509 ± 39.4 | 11771 ± 3103 | 17 ± 5.05 | 24.2 ± 7.38 | 2.99 ± 0.78 | 4134 ± 260 | 94 |
| Example 45 | 715 ± 187 | 17162 ± 5791 | 19.2 ± 7.16 | 27.4 ± 9.5 | 2.13 ± 0.73 | 3293 ± 1078 | 110 |
| Example 47 | 462 ± 94 | 7265 ± 3054 | 13.1 ± 4.3 | 17.7 ± 6.3 | 5.4 ± 2.69 | 5685 ± 2240 | 125 |

Conclusion: The compound of the present invention is well absorbed, and has a high bioavailability and pharmacokinetic advantage.

What is claimed is:

1. A compound of formula (I):

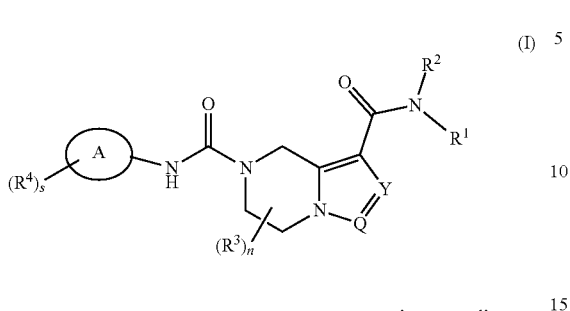

or a tautomer, mesomer, racemate, enantiomer, diastereomer thereof, or mixture thereof, or a pharmaceutically acceptable salt thereof, wherein:

ring A is phenyl or pyridyl;

Y is N or $CR^5$;

Q is N or CH;

$R^1$ is selected from the group consisting of alkyl, cycloalkyl, phenyl and heterocyclyl, wherein the alkyl is optionally further substituted by one or more substituents selected from the group consisting of halogen, alkoxy, and hydroxy, wherein the cycloalkyl is optionally further substituted by one or more alkyl, wherein the phenyl is optionally further substituted by one or more halogen, and wherein the heterocyclyl is optionally further substituted by one or more alkyl;

$R^2$ is hydrogen;

each $R^3$ is identical or different and each is independently selected from the group consisting of hydrogen and alkyl;

each $R^4$ is identical or different and each is independently selected from the group consisting of halogen, alkyl, haloalkyl and cyano;

$R^5$ is selected from the group consisting of hydrogen and alkyl;

n is 0, 1, 2 or 3;

s is 0, 1, 2, 3 or 4;

wherein the alkyl is $C_{1-6}$ alkyl;

the haloalkyl is $C_{1-6}$ haloalkyl;

the alkoxy is $C_{1-6}$ alkoxy;

the cycloalkyl is 3 to 6 membered cycloalkyl; and the heterocyclyl is 3 to 8 membered heterocyclyl with oxygen as the hetero atom.

2. The compound according to claim 1, being a compound of formula (III), formula (IV), formula (V) or formula (VI):

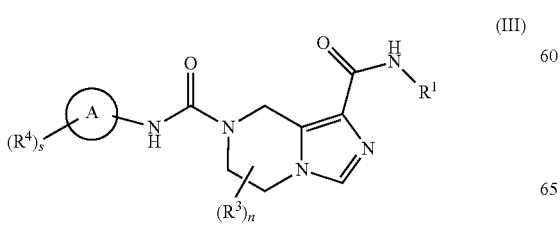

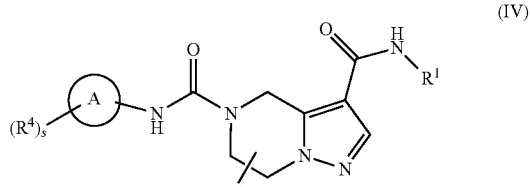

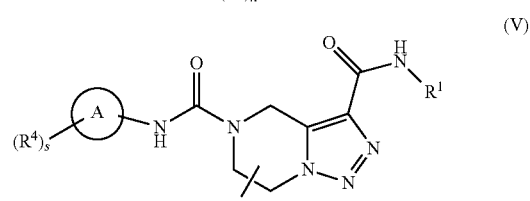

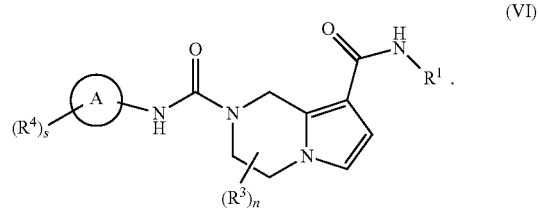

3. The compound according to claim 1, being a compound of formula (VII), formula (VIII), formula (IX) or formula (X):

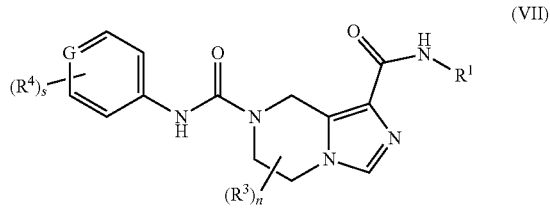

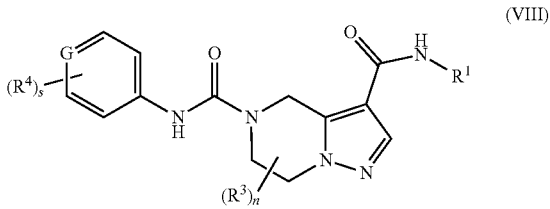

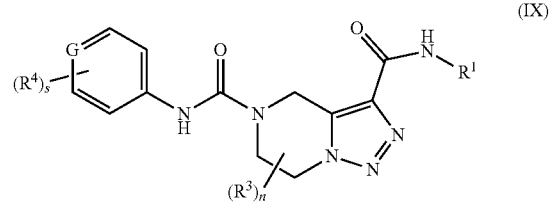

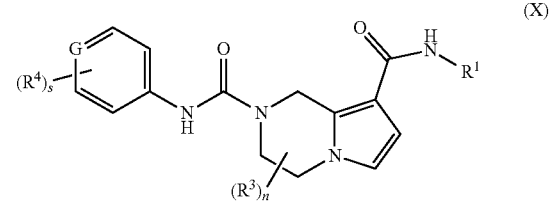

wherein G is C or N.

4. The compound according to claim 1, wherein $R^1$ is selected from the group consisting of alkyl, cycloalkyl and heterocyclyl, wherein the alkyl is optionally further substituted by one or more substituents selected from the group consisting of halogen, alkoxy and hydroxy, wherein the cycloalkyl is optionally further substituted by one or more alkyl, wherein the heterocyclyl is optionally further substituted by one or more alkyl; and wherein the alkyl is $C_{1-6}$ alkyl;

the alkoxy is $C_{1-6}$ alkoxy;

the cycloalkyl is 3 to 6 membered cycloalkyl; and the heterocyclyl is 3 to 8 membered heterocyclyl with oxygen as the hetero atom.

5. The compound according to claim 1, being a compound of formula (VII-A), formula (VIII-A), formula (IX-A) or formula (X-A):

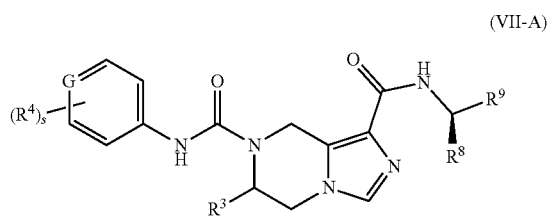

(VII-A)

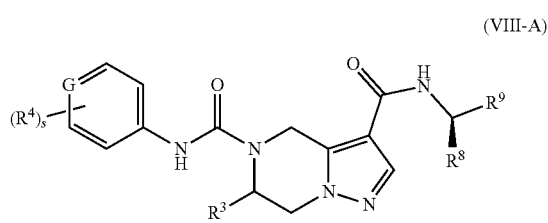

(VIII-A)

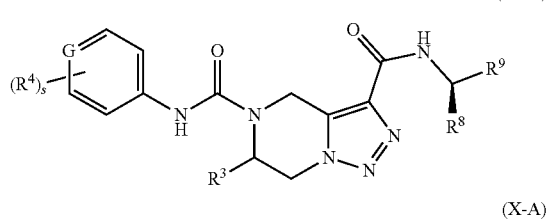

(IX-A)

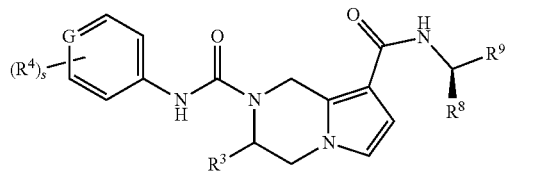

(X-A)

wherein:

G is C or N;

$R^8$ is methyl; and $R^9$ is methyl or ethyl, wherein the methyl or ethyl is optionally further substituted by one or more halogen.

6. The compound according to claim 1, selected from the group consisting of:

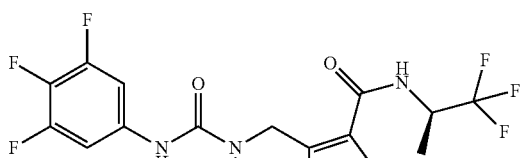

1

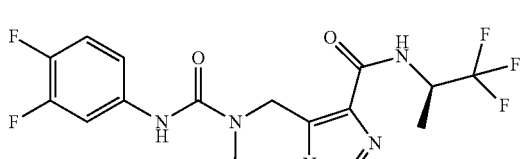

2

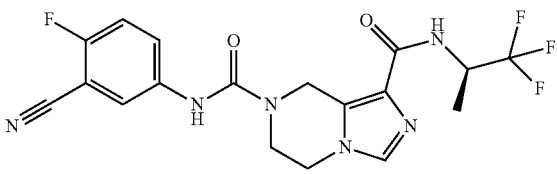

3

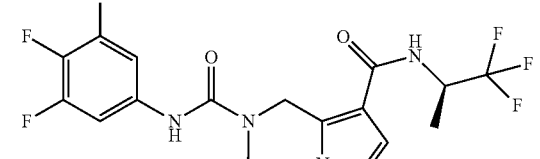

4

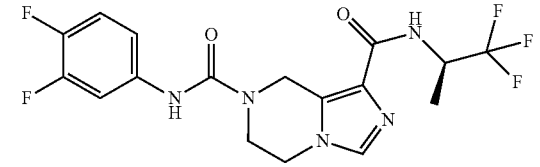

5

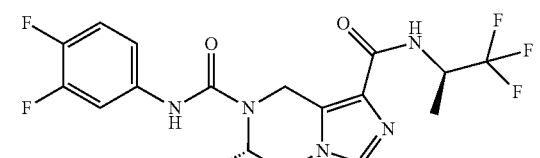

6

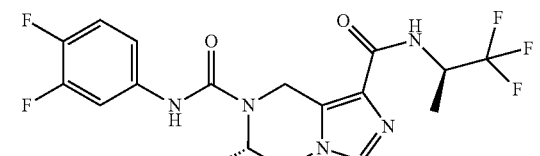

7

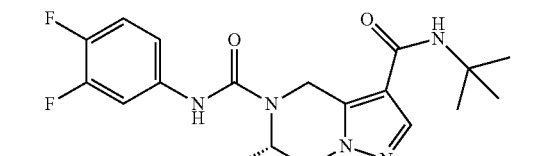

8

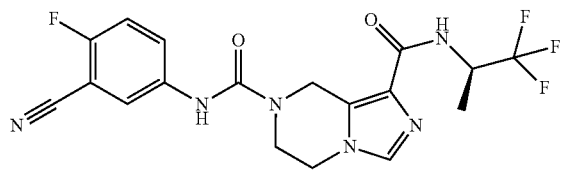
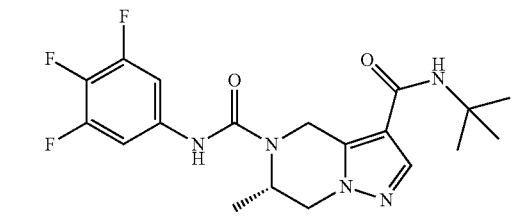
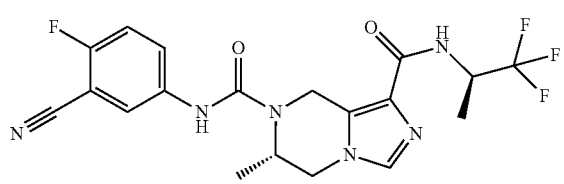
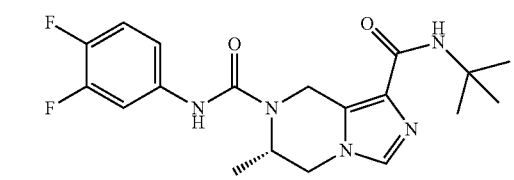
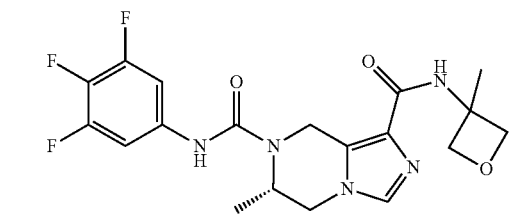
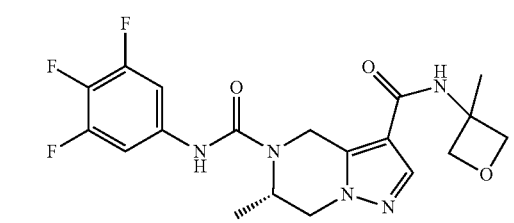
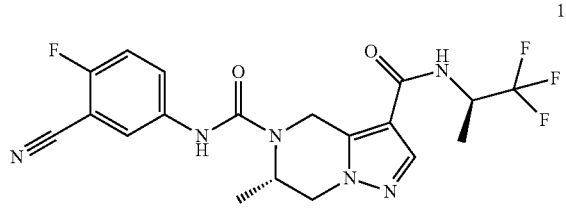
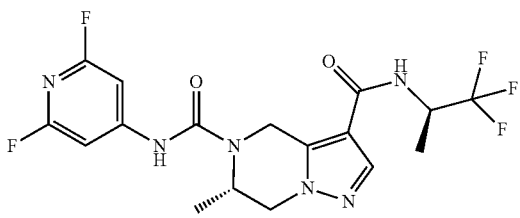
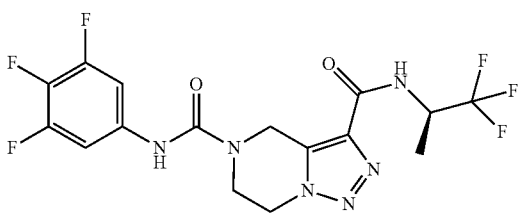
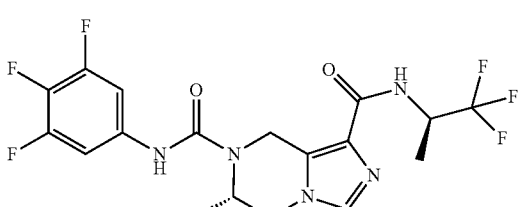
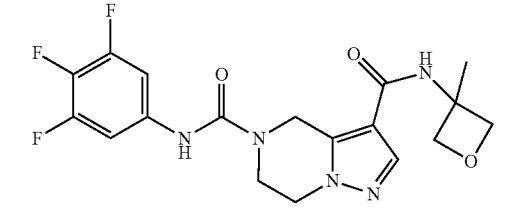
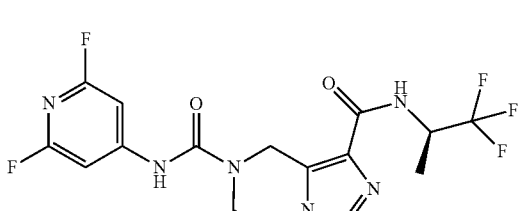
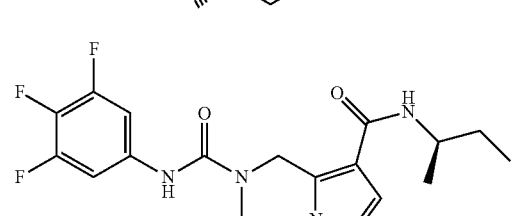
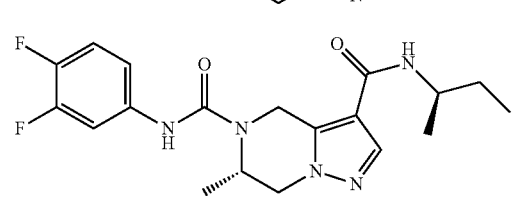

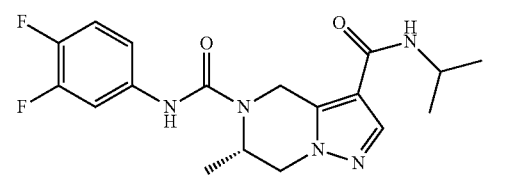
23
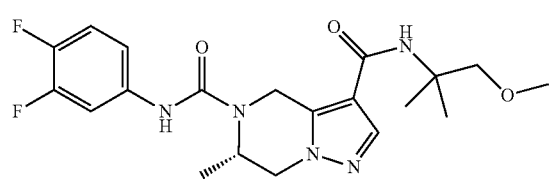
24
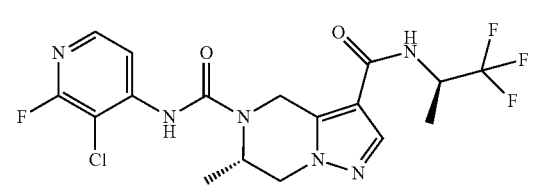
25
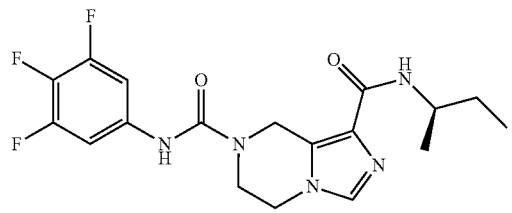
26
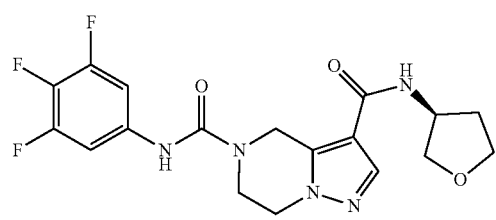
27
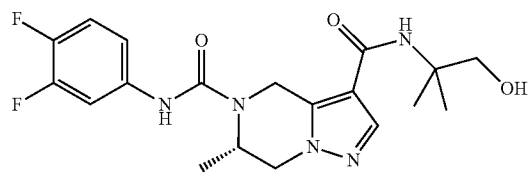
28
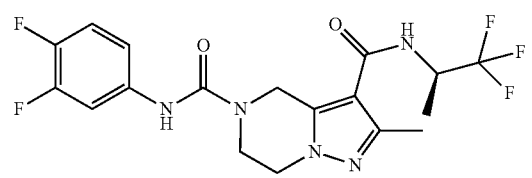
29
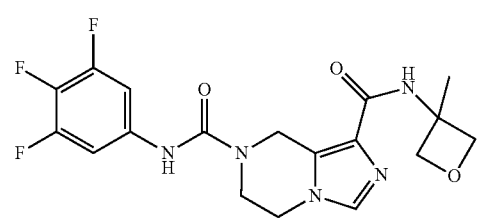
30
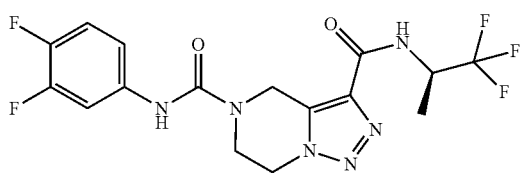
31
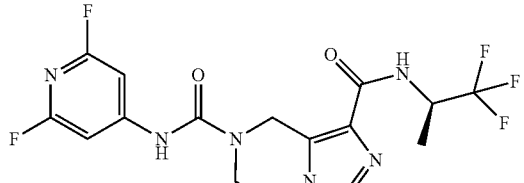
32
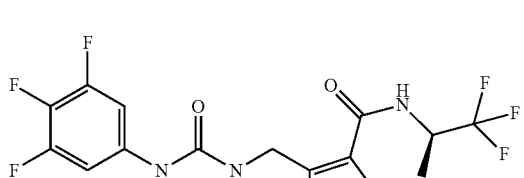
33
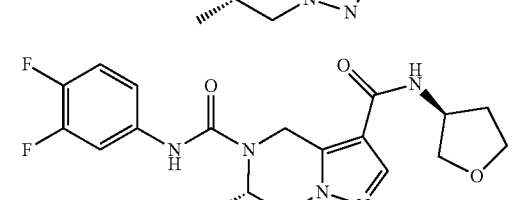
34
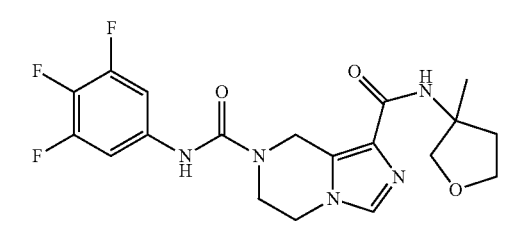
35
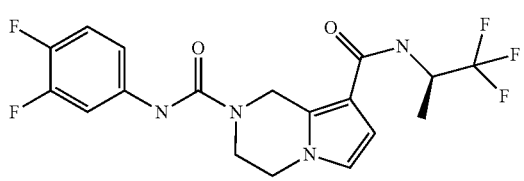
36
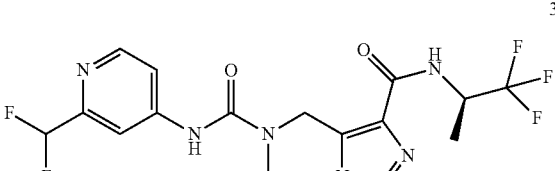
37
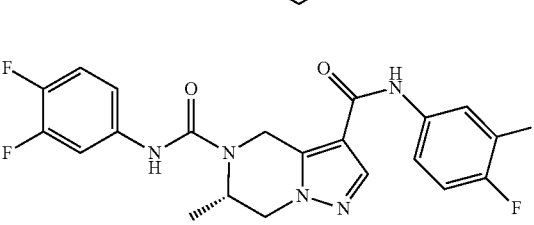
38

39
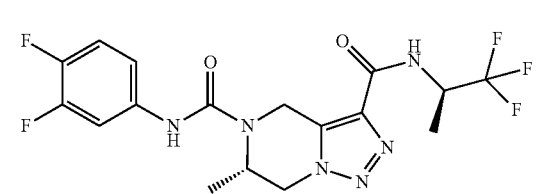
40
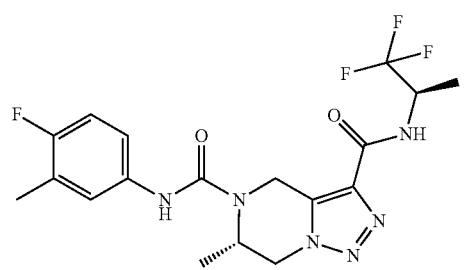
41
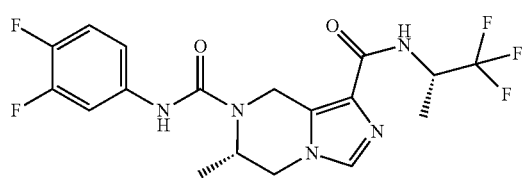
42
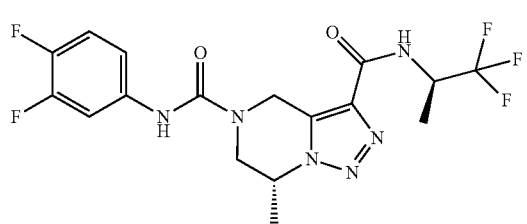
43
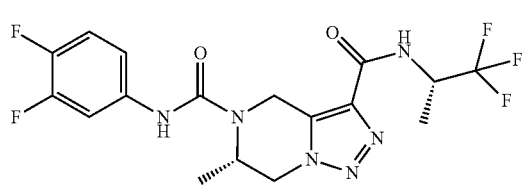
44
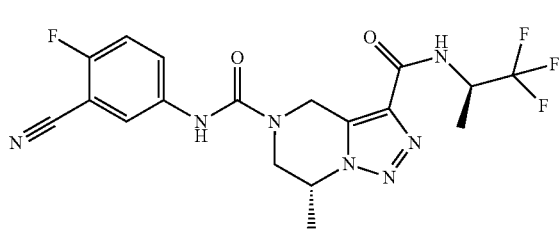
45
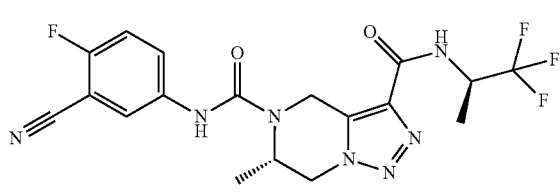
46
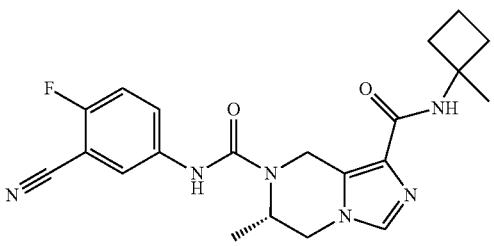
47
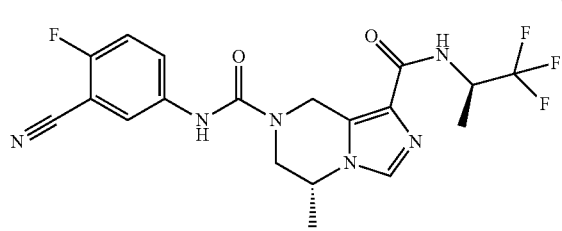
48
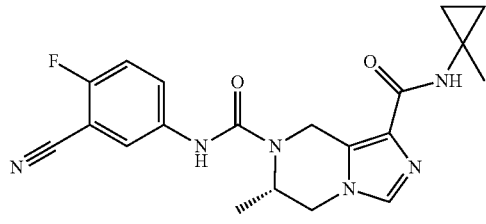
49
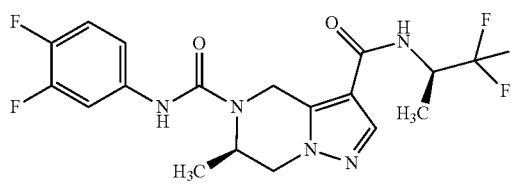
50
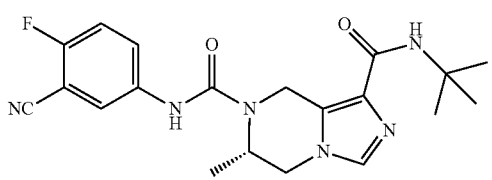
51
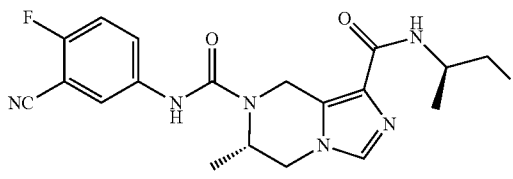
52
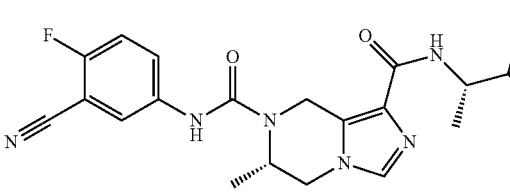
53
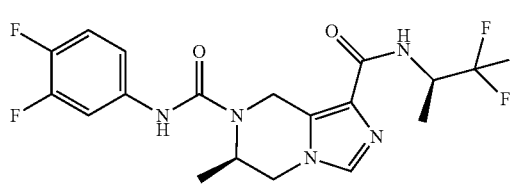

-continued

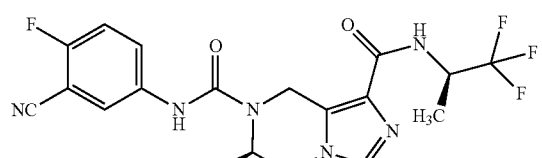
54

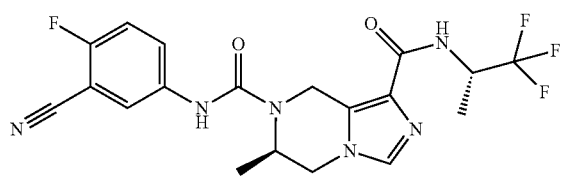
55

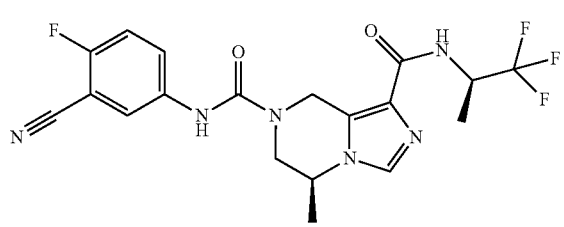
56

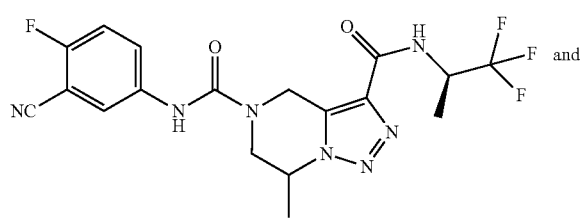
57 and

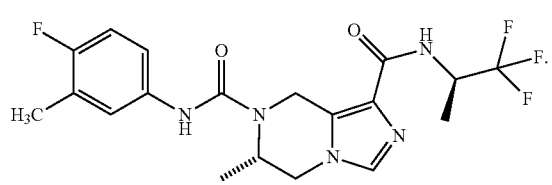
58

7. The compound according to claim 6, wherein the compound is

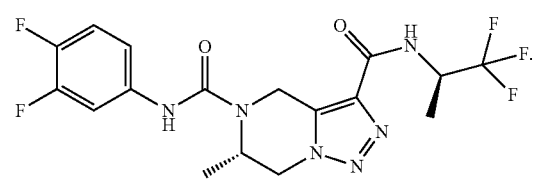
39

8. The compound according to claim 6, wherein the compound is

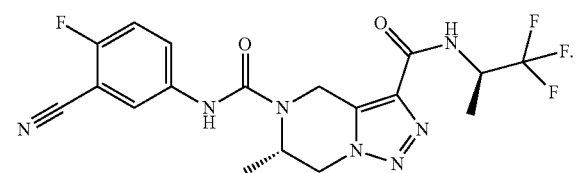
45

9. A compound of formula (IA):

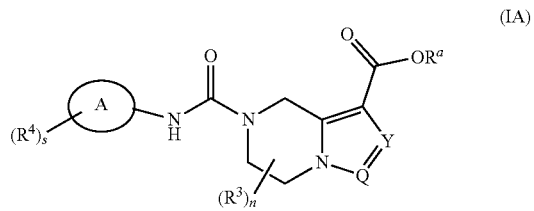
(IA)

or a tautomer, mesomer, racemate, enantiomer, diastereomer thereof, or mixture thereof, or a pharmaceutically acceptable salt thereof, wherein:
$R^a$ is hydrogen or alkyl;
ring A is phenyl or pyridyl;
Y is N or CH;
Q is N or CH, wherein Y and Q are not both CH;
each $R^3$ is identical or different and each is independently selected from the group consisting of hydrogen and alkyl;
each $R^4$ is identical or different and each is independently selected from the group consisting of halogen, alkyl, haloalkyl and cyano
n is 0, 1, 2 or 3;
s is 0, 1, 2, 3 or 4;
wherein
the alkyl is $C_{1-6}$ alkyl; and
the haloalkyl is $C_{1-6}$ haloalkyl.

10. The compound according to claim 9, wherein the compound is selected from the group consisting of:

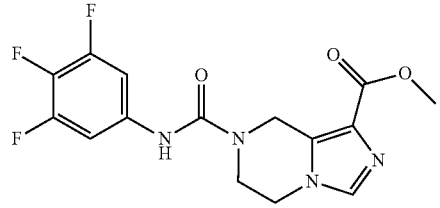
1d

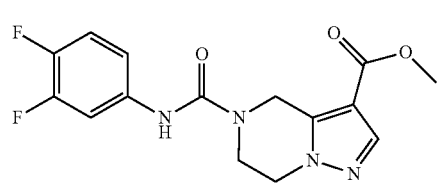
2e

147
-continued
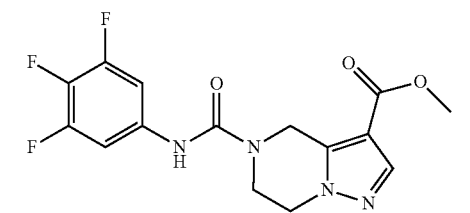
4a
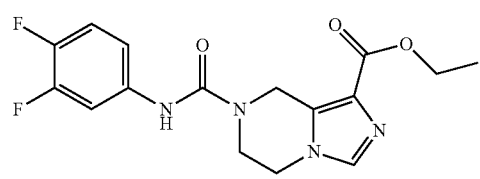
5b
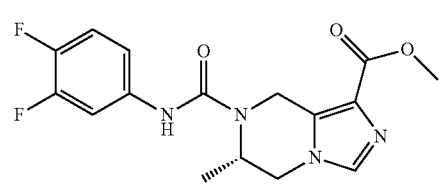
6f
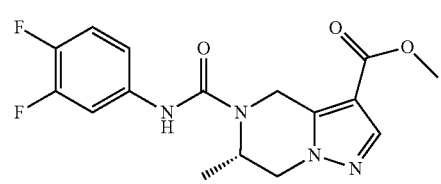
7e
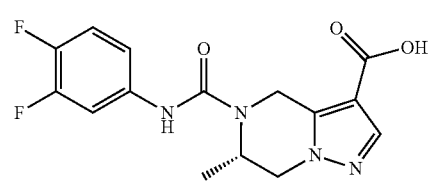
7f
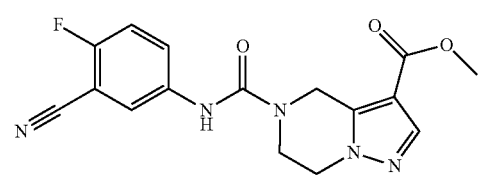
9a
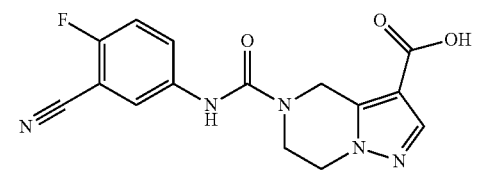
9b
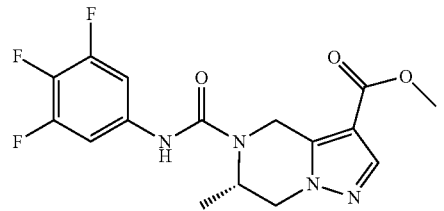
10a
148
-continued
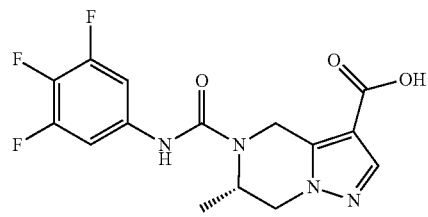
10b
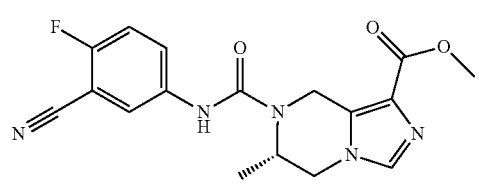
11a
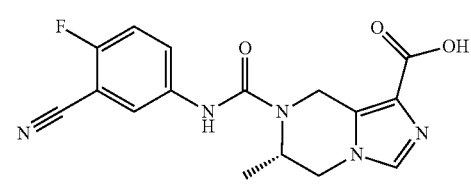
11b
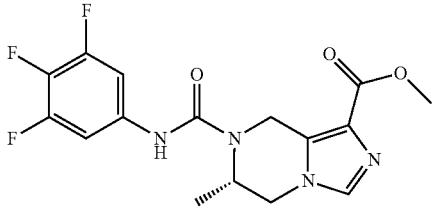
13a
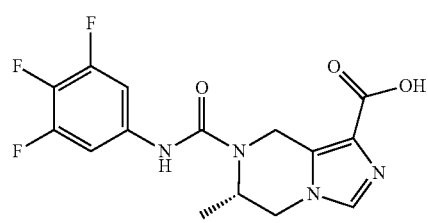
13b
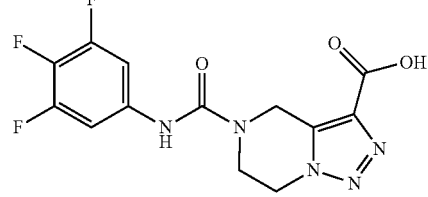
17e
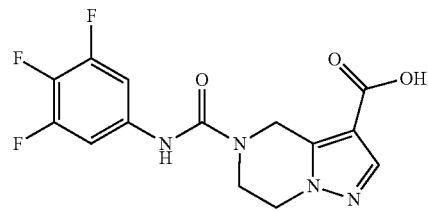
19a

11. A compound of formula (IIIA):

(IIIA)

or a tautomer, mesomer, racemate, enantiomer, diastereomer thereof, or mixture thereof, or a pharmaceutically acceptable salt thereof,
wherein:
M is trifluoroacetic acid or hydrochloric acid;
$R^1$ is selected from the group consisting of alkyl, cycloalkyl, phenyl and heterocyclyl, wherein the alkyl $_mR^6$ is further substituted by one or more substituents selected from the group consisting of halogen, alkoxy and hydroxy, wherein the cycloalkyl is optionally further substituted by one or more alkyl, wherein the phenyl is optionally further substituted by one or more halogen, and wherein the heterocyclyl is optionally further substituted by one or more alkyl;
each $R^3$ is identical or different and each is independently selected from the group consisting of hydrogen and alkyl;
t is 0 or 1;
n is 0, 1, 2 or 3;
wherein
the alkyl is $C_{1-6}$ alkyl;
the alkoxy is $C_{1-6}$ alkoxy;
the cycloalkyl is 3 to 6 membered cycloalkyl; and
the heterocyclyl is 3 to 8 membered heterocyclyl with oxygen as the hetero atom.

12. A compound selected from the group consisting of:

13. A method for preparing the compound according to claim 1, comprising a step of:

reacting a compound of formula (IA) with a compound of formula (IB) or a salt thereof to obtain the compound of formula (I),
wherein:
$R^a$ is hydrogen or alkyl;
each $R^3$ is identical or different and each is independently selected from the group consisting of hydrogen and alkyl;
wherein
the alkyl is $C_{1-6}$ alkyl.

14. A pharmaceutical composition, comprising a therapeutically effective amount of the compound according to claim 1, and a pharmaceutically acceptable carrier, diluent, or excipient.

15. A method of treating a hepatitis B viral infection in a subject in need thereof, the method comprising administering the pharmaceutical composition according to claim 14 to the subject.

16. A pharmaceutical composition, comprising a therapeutically effective amount of the compound according to claim 7, and a pharmaceutically acceptable carrier, diluent, or excipient.

17. A method of treating a hepatitis B viral infection in a subject in need thereof, the method comprising administering the pharmaceutical composition according to claim 16 to the subject.

18. A pharmaceutical composition, comprising a therapeutically effective amount of the compound according to claim 8, and a pharmaceutically acceptable carrier, diluent, or excipient.

19. A method of treating a hepatitis B viral infection in a subject in need thereof, the method comprising administering the pharmaceutical composition according to claim 18 to the subject.

* * * * *